(12) United States Patent
Movsesian

(10) Patent No.: US 8,722,866 B2
(45) Date of Patent: May 13, 2014

(54) ISOFORM-SELECTIVE INHIBITORS AND ACTIVATORS OF PDE3 CYCLIC NUCLEOTIDE PHOSPHODIESTERASES

(75) Inventor: Matthew A. Movsesian, Salt Lake City, UT (US)

(73) Assignee: The United States of America, as Represented by the Department of Veterans Affairs, Washington, DC (US)

( * ) Notice: Subject to any disclaimer, the term of this patent is extended or adjusted under 35 U.S.C. 154(b) by 956 days.

(21) Appl. No.: 11/654,858

(22) Filed: Jan. 18, 2007

(65) Prior Publication Data

US 2010/0267046 A1    Oct. 21, 2010

Related U.S. Application Data

(62) Division of application No. 10/175,161, filed on Jun. 19, 2002, now abandoned.

(60) Provisional application No. 60/309,271, filed on Aug. 1, 2001.

(51) Int. Cl.
| | |
|---|---|
| C12N 9/16 | (2006.01) |
| C12N 9/18 | (2006.01) |
| C07H 21/04 | (2006.01) |
| A61K 31/495 | (2006.01) |

(52) U.S. Cl.
USPC ............ 536/23.2; 435/6.1; 435/7.1; 435/7.6; 435/91.1; 435/196; 536/23.1; 536/24.31

(58) Field of Classification Search
USPC ........ 435/6.1, 7.1, 7.6, 91.1, 196, 375; 514/1, 514/2, 44; 536/23.1, 23.2, 24.31; 425/9.1, 425/9.2
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,196,265 A | 4/1980 | Koprowski et al. | |
| 4,215,051 A | 7/1980 | Schroeder et al. | |
| 4,275,149 A | 6/1981 | Litman et al. | |
| 4,277,437 A | 7/1981 | Maggio | |
| 4,366,241 A | 12/1982 | Tom et al. | |
| 4,554,101 A | 11/1985 | Hopp | |
| 4,683,195 A | 7/1987 | Mullis et al. | |
| 4,683,202 A | 7/1987 | Mullis | |
| 4,800,159 A | 1/1989 | Mullis et al. | |
| 4,883,750 A | 11/1989 | Whiteley et al. | |
| 5,168,053 A | 12/1992 | Altman et al. | |
| 5,279,721 A | 1/1994 | Schmid | |
| 5,354,855 A | 10/1994 | Cech et al. | |
| 5,401,511 A | 3/1995 | Margalit | |
| 5,405,766 A | 4/1995 | Kallury et al. | |
| 5,565,332 A | 10/1996 | Hoogenboom et al. | |
| 5,596,079 A | 1/1997 | Smith et al. | |
| 5,603,872 A | 2/1997 | Margalit | |
| 5,614,396 A | 3/1997 | Bradley et al. | |
| 5,624,824 A | 4/1997 | Yuan et al. | |
| 5,624,830 A | 4/1997 | Mullen et al. | |
| 5,625,047 A | 4/1997 | Been et al. | |
| 5,798,246 A | 8/1998 | Au-Young et al. | |
| 5,858,804 A | 1/1999 | Zanzucchi et al. | |
| 5,948,627 A | 9/1999 | Lee et al. | |
| 5,986,076 A | 11/1999 | Rothschild et al. | |
| 6,031,071 A | 2/2000 | Mandeville et al. | |
| 6,068,829 A | 5/2000 | Ruoslahti et al. | |
| 6,071,394 A | 6/2000 | Cheng et al. | |
| 6,100,037 A * | 8/2000 | Phillips et al. | 506/9 |
| 6,146,876 A | 11/2000 | Robison et al. | |
| 6,210,892 B1 | 4/2001 | Bennett et al. | |
| 6,248,724 B1 | 6/2001 | Moore et al. | |
| 6,277,981 B1 | 8/2001 | Tu et al. | |
| 6,300,492 B1 | 10/2001 | Korneluk et al. | |
| 6,303,374 B1 | 10/2001 | Zhang et al. | |
| 6,310,047 B1 | 10/2001 | Farrell et al. | |
| 6,365,345 B1 | 4/2002 | Brysch et al. | |
| 6,380,161 B1 | 4/2002 | Williams et al. | |
| 6,500,610 B1 | 12/2002 | Pamukcu et al. | |
| 6,812,339 B1 * | 11/2004 | Venter et al. | 536/24.31 |

FOREIGN PATENT DOCUMENTS

| | | |
|---|---|---|
| EP | 329 822 | 8/1989 |
| EP | 1145717 | 10/2001 |
| WO | WO 89/06700 | 7/1989 |
| WO | WO0135979 | 5/2001 |
| WO | WO 01/44449 | 6/2001 |
| WO | WO 03/012030 A2 | 2/2003 |

OTHER PUBLICATIONS

Sette et al, J. Biol. Chem., vol. 271, No. 28, pp. 16,526-16,534 (1996).*
Riken, Nature, vol. 409, pp. 685-690 (2001).*
Ahmad et al., Cyclic Nucleotide Phosphodiesterase 3B Is a Downstream Target of Protein Kinase B and May Be Involved in Regulation of Effects of Protein Kinase B on Thymidine Incorporation in FDCP2 Cells, Journal of Immunology, 2000, pp. 4678-4688, vol. 164.
Anderson et al., Protein Kinase B/Akt Induces Resumption of Meiosis in Xenopus Oocytes, J. Biol. Chem., vol. 273, Issue 30, 18705-708, Jul. 1998. Retrieved from the Internet on Feb. 13, 2003, http://www.jbc.org/cgi/content/full/273/30/18705, 13 pages.

(Continued)

*Primary Examiner* — Jane Zara
(74) *Attorney, Agent, or Firm* — Robert Gorman; Gorman Law Offices

(57) ABSTRACT

The present invention concerns methods and compositions related to type 3 phosphodiesterases (PDE3). Certain embodiments concern isolated peptides corresponding to various PDE3A isoforms and/or site-specific mutants of PDE3A isoforms, along with expression vectors encoding such isoforms or mutants. In specific embodiments, methods for identifying isoform-selective inhibitors or activators of PDE3 are provided, along with methods of use of such inhibitors or activators in the treatment of dilated cardiomyopathy, pulmonary hypertension and/or other medical conditions related to PDE3 effects on cAMP levels in different intracellular compartments.

10 Claims, 11 Drawing Sheets

(56) References Cited

OTHER PUBLICATIONS

Atienza et al., Identification of Inhibitor Specificity Determinants in a Mammalian Phosphodiesterase, J. Biol. Chem., vol. 274, Issue 8, 4839-47, Feb. 1999. Retrieved from the Internet on Dec. 10, 2002, http://www.jbc.org/cgi/content/full/274/8/4839, 19 pages.
Bass et al., The Short Answer, Nature, 411, 428-29, May 2001.
Beemon K, and Hunter T Characterization of Rous sarcoma virus src gene products synthesized in vitro. J Virol. 28(2):551-66, 1978.
Berzal-Herranz et al., Genes and Devel., 6:129-134, 1992.
Böhm et al., cAMP concentrations, cAMP dependent protein kinase activity, and phospholamban in non-failing and failing myocardium. Cardiovasc Res, 1994, 28:1713-1719.
Branch, Trends in Biochem. Sci (TIBS), 1998, pp. 45-50, vol. 23.
Buxton et al., Compartments of cyclic AMP and protein kinase in mammalian cardiomyocytes, J Biol Chem Sep. 10, 1983;258(17):10233-9.
Cheung et al., Human platelet eGI-PDE: expression in yeast and localization of the catalytic domain by deletion mutagenesis. Blood, 1996, 88:1321-1329.
Chirila et al., Biomaterials, 2002, pp. 321-342, vol. 23.
Choi et al., Identification of a Novel Isoform of the Cyclic-Nucleotide Phosphodiesterase PDE3A Expressed in Vascular Smooth-Muscle Myocytes, Biochem. J. 2001, 353, 41-50. Retrieved from the Internet on Dec. 10, 2002, http:///www.biochemj.org/bj/353/0041/bj3530041.htm, 13 pages.
Chowrira et al., "In vitro and in vivo comparison of hammerhead, hairpin, and hepatitis delta virus self-processing ribozyme cassetyes," J. Biol. Chem., 269:25856-25864, 1994.
Chowrira et al, Biochemistry, 32:1088-1095, 1993.
Claycomb et al. HL-1 cells: A cardiac muscle cell line that contracts and retains phenotypic characteristics of the adult cardiomyocyte. Proc Natl Acad Sci USA 95:2979-2984, 1998.
Colberre-Garapin et al., J. Mol. Biol., 150: 1, 1981.
Cook et al., Inhibition by cAMP of Ras-dependent activation of Raf. Science, 1993, 262: 1069-1072.
Crooke, Antisense Res. & Application, Chapters 1 and 2, 1998, pp. 1-50, S. Crooke, Ed. Publ. by Springer-Vertag (1998).
Dawson et al., Cilostazol has beneficial effects in treatment of intermittent claudication: results from a multicenter, randomized, prospective, double-blind trial. Circulation 98:678-686, 1998.
Database GenCore, Sequence alignment data for SEQ ID No. 3.
Derossi et al., J. Biol. Chem., 1994, pp. 10,444-10,450, vol. 289, No. 14.
Dodge et al., mAKAP assembles a protein kinase A/PDE4 phosphodiesterase cAMP signaling module, EMBO J Apr. 7, 2001;20(8):1921-30.
Duan et al., Phosphatidylinositol 3-kinase is required for insulin-like growth factor-I-induced vascular smooth muscle cell proliferation and migration, Circ Res Jan. 7-21, 2000;86(1):15-23.
Elbashir et al., Duplexes of 21-Nucleotide RNAs Mediate RNAs Interference in Cultured Mammalian Cells, Nature, 411, 494-98, May 2001.
Elliott et al., Cell, 1997, pp. 223-233, vol. 88.
Fentzke et al., Dilated Cardiomyopathy in Transgenic Mice Expressing a Dominant-Negative CREB Transcription Factor in the Heart, J Clin Invest 101:2415-26, 1998.
Fischmeister et al., Regulation of calcium current by low-$K_m$ cyclic AMP phosphodiesterases in cardiac cells. Mol Pharmacol 38:426-433, 1990.
Flori et al., Solubilization of Membrane-Bound Rod Phosphodiesterase by the Rod Phosphodiesterase Recombinant Delta & Subunit, J Biol Chem 271:24036-47, 1996. Retrieved from the Internet on Feb. 14, 2003, http://www.jbc.org/cgi/content/full/271/39/24036, 24 pages.
Forster et al., Cell, 49:211-220, 1987.
Fransen et al., Identification of Peroxisomal Proteins by Using M13 Phage Protein VI Phage Display: Molecular Evidence that Mammalian Peroxisomes Contain a 2,4-Dienoyl-CoA Reductase, Biochem. J., 1999, 340, 561-68. Retrieved from the Internet on Dec. 11, 2002, http://www.biochemj.org/bj/340/0561/bj-3400561.htm, 12 pages.
Fu et al., Masters SC. 14-3-3 proteins: structure, function, and regulation. Annu Rev Pharmacol Toxicol 40:617-647, 2000.
Fujio et al., Akt promotes survival of cardiomyocytes in vitro and protects against ischemia-reperflision injury in mouse heart. Circulation 101:660-667, 2000.
Gefter et al., Somatic Cell Genet., 3:231-236, 1977.
Gibson, W. Polyoma virus proteins: a description of the structural proteins of the virion based on polyacrylamide gel electrophoresis and peptide analysis. Virology 62(2):319-36, 1974.
Grant et al., cAMP-mediated phosphorylation of the low-Km cAMP phosphodiesterase markedly stimulates its catalytic activity, Proc Natl Acad Sci U S A Dec. 1988;85(23):9071-5.
Guillain et al., A Direct Fluorescence Study of the Transient Steps Induced by Calcium Binding to Sarcoplasmic Reticulum ATPase, J Biol Chem 255:2072-2075,1980.
Haseloff and Gerlach, Nature, 334:585-591, 1988.
Hayes JS, Brunton LL, Mayer SE. Selective activation of particulate CAMP-dependent protein kinase by isoproterenol and prostaglandin $E_1$. J Biol Chem 255:5113-5119, 1980.
Hitzman et al., Isolation and Characterization of the Yeast 3-Phosphoglycerokinase Gene (PGK) by an Immunological Screening Technique, The Journal of Biological Chemistry, Dec. 25, 1980, pp. 12073-12080, vol. 255, No. 24.
Hoffmann et al., cAMP-Specific Phosphodiesterase HSPDE4D3 Mutants which Mimic Activation and Changes in Rolipram Inhibition Triggered by Protein Kinase A Phosphorylation of Ser-54 Generation of a Molecular Model, Biochem J 333:139-49, 1998. Retrieved from the Internet on Dec. 11, 2002, http://www.biochemj.org/bj/333/0139/bj330130.htm, 18 pages.
Hoffmann et al., The MAP kinase ERK2 inhibits the cyclic AMP-specific phosphodiesterase HSPDE4D3 by phosphorylating it at Ser579, EMBO J Feb. 15, 1999;18(4):893-903.
Hohl et al., Compartmentation of cAMP in adult canine ventricular myocytes. Relation to single-cell free Ca2+ transients, Circ Res Nov. 1991;69(5):1369-79.
Holland et al., Biochemistry, 17:4900, 1978.
Jurevicius et al., cAMP Compartmentation is Responsible for a Local Activiation fo Cardiac $Ca^{2+}$ Channels by Beta-Adrenergic Agonists, Proc Natl Acad Sci., 93: 295-99, 1996.
Kasuya et al., Cardiac type cGMP-inhibited phosphodiesterase (PDE3A) gene structure: Similarity and difference to adipocyte type PDE3B gene. Biochem Biophys Res Comm, 2000, 268:827-834.
Kasuya et al., Multiple Transcripts for the Human Cardiac Form of the cGMP-inhibited cAMP Phosphodiesterase, J. Biol Chem 270:14305-312, 1995. Retrieved from the Internet on Dec. 11, 2002, http://www.jbc.org/cgi/content/full/270/24/14305, 18 pages.
Kenan et al, Functions of the N-terminal region of cyclic nucleotide phosphodiesterasae 3 isoforms. J Biol Chem 275:12331-12338, 2000.
Kingsman et al., Gene, 7:141, 1979.
Kitamura et al. Insulin-induced phosphorylation and activation of cyclic nucleotide phosphodiesterase 3B by the serine-threonine kinase akt. Mol Cell Biol 19:6286-6296, 1999.
Kohler and Milstein, Eur. J. Immunol., 6:511-519, 1976.
Kohler and Milstein, Nature, 256:495-497, 1975.
Krall et al., Identification and quantitation of cAMP-dependent protein kinase R subunit isoforms in subcellular fractions of human myocardium. J Mol Cell Cardiol 31:971-980, 1999.
Kwoh et al., Proc. Nat. Acad. Sci. USA, 86: 1173, 1989.
Kyte and Doolittle, J. Mol. Biol., 157(1):105-132, 1982.
Lazou et al., Regulation of mitogen-activated protein kinase cascade in adult rat heart preparations in vitro. Circ Res 75:932-941, 1994.
Liu et al., Expression of cyclic GMP-inhibited phosphodiesterases 3A and 3B (PDE3A and PDE3B) in rat tissues: differential subcellular localization and regulated expression by cyclic AMP. Br J Pharmacol 125:1501-1510, 1998.
Lopez-Aparicio et al., Stimulation by insulin of a serine kinase in human platelets that phosphorylates and activates the cGMP-inhibited cAMP phosphodiesterase. Biochem Biophys Res Commun 193:1137-44, 1993.

(56) References Cited

OTHER PUBLICATIONS

Lowy et al, Cell, 22:817, 1980.
Luo, et al., Transfer of proteins to membranes facilitates both cyanogen bromide cleavage and two-dimensional proteolytic mapping. Oncogene 5:921-3, 1990.
Lutz et al., Increased activity of membrane-associated nucleoside diphosphate kinase and inhibition of cAMP synthesis in failing human myocardium. Cardiovasc Res 49:48-55, 2001.
Matsui et al., Adenoviral gene transfer of activated phosphatidylinositol 3'-kinase and Akt inhibits apoptosis of hypoxic cardiomyocytes in vitro, Circulation Dec. 7, 1999;100(23):2373-9.
McPhee et al., Association with the SRC Family Tyrosyl Kinase LYN Triggers a Conformational Change in the Catalytic Region of Human cAMP-Specific Phosphodiesterase HSPDE4A4B, J. Biol Chem 274:11796-810, 1999. Retrieved from the Itnernet on Dec. 11, 2002, http://www.jbc.org/cgi/content/full/274/17/11796, 26 pages.
Meacci et al., Molecular cloning and expression of human myocardial cGMP-inhibited cAMP phosphodiesterase, Proc Natl Acad Sci, 1992, pp. 3721-3725, vol. 89, USA.
Merrifield, Science, 232: 341-347, 1986.
Minamisawa et al., Chronic Phospholamban-Sarcoplasmic Reticulum Calcium ATPase Interaction is the Critical Calcium Cycling Defect in Dilated Cardiomyopathy, Cell, 1999, 99:313-22. Retrieved from the Internet on Dec. 11, 2002, http://www.cell.com/cgi/content/full/99/3/313, 13 pages.
Movsesian, Beta-Adrenergic Receptor Agonists and Cyclic Nucleotide Phosphodiesterase Inhibitors Shifting the Focus from Inotropy to Cyclic Adenosine Monophosphoate, J Am Coll Cardiol, 1999, 34:318-24.
Movsesian et al., Inhibitors of Cyclic Nucleotide Phosphodiesterase PDE3 as Adjunct Therapy for Dilated Cardiomyopathy, Exp. Opin. Invest. Drugs, 2002, 11(11), 8 pages.
Movsesian et al., Phosphorylation of phospholamban by calcium-activated, phospholipid-dependent protein kinase. Stimulation of cardiac sarcoplasmic reticulum calcium uptake, J Biol Chem Jul. 10, 1984:259(13):8029-32.
Movesian, Therapeutic Potential of Cyclic Nucleotide PDE Inhibitors in Heart Failure, Exp. Opin. Invest. Drugs, 2000, 9(5), 11 pages.
Mulligan et al., Proc. Nat'l Acad. Sci. USA, 78:2072, 1981.
Nony et al., Evaluation of the effect of phosphodiesterase inhibitors on mortality in chronic heart failure patients, 1994, Eur J Clin Pharmacol 46:191-196.
Ohara et al., Proc. Nat'l Acad. Sci. USA, 86-5673-5677, 1989.
O'Hare et al., Proc. Nat'l Acad. Sci. USA, 78:1527, 1981.
Osinski et al., Inhibition of platelet-derived growth factor-induced mitogenesis by phosphodiesterase 3 inhibitors: role of protein kinase A in vascular smooth muscle cell mitogenesis. Biochem Pharmacol, 2000, 60:381-387.
Palukaitis et al., Virology, 99:145-151, 1979.
Park et al., Effects of cilostazol on angiographic restenosis after coronary stent placement. Am J C'ardiol 86:499-503, 2000.
PCT International Search Report, PCT/US02/19319, dated Jul. 23, 2003.
Perriman et al., Gene, 113:157-163, 1992.
Peracchi et al., Rev. Med. Virol., 2004, vol. 14, pp. 47-64.
Pooga et al., FASEB J., 1998, pp. 67-77, vol. 12.
Polacek et al., Ribosomal peptidyl transferase can withstand mutations at the putative catalytic nucleotide, Nature, May 24, 2001, vol. 411, pp. 498.
Prody et al., Science, 231:1577-1580, 1986.
Rahn et al., Identification of the Site in the cGMP-Inhibited Phosphodiesterase Phosphorlated in Adipocytes in Response to Insulin and Isoproterenol, J Biol Chem, 1996, 271:11575-580. Retrieved from the Internet on Dec. 11, 2002, http://www.jbc.org/cgi/content/full/271/19/11575, 14 pages.
Rapundalo et al., Inotropic responses to isoproterenol and phosphodiesterase inhibitors in intact guinea pig hearts: comparison of cyclic AMP levels and phosphorylation of sarcoplasmic reticulum and myofibrillar proteins, Circ Res Jan. 1989;64(1):104-11.
Rascón et al., Identification of the phosphorylation site in vitro for cAMP-dependent protein kinase on the rat adipocyte cGMP-inhibited cAMP phosphodiesterase. J Biol Chem 269:11962-11966, 1994.
Reinhardt et al., Distinctive anatomical patterns of gene expression of cGMP-inhibited cyclic nucleotide phosphodiesterases, J Clin Invest Apr. 1995;95(4):1528-38.
Resjö et al., Phosphorylation and activation of phosphodiesterase type 3B (PDE3B) in adipocytes in response to serine/threonine phosphatase inhibitors: deactivation of PDE3B in vitro by protein phosphatase type 2A. J Biol Chem 341:839-845, 1999.
Rocic et al., (Mar. 21, 2001 [epub ahead of print]) Downregulation by antisense oligonucleotides establishes a role for the praline-rich tyrosine kinase PYK2 in angiotensin II-induced signalling in vascular smooth muscle. J Biol Chem.
Rondinone et al., Phosphorylation of PDE3B by phosphatidylinositol 3-kinase associated with the insulin receptor. J Biol Chem 275:10093-10098, 2000.
Rosenmund et al., Anchoring of protein kinase A is required for modulation of AMPA/kainate receptors on hippocampal neurons, Nature Apr. 28, 1994:368(6474):853-6.
Sandirasegarane et al., NO regulates PDGF-induced activation of PKB but not ERK in A7r5 cells: implications for vascular growth arrest. Am J Physiol Cell Physiol., 2000, 279:C225-35.
Santerre et al., Gene, 30:147-156, 1984.
Sarver, et al., Science, 247:1222-1225, 1990.
Scanlon et al., Proc Natl Acad Sci USA, 88:10591-10595, 1991.
Schillace et al., Multiple Interactions within the AKAP220 Signaling Complex Contribute to Protein Phosphatase 1 Regulation, J Biol Chem 2001, 276:12128-34. Retrieved from the Internet on Dec. 11, 2002, http:///www.jbc.org/cgi/content/full/276/15/12128, 16 pages.
Shakur et al., Regulation and function of the cyclic nucleotide phosphodiesterase PDE3 gene family. Prog Nucleic Acid Res Mol Biol 66:241-77, 2000a.
Shakur et al., Membrane localization of cyclic nucleotide phosphodiesterase 3 (PDE3). J Biol Chem 49:38749-38761, 2000b.
Simmerman, et al. Phospholamban: protein structure, mechanism of action, and role in cardiac function. Physiol Rev 78:921-947, 1998.
Sioud et al., J Mol. Biol., 223:831-835, 1992.
Smith et al., Cytosolic and sarcoplasmic reticulum-associated low $K_m$, cGMP-inhibited cAMP phosphodiesterase in mammalian myocardium. Biochem Biophys Res Comm 190:516-521, 1993.
Smith et al., Hormone-sensitive cGMP-inhibited cAMP phosphodiesterase in rat adipocytes: Regulation of insulin- and cAMP-dependent activation by phosphorylation. J Biol Chem 266:13385-13390, 1991.
Sonnenburg et al., Identification of Inhibitory and Calmodulin-binding Domains of the PDE1A1 and PDE1A2 Calmodulin-Stimulated Cyclic Nuclotide Phosphodiesterases, J. Biol Chem 1995, 270:30989-31000. Retrieved from the Internet on Dec. 11, 2002, http://www.jbc.org/cgi/content/full/270/52/30989, 24 pages.
Stinchcomb et al., Nature, 282:39, 1979.
Taira et al., Molecular Cloning of the Rat Adipocyte Hormone-sensitive Cyclic GMP-inhibited Cyclic Nucleotide Phosphodiesterase, Journal of Biological Chemistry, Sep. 5, 1993, pp. 18573-18579, vol. 268, No. 25.
Tang et al., Expression and Mutagenesis of the Catalytic Domain of cGMP-Inhibited Phosphodiesterase (PDE3) Cloned from Human Platelets, Biochem. J., 1997, 323:217-24. Retrieved from the Internet on Dec. 11, 2002, http://www.biochemj.org/bj/323/0217/bj3230217.htm, 12 pages.
Tschemper et al., Gene, 10:157, 1980.
Walker et al., Proc. Nat'l Acad. Sci. USA, 89: 392-396, 1992.
Wechsler et al., Isoforms of Cyclic Nucleotide Phosphodiesterase PDE3A in Cardiac Myocytes, The Journal of Biological Chemistry, 2002, pp. 38072-38078, vol. 277, No. 41.
Wigler et al., Cell, 11:223, 1977.
Wigler et al., Proc. Nat'l Acad. Sci. USA, 77:3567, 1980.
Wu et al., Genomics, 4:560, 1989.
Wu et al., Expression of Constitutively Active Phosphatidylinositol 3-Kinase Inhibits Activation of Caspase 3 and Apoptosis of Cardiac Muscle Cells, J Biol Chem 2000, 275:40113-19. Retrieved from the Internet on Dec. 11, 2002, http://www.jbc.org/cgi/content/full/275/51/40113, 17 pages.

(56) References Cited

OTHER PUBLICATIONS

Xiao et al., Beta 2-adrenergic receptor-stimulated increase in cAMP in rat heart cells is not coupled to changes in Ca2+ dynamics, contractility, or phospholamban phosphorylation, J Biol Chem Jul. 22, 1994;269(29):19151-6.
Xiao et al., Beta 1-adrenoceptor stimulation and beta 2-adrenoceptor stimulation differ in their effects on contraction, cytosolic Ca2+, and Ca2+ current in single rat ventricular cells, Circ Res Aug. 1993;73(2):286-300.
Xu et al., Atomic structure of PDE4: insights into phosphodiesterase mechanism and specificity. Science 288:1822-1825, 2000.
Yarwood et al., The RACK1 Signaling Scaffold Protein Selectively Interacts with the cAMP-Specific Phosphodeiesterase PDE4D5 Isoform, J. Biol Chem, 1999, 274:14909-17, 28 pages. Retrieved from the Internet on Dec. 11, 2002, http://www.jbc.org/cgi/content/full/274/21/4909, 28 pages.
Yuan and Altman, Science, 263:1269-1273, 1994.
Yuan et al., Proc. Natl. Acad. Sci. USA, 89:8006-8010, 1992.
Zhang et al., Conserved amino acids in metal-binding motifs of PDE3A are involved in substrate and inhibitor binding. Blood 95:3380-3386, 2000.
Zhao et al., Leptin inhibits insulin secretion by activation of phosphodiesterase 3B, J Clin Invest Sep. 1, 1998;102(5):869-73.
Zozulya et al., Mapping signal transduction pathways by phage display. Nature Biotech 17:1193-1198, 1999.
Certificate of European Patent issued Sep. 15. 2010 re EP Application No. 02739923.
Multiple sequence alignment (CLUSTALW) of GENBANK_ID:A44093 ,GENBANK_ID:AF161582 and SEQ_ID:1-3 of the appplication.
Notification of Transmittal of the International Search Report mailed Jul. 23, 2003 re PCT/US02/19319.
Supplementary European Search Report issued re EP Application No. 02739923 dated Nov. 30, 2004.
Article 94(3) EPC Communication issued Mar. 3, 2005 re EP Application No. 02739923.
Response to Mar. 3, 2005 Communication, filed Sep. 12, 2005 re EP Application No. 02739923.
Article 94(3) EPC Communication issued Mar. 9, 2007 re EP Application No. 02739923.
Response to Mar. 9, 2007 Communication, filed Nov. 19, 2007 re EP Application No. 02739923.
Article 94(3) EPC Communication issued Jan. 14, 2008 re EP Application No. 02739923.
Response to Jan. 14, 2008 Communication, filed Nov. 4, 2008 re EP Application No. 02739923.
Summons to Attend Oral Proceedings issued Jun. 16, 2009 re EP Application No. 02739923.
Response to Jun. 16, 2009 Summons to Attend Oral Proceedings, filed Dec. 18, 2009 re EP Application No. 02739923.
Auxiliary Request, filed Jan. 20, 2010 re EP Application No. 02739923.
Minutes of Oral Proceedings opened on Jan. 20, 2010 re EP Application No. 02739923.
Decision to Grant European Patent issued Aug. 19, 2010 re EP Application No. 02739923.
Certificate of European Patent issued Sep. 15, 2010 re EP Application No. 02739923.
Office Action issued Mar. 11, 2008 re Japanese Patent Application No. 2003-517203 w/English translation.
[database abstract] Prous Science Integrity (accession No. 261660);Otsuka OPC-33540 is a potent and selective inhbitor of phosphodiesterase type III. Drug Data Rep 1998.
Parker, J. C. et al. "Effect of cyclic AMP phosphodiesterase inhibitors on insulin secretion and lycemia." Diabetologia, Berlin, DE, 39(1):A225 (1996).
Schermuly, R. et al. "Subthreshold doses of specific phosphodiesterase type 3 and 4 inhibitors enhance the pulmonary vasocilatory response to nebulized prostacyclin with improvement in gas exchange." J. Pharm. and Exp. Therap. 292 (2):512-520 (2000).
Wagner, R.S. et al. "Phosphodiesterase inhibition improves agonist-induced relaxation of hypertensive pulmonary arteries." J. Pharm. and Exp. Therap. 282(3):1650-1657 (1997).
Notice of Abandonment mailed Jun. 27, 2007 re U.S. Appl. No. 10/175,161.
Non-Final Rejection mailed Oct. 18, 2006 re U.S. Appl. No. 10/175,161.
Amendment and Request for Continued Examination, filed Aug. 15, 2007 re U.S. Appl. No. 10/175,161.
Final Rejection mailed Mar. 15, 2006 re U.S. Appl. No. 10/175,161.
Amendment after Non-Final Rejection, filed Dec. 20, 2005 re U.S. Appl. No. 10/175,161.
Non-Final Rejection mailed Jun. 20, 2005 re U.S. Appl. No. 10/175,161.
Amendment and Response to Election/Restriction Rejection, filed Mar. 15, 2005.
Requirement for Restriction/Election mailed Dec. 15, 2004.
Agrawal, S. et al. Molecular Med. Today, 6:72-81 (2000).
Branch, A. Trends in Biochem. Sci (TIBS), 23:45-50 (1998).
Chirila, T. et al., Biomaterials 23:321-342 (2002).
Crooke, S., Antisense Res. & Application, Chapters 1 and 2, pp. 1-50, S. Crooke, Ed. Publ. by Springer-Vertag (1998).
Derossi, D. et al. J. Biol. Chem. 289(14):10,444-10,450 (1994).
Elliott, G. et al. Cell, 8:223-233 (1997).
Peracchi, A. et al. Rev. Med. Virol. 14:47-64 (2004).
Pooga, M. et al. Faseb J. 12:67-77 (1998).

* cited by examiner

*FIG. 5*
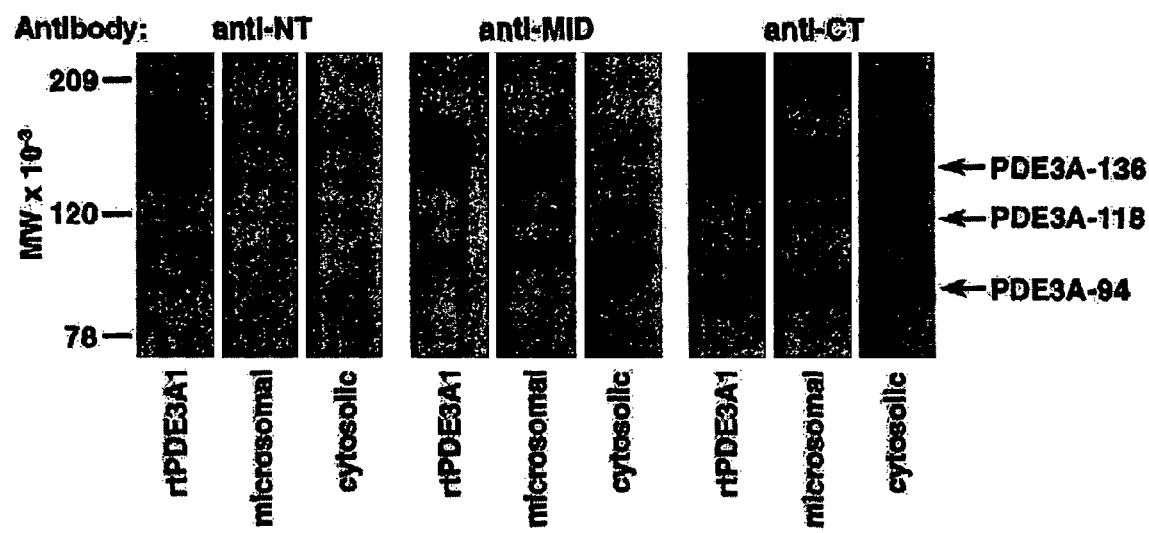
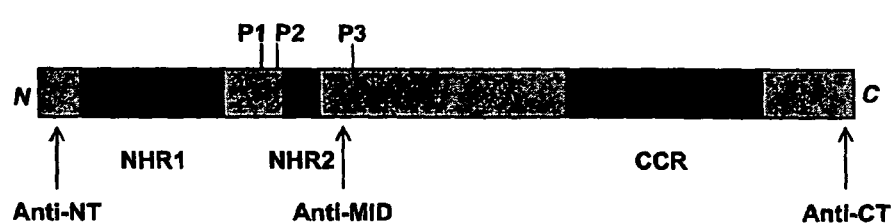

MAVPGDAARV RNKPVHSGVS QAPTAGRDCH HRADPASPRD SGCRGCWGDL VLQPLRSSRK
LSSALCAGSL SFLLALLVRL VRGEVGCDLE QCKEAAAAEE EEAAPGAEGG VFPGPRGGAP
GGGARLSPWL QPSALLFSLL CAFFWMGLYL LRAGVRLPLA VALLAACCGG EALVQIGLGV
GEDHLLSLPA AGVVLSCLAA ATWLVLRLRL GVLMIALTSA VRTVSLISLE RFKVAWRPYL
AYLAGVLGIL LARYVEQILP QSAEAAPREH LGSQLIAGTK EDIPVFKRRR RSSSVVSAEM
SGCSSKSHRR TSLPCIPREQ LMGHSEWDHK RGPRGSQSSG TSITVDIAVM GEAHGLITDL
LADPSLPPNV CTSLRAVSNL LSTQLTFQAI HKPRVNPVTS LSENYTCSDS EESSEKDKLA
IPKRLRRSLP PGLLRRVSST WTTTTSATGL PTLEPAPVRR DRSTSIKLQE APSSSPDSWN
NPVMMTLTKS RSFTSSYAIS AANHVKAKKQ SRPGALAKIS PLSSPCSSPL QGTPASSLVS
KISAVQFPES ADTTAKQSLG SHRALTYTQS APDLSPQILT PPVICSSCGR PYSQGNPADE
PLERSGVATR TPSRTDDTAQ VTSDYETNNN SDSSDIVQNE DETECLREPL RKASACSTYA
PETMMFLDKP ILAPEPLVMD NLDSIMEQLN TWNFPIFDLV ENIGRKCGRI LSQVSYRLFE
DMGLFEAFKI PIREFMNYFH ALEIGYRDIP YHNRIHATDV LHAVWYLTTQ PIPGLSTVIN
DHGSTSDSDS DSGFTHGHMG YVFSKTYNVT DDKYGCLSGN IPALELMALY VAAAMHDYDH
PGRTNAFLVA TSAPQAVLYN DRSVLENHHA AAAWNLFMSR PEYNFLINLD HVEFKHFRFL
VIEAILATDL KKHFDFVAKF NGKVNDDVGI DWTNENDRLL VCQMCIKLAD INGPAKYKEL
HLQWTDGIVN EFYEQGDEEA SLGLPISPFM DRSAPQLANL QESFISHIVG PLCNSYDSAG
LMPGKWVEDS DESGDTDDPE EEEEEAPAPN EEETCENNES PKKKTFKRRK IYCQITQHLL
QNHKMWKKVI EEEQRLAGIE NQSLDQTPQS HSSEQIQAIK EEEEEKGKPR GEEIPTQKPD
Q

FIG. 11

SEQUENCE LISTING

```
<160> NUMBER OF SEQ ID NOS: 18

<210> SEQ ID NO 1
<211> LENGTH: 996
<212> TYPE: PRT
<213> ORGANISM: Homo sapiens
```

```
<400> SEQUENCE: 1

Met Gly Leu Tyr Leu Leu Arg Ala Gly Val Arg Leu Pro Leu Ala Val
1               5                   10                  15

Ala Leu Leu Ala Ala Cys Cys Gly Gly Glu Ala Leu Val Gln Ile Gly
            20                  25                  30

Leu Gly Val Gly Glu Asp His Leu Leu Ser Leu Pro Ala Ala Gly Val
        35                  40                  45

Val Leu Ser Cys Leu Ala Ala Ala Thr Trp Leu Val Leu Arg Leu Arg
50                  55                  60

Leu Gly Val Leu Met Ile Ala Leu Thr Ser Ala Val Arg Thr Val Ser
65                  70                  75                  80

Leu Ile Ser Leu Glu Arg Phe Lys Val Ala Trp Arg Pro Tyr Leu Ala
                85                  90                  95

Tyr Leu Ala Gly Val Leu Gly Ile Leu Leu Ala Arg Tyr Val Glu Gln
            100                 105                 110

Ile Leu Pro Gln Ser Ala Glu Ala Ala Pro Arg Glu His Leu Gly Ser
        115                 120                 125

Gln Leu Ile Ala Gly Thr Lys Glu Asp Ile Pro Val Phe Lys Arg Arg
130                 135                 140

Arg Arg Ser Ser Ser Val Val Ser Ala Glu Met Ser Gly Cys Ser Ser
145                 150                 155                 160

Lys Ser His Arg Arg Thr Ser Leu Pro Cys Ile Pro Arg Glu Gln Leu
                165                 170                 175

Met Gly His Ser Glu Trp Asp His Lys Arg Gly Pro Arg Gly Ser Gln
            180                 185                 190

Ser Ser Gly Thr Ser Ile Thr Val Asp Ile Ala Val Met Gly Glu Ala
        195                 200                 205

His Gly Leu Ile Thr Asp Leu Leu Ala Asp Pro Ser Leu Pro Pro Asn
210                 215                 220

Val Cys Thr Ser Leu Arg Ala Val Ser Asn Leu Leu Ser Thr Gln Leu
225                 230                 235                 240

Thr Phe Gln Ala Ile His Lys Pro Arg Val Asn Pro Val Thr Ser Leu
                245                 250                 255

Ser Glu Asn Tyr Thr Cys Ser Asp Ser Glu Glu Ser Ser Glu Lys Asp
            260                 265                 270

Lys Leu Ala Ile Pro Lys Arg Leu Arg Arg Ser Leu Pro Pro Gly Leu
        275                 280                 285

Leu Arg Arg Val Ser Ser Thr Trp Thr Thr Thr Ser Ala Thr Gly
290                 295                 300

Leu Pro Thr Leu Glu Pro Ala Pro Val Arg Arg Asp Arg Ser Thr Ser
305                 310                 315                 320

Ile Lys Leu Gln Glu Ala Pro Ser Ser Pro Asp Ser Trp Asn Asn
                325                 330                 335

Pro Val Met Met Thr Leu Thr Lys Ser Arg Ser Phe Thr Ser Ser Tyr
            340                 345                 350

Ala Ile Ser Ala Ala Asn His Val Lys Ala Lys Gln Ser Arg Pro
        355                 360                 365

Gly Ala Leu Ala Lys Ile Ser Pro Leu Ser Ser Pro Cys Ser Ser Pro
370                 375                 380

Leu Gln Gly Thr Pro Ala Ser Ser Leu Val Ser Lys Ile Ser Ala Val
385                 390                 395                 400

Gln Phe Pro Glu Ser Ala Asp Thr Thr Ala Lys Gln Ser Leu Gly Ser
                405                 410                 415
```

-continued

```
His Arg Ala Leu Thr Tyr Thr Gln Ser Ala Pro Asp Leu Ser Pro Gln
            420                 425                 430

Ile Leu Thr Pro Pro Val Ile Cys Ser Ser Cys Gly Arg Pro Tyr Ser
            435                 440                 445

Gln Gly Asn Pro Ala Asp Glu Pro Leu Glu Arg Ser Gly Val Ala Thr
        450                 455                 460

Arg Thr Pro Ser Arg Thr Asp Thr Ala Gln Val Thr Ser Asp Tyr
465                 470                 475                 480

Glu Thr Asn Asn Ser Asp Ser Ser Asp Ile Val Gln Asn Glu Asp
                485                 490                 495

Glu Thr Glu Cys Leu Arg Glu Pro Leu Arg Lys Ala Ser Ala Cys Ser
            500                 505                 510

Thr Tyr Ala Pro Glu Thr Met Met Phe Leu Asp Lys Pro Ile Leu Ala
            515                 520                 525

Pro Glu Pro Leu Val Met Asp Asn Leu Asp Ser Ile Met Glu Gln Leu
        530                 535                 540

Asn Thr Trp Asn Phe Pro Ile Phe Asp Leu Val Glu Asn Ile Gly Arg
545                 550                 555                 560

Lys Cys Gly Arg Ile Leu Ser Gln Val Ser Tyr Arg Leu Phe Glu Asp
                565                 570                 575

Met Gly Leu Phe Glu Ala Phe Lys Ile Pro Ile Arg Glu Phe Met Asn
            580                 585                 590

Tyr Phe His Ala Leu Glu Ile Gly Tyr Arg Asp Ile Pro Tyr His Asn
        595                 600                 605

Arg Ile His Ala Thr Asp Val Leu His Ala Val Trp Tyr Leu Thr Thr
610                 615                 620

Gln Pro Ile Pro Gly Leu Ser Thr Val Ile Asn Asp His Gly Ser Thr
625                 630                 635                 640

Ser Asp Ser Asp Ser Asp Ser Gly Phe Thr His Gly His Met Gly Tyr
                645                 650                 655

Val Phe Ser Lys Thr Tyr Asn Val Thr Asp Lys Tyr Gly Cys Leu
            660                 665                 670

Ser Gly Asn Ile Pro Ala Leu Glu Leu Met Ala Leu Tyr Val Ala Ala
        675                 680                 685

Ala Met His Asp Tyr Asp His Pro Gly Arg Thr Asn Ala Phe Leu Val
690                 695                 700

Ala Thr Ser Ala Pro Gln Ala Val Leu Tyr Asn Asp Arg Ser Val Leu
705                 710                 715                 720

Glu Asn His His Ala Ala Ala Trp Asn Leu Phe Met Ser Arg Pro
                725                 730                 735

Glu Tyr Asn Phe Leu Ile Asn Leu Asp His Val Glu Phe Lys His Phe
            740                 745                 750

Arg Phe Leu Val Ile Glu Ala Ile Leu Ala Thr Asp Leu Lys Lys His
        755                 760                 765

Phe Asp Phe Val Ala Lys Phe Asn Gly Lys Val Asn Asp Asp Val Gly
770                 775                 780

Ile Asp Trp Thr Asn Glu Asn Asp Arg Leu Leu Val Cys Gln Met Cys
785                 790                 795                 800

Ile Lys Leu Ala Asp Ile Asn Gly Pro Ala Lys Tyr Lys Glu Leu His
                805                 810                 815

Leu Gln Trp Thr Asp Gly Ile Val Asn Glu Phe Tyr Glu Gln Gly Asp
            820                 825                 830

Glu Glu Ala Ser Leu Gly Leu Pro Ile Ser Pro Phe Met Asp Arg Ser
        835                 840                 845
```

-continued

```
Ala Pro Gln Leu Ala Asn Leu Gln Glu Ser Phe Ile Ser His Ile Val
    850                 855                 860

Gly Pro Leu Cys Asn Ser Tyr Asp Ser Ala Gly Leu Met Pro Gly Lys
865                 870                 875                 880

Trp Val Glu Asp Ser Asp Glu Ser Gly Asp Thr Asp Asp Pro Glu Glu
                885                 890                 895

Glu Glu Glu Glu Ala Pro Ala Pro Asn Glu Glu Glu Thr Cys Glu Asn
            900                 905                 910

Asn Glu Ser Pro Lys Lys Lys Thr Phe Lys Arg Arg Lys Ile Tyr Cys
            915                 920                 925

Gln Ile Thr Gln His Leu Leu Gln Asn His Lys Met Trp Lys Lys Val
    930                 935                 940

Ile Glu Glu Glu Gln Arg Leu Ala Gly Ile Glu Asn Gln Ser Leu Asp
945                 950                 955                 960

Gln Thr Pro Gln Ser His Ser Ser Glu Gln Ile Gln Ala Ile Lys Glu
                965                 970                 975

Glu Glu Glu Glu Lys Gly Lys Pro Arg Gly Glu Glu Ile Pro Thr Gln
            980                 985                 990

Lys Pro Asp Gln
            995

<210> SEQ ID NO 2
<211> LENGTH: 842
<212> TYPE: PRT
<213> ORGANISM: Homo sapiens

<400> SEQUENCE: 2

Met Ser Gly Cys Ser Ser Lys Ser His Arg Arg Thr Ser Leu Pro Cys
1               5                   10                  15

Ile Pro Arg Glu Gln Leu Met Gly His Ser Glu Trp Asp His Lys Arg
                20                  25                  30

Gly Pro Arg Gly Ser Gln Ser Ser Gly Thr Ser Ile Thr Val Asp Ile
            35                  40                  45

Ala Val Met Gly Glu Ala His Gly Leu Ile Thr Asp Leu Leu Ala Asp
    50                  55                  60

Pro Ser Leu Pro Pro Asn Val Cys Thr Ser Leu Arg Ala Val Ser Asn
65                  70                  75                  80

Leu Leu Ser Thr Gln Leu Thr Phe Gln Ala Ile His Lys Pro Arg Val
                85                  90                  95

Asn Pro Val Thr Ser Leu Ser Glu Asn Tyr Thr Cys Ser Asp Ser Glu
                100                 105                 110

Glu Ser Ser Glu Lys Asp Lys Leu Ala Ile Pro Lys Arg Leu Arg Arg
            115                 120                 125

Ser Leu Pro Pro Gly Leu Leu Arg Arg Val Ser Ser Thr Trp Thr Thr
130                 135                 140

Thr Thr Ser Ala Thr Gly Leu Pro Thr Leu Glu Pro Ala Pro Val Arg
145                 150                 155                 160

Arg Asp Arg Ser Thr Ser Ile Lys Leu Gln Glu Ala Pro Ser Ser Ser
                165                 170                 175

Pro Asp Ser Trp Asn Asn Pro Val Met Met Thr Leu Thr Lys Ser Arg
            180                 185                 190

Ser Phe Thr Ser Ser Tyr Ala Ile Ser Ala Ala Asn His Val Lys Ala
        195                 200                 205

Lys Lys Gln Ser Arg Pro Gly Ala Leu Ala Lys Ile Ser Pro Leu Ser
    210                 215                 220
```

-continued

```
Ser Pro Cys Ser Ser Pro Leu Gln Gly Thr Pro Ala Ser Ser Leu Val
225                 230                 235                 240

Ser Lys Ile Ser Ala Val Gln Phe Pro Glu Ser Ala Asp Thr Thr Ala
            245                 250                 255

Lys Gln Ser Leu Gly Ser His Arg Ala Leu Thr Tyr Thr Gln Ser Ala
                260                 265                 270

Pro Asp Leu Ser Pro Gln Ile Leu Thr Pro Pro Val Ile Cys Ser Ser
            275                 280                 285

Cys Gly Arg Pro Tyr Ser Gln Gly Asn Pro Ala Asp Glu Pro Leu Glu
        290                 295                 300

Arg Ser Gly Val Ala Thr Arg Thr Pro Ser Arg Thr Asp Asp Thr Ala
305                 310                 315                 320

Gln Val Thr Ser Asp Tyr Glu Asn Asn Ser Asp Ser Ser Asp
                325                 330                 335

Ile Val Gln Asn Glu Asp Glu Thr Glu Cys Leu Arg Glu Pro Leu Arg
                340                 345                 350

Lys Ala Ser Ala Cys Ser Thr Tyr Ala Pro Glu Thr Met Met Phe Leu
            355                 360                 365

Asp Lys Pro Ile Leu Ala Pro Glu Pro Leu Val Met Asp Asn Leu Asp
        370                 375                 380

Ser Ile Met Glu Gln Leu Asn Thr Trp Asn Phe Pro Ile Phe Asp Leu
385                 390                 395                 400

Val Glu Asn Ile Gly Arg Lys Cys Gly Arg Ile Leu Ser Gln Val Ser
                405                 410                 415

Tyr Arg Leu Phe Glu Asp Met Gly Leu Phe Glu Ala Phe Lys Ile Pro
            420                 425                 430

Ile Arg Glu Phe Met Asn Tyr Phe His Ala Leu Glu Ile Gly Tyr Arg
        435                 440                 445

Asp Ile Pro Tyr His Asn Arg Ile His Ala Thr Asp Val Leu His Ala
    450                 455                 460

Val Trp Tyr Leu Thr Thr Gln Pro Ile Pro Gly Leu Ser Thr Val Ile
465                 470                 475                 480

Asn Asp His Gly Ser Thr Ser Asp Ser Asp Ser Asp Ser Gly Phe Thr
                485                 490                 495

His Gly His Met Gly Tyr Val Phe Ser Lys Thr Tyr Asn Val Thr Asp
            500                 505                 510

Asp Lys Tyr Gly Cys Leu Ser Gly Asn Ile Pro Ala Leu Glu Leu Met
        515                 520                 525

Ala Leu Tyr Val Ala Ala Ala Met His Asp Tyr Asp His Pro Gly Arg
    530                 535                 540

Thr Asn Ala Phe Leu Val Ala Thr Ser Ala Pro Gln Ala Val Leu Tyr
545                 550                 555                 560

Asn Asp Arg Ser Val Leu Glu Asn His His Ala Ala Ala Trp Asn
                565                 570                 575

Leu Phe Met Ser Arg Pro Glu Tyr Asn Phe Leu Ile Asn Leu Asp His
            580                 585                 590

Val Glu Phe Lys His Phe Arg Phe Leu Val Ile Glu Ala Ile Leu Ala
        595                 600                 605

Thr Asp Leu Lys Lys His Phe Asp Phe Val Ala Lys Phe Asn Gly Lys
    610                 615                 620

Val Asn Asp Asp Val Gly Ile Asp Trp Thr Asn Glu Asn Asp Arg Leu
625                 630                 635                 640

Leu Val Cys Gln Met Cys Ile Lys Leu Ala Asp Ile Asn Gly Pro Ala
```

```
                645                 650                 655
Lys Tyr Lys Glu Leu His Leu Gln Trp Thr Asp Gly Ile Val Asn Glu
            660                 665                 670

Phe Tyr Glu Gln Gly Asp Glu Glu Ala Ser Leu Gly Leu Pro Ile Ser
            675                 680                 685

Pro Phe Met Asp Arg Ser Ala Pro Gln Leu Ala Asn Leu Gln Glu Ser
            690                 695                 700

Phe Ile Ser His Ile Val Gly Pro Leu Cys Asn Ser Tyr Asp Ser Ala
705                 710                 715                 720

Gly Leu Met Pro Gly Lys Trp Val Glu Asp Ser Asp Glu Ser Gly Asp
            725                 730                 735

Thr Asp Asp Pro Glu Glu Glu Glu Glu Ala Pro Ala Pro Asn Glu
            740                 745                 750

Glu Glu Thr Cys Glu Asn Asn Glu Ser Pro Lys Lys Thr Phe Lys
            755                 760                 765

Arg Arg Lys Ile Tyr Cys Gln Ile Thr Gln His Leu Leu Gln Asn His
770                 775                 780

Lys Met Trp Lys Lys Val Ile Glu Glu Gln Arg Leu Ala Gly Ile
785                 790                 795                 800

Glu Asn Gln Ser Leu Asp Gln Thr Pro Gln Ser His Ser Ser Glu Gln
            805                 810                 815

Ile Gln Ala Ile Lys Glu Glu Glu Glu Lys Gly Lys Pro Arg Gly
            820                 825                 830

Glu Glu Ile Pro Thr Gln Lys Pro Asp Gln
            835                 840

<210> SEQ ID NO 3
<211> LENGTH: 658
<212> TYPE: PRT
<213> ORGANISM: Homo sapiens

<400> SEQUENCE: 3

Met Met Thr Leu Thr Lys Ser Arg Ser Phe Thr Ser Ser Tyr Ala Ile
1               5                  10                  15

Ser Ala Ala Asn His Val Lys Ala Lys Lys Gln Ser Arg Pro Gly Ala
                20                  25                  30

Leu Ala Lys Ile Ser Pro Leu Ser Pro Cys Ser Ser Pro Leu Gln
            35                  40                  45

Gly Thr Pro Ala Ser Ser Leu Val Ser Lys Ile Ser Ala Val Gln Phe
        50                  55                  60

Pro Glu Ser Ala Asp Thr Thr Ala Lys Gln Ser Leu Gly Ser His Arg
65                  70                  75                  80

Ala Leu Thr Tyr Thr Gln Ser Ala Pro Asp Leu Ser Pro Gln Ile Leu
                85                  90                  95

Thr Pro Pro Val Ile Cys Ser Ser Cys Gly Arg Pro Tyr Ser Gln Gly
            100                 105                 110

Asn Pro Ala Asp Glu Pro Leu Glu Arg Ser Gly Val Ala Thr Arg Thr
        115                 120                 125

Pro Ser Arg Thr Asp Asp Thr Ala Gln Val Thr Ser Asp Tyr Glu Thr
    130                 135                 140

Asn Asn Asn Ser Asp Ser Ser Asp Ile Val Gln Asn Glu Asp Glu Thr
145                 150                 155                 160

Glu Cys Leu Arg Glu Pro Leu Arg Lys Ala Ser Ala Cys Ser Thr Tyr
                165                 170                 175

Ala Pro Glu Thr Met Met Phe Leu Asp Lys Pro Ile Leu Ala Pro Glu
```

```
                    180             185             190
Pro Leu Val Met Asp Asn Leu Asp Ser Ile Met Glu Gln Leu Asn Thr
            195                 200                 205
Trp Asn Phe Pro Ile Phe Asp Leu Val Glu Asn Ile Gly Arg Lys Cys
            210                 215                 220
Gly Arg Ile Leu Ser Gln Val Ser Tyr Arg Leu Phe Glu Asp Met Gly
225                 230                 235                 240
Leu Phe Glu Ala Phe Lys Ile Pro Ile Arg Glu Phe Met Asn Tyr Phe
                245                 250                 255
His Ala Leu Glu Ile Gly Tyr Arg Asp Ile Pro Tyr His Asn Arg Ile
                260                 265                 270
His Ala Thr Asp Val Leu His Ala Val Trp Tyr Leu Thr Thr Gln Pro
            275                 280                 285
Ile Pro Gly Leu Ser Thr Val Ile Asn Asp His Gly Ser Thr Ser Asp
            290                 295                 300
Ser Asp Ser Asp Ser Gly Phe Thr His Gly His Met Gly Tyr Val Phe
305                 310                 315                 320
Ser Lys Thr Tyr Asn Val Thr Asp Asp Lys Tyr Gly Cys Leu Ser Gly
                325                 330                 335
Asn Ile Pro Ala Leu Glu Leu Met Ala Leu Tyr Val Ala Ala Ala Met
                340                 345                 350
His Asp Tyr Asp His Pro Gly Arg Thr Asn Ala Phe Leu Val Ala Thr
            355                 360                 365
Ser Ala Pro Gln Ala Val Leu Tyr Asn Asp Arg Ser Val Leu Glu Asn
            370                 375                 380
His His Ala Ala Ala Trp Asn Leu Phe Met Ser Arg Pro Glu Tyr
385                 390                 395                 400
Asn Phe Leu Ile Asn Leu Asp His Val Glu Phe Lys His Phe Arg Phe
                405                 410                 415
Leu Val Ile Glu Ala Ile Leu Ala Thr Asp Leu Lys Lys His Phe Asp
            420                 425                 430
Phe Val Ala Lys Phe Asn Gly Lys Val Asn Asp Asp Val Gly Ile Asp
            435                 440                 445
Trp Thr Asn Glu Asn Asp Arg Leu Leu Val Cys Gln Met Cys Ile Lys
            450                 455                 460
Leu Ala Asp Ile Asn Gly Pro Ala Lys Tyr Lys Glu Leu His Leu Gln
465                 470                 475                 480
Trp Thr Asp Gly Ile Val Asn Glu Phe Tyr Glu Gln Gly Asp Glu Glu
                485                 490                 495
Ala Ser Leu Gly Leu Pro Ile Ser Pro Phe Met Asp Arg Ser Ala Pro
                500                 505                 510
Gln Leu Ala Asn Leu Gln Glu Ser Phe Ile Ser His Ile Val Gly Pro
            515                 520                 525
Leu Cys Asn Ser Tyr Asp Ser Ala Gly Leu Met Pro Gly Lys Trp Val
            530                 535                 540
Glu Asp Ser Asp Glu Ser Gly Asp Thr Asp Asp Pro Glu Glu Glu Glu
545                 550                 555                 560
Glu Glu Ala Pro Ala Pro Asn Glu Glu Glu Thr Cys Glu Asn Asn Glu
                565                 570                 575
Ser Pro Lys Lys Lys Thr Phe Lys Arg Arg Lys Ile Tyr Cys Gln Ile
                580                 585                 590
Thr Gln His Leu Leu Gln Asn His Lys Met Trp Lys Lys Val Ile Glu
            595                 600                 605
```

```
Glu Gln Arg Leu Ala Gly Ile Glu Asn Gln Ser Leu Asp Gln Thr
        610                 615                 620

Pro Gln Ser His Ser Ser Glu Gln Ile Gln Ala Ile Lys Glu Glu
625                 630                 635                 640

Glu Glu Lys Gly Lys Pro Arg Gly Glu Glu Ile Pro Thr Gln Lys Pro
                645                 650                 655

Asp Gln

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 4
cttcatctct cacattgtgg ggcctctgtg                                    30

<210> SEQ ID NO 5
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 5
tttgcggccg cctcgagtta tttatcatca tcatctttat aatcctggtc tggcttttgg    60
gttgg                                                               65

<210> SEQ ID NO 6
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 6
ggaataatcc agtgctgctg accctcacca aaagcagatc c                        41

<210> SEQ ID NO 7
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 7
taatacgact cactataggg agtgaagagg gcaccctata ccatggcag                49

<210> SEQ ID NO 8
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 8
taatacgact cactataggg ttcagtctcc tgtgtgcctt cttctggatg              50

<210> SEQ ID NO 9
<211> LENGTH: 47
<212> TYPE: DNA
<213> ORGANISM: Artificial Sequence
<220> FEATURE:
<223> OTHER INFORMATION: Synthetic Oligonucleotide
```

<400> SEQUENCE: 9
taatacgact cactataggg gaagcgctcg tccagattgg gctgggc      47

<210> SEQ ID NO 10
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 10
taatacgact cactataggg tggagacctt acctggcgta cctggcc      47

<210> SEQ ID NO 11
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 11
taatacgact cactataggg actgcaggaa gcaccttcat ccagtcc      47

<210> SEQ ID NO 12
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 12
tttttttttt tttttttttt tcactggtct ggcttttggg ttggtat      47

<210> SEQ ID NO 13
<211> LENGTH: 457
<212> TYPE: DNA
<213> ORGANISM: Homo sapiens

<400> SEQUENCE: 13
tgatcgtttc tgcccgtgct tgttttcaac ttgagcgtgc tagcctttaa cttgaagaag       60
tctcattgga gcatctagca ttctccagga gttattcgaa agctgaaact ttcagtggat      120
tgtgggcctg gggagaagaa ggattccgag ggtggaattg ggaagagcgt gcgtgcgtgt      180
gtgtgtgtgt gtgtgtgcgc gcgcgcgtgg gtcggggcgg gggcgtcggg gggccactgg      240
gaattcagtg aagagggcac cctataccat ggcagtgccc ggcgacgctg cacgagtcag      300
gaacaagccc gtccacagtg gggtgagtca agccccacg gcgggccggg actgccacca       360
tcgtgcggac cccgcatcgc cgcgggactc gggctgccgt ggctgctggg gagacctggt      420
gctgcagccg ctccggagct ctcggaaact ttccctg                             457

<210> SEQ ID NO 14
<211> LENGTH: 4606
<212> TYPE: DNA
<213> ORGANISM: Homo sapiens

<400> SEQUENCE: 14
atggcagtgc ccggcgacgc tgcacgagtc aggaacaagc ccgtccacag tggggtgagt       60
caagccccca ggcgggccg ggactgccac catcgtgcgg accccgcatc gccgcgggac       120
tcgggctgcc gtggctgctg gggagacctg gtgctgcagc cgctccggag ctctcggaaa      180
ctttcctccg cgctgtgcgc gggctgccta tcctttctgc tggcgctgct ggtgaggctg      240

```
gtccgcgggg aggtcggctg tgacctggag cagtgtaagg aggcggcggc ggcggaggag      300
gaggaagcag ccccgggagc agaaggggcc gtcttcccgg ggcctcgggg aggtgctccc      360
gggggcggtg cgcggctcag ccoctggctg cagccctcgg cgctgctctt cagtctcctg      420
tgtgccttct tctggatggg cttgtacctc ctgcgcgccg gggtgcgcct gcctctggct      480
gtcgcgctgc tggccgcctg ctgcgggggg aagcgctcg tccagattgg gctgggcgtc       540
ggggaggatc acttactctc actccccgcc gcggggtgg tgctcagctg cttggccgcc       600
gcgacatggc tggtgctgag gctgaggctg ggcgtcctca tgatcgcctt gactagcgcg      660
gtcaggaccg tgtccctcat ttccttagag aggttcaagg tcgcctggag accttacctg      720
gcgtacctgg ccggcgtgct ggggatcctc ttggccaggt acgtggaaca aatcttgccg      780
cagtccgcgg aggcggctcc aagggagcat ttggggtccc agctgattgc tgggaccaag      840
gaagatatcc cggtgtttaa gaggaggagg cggtccagct ccgtcgtgtc cgccgagatg      900
tccggctgca gcagcaagtc ccatcggagg acctccctgc cctgtatacc gagggaacag      960
ctcatggggc attcagaatg ggaccacaaa cgagggccaa gaggatcaca gtcttcagga     1020
accagtatta ctgtggacat cgccgtcatg ggcgaagcca cggcctcatt accgacctcc     1080
tggcagaccc ttctcttcca ccaaacgtgt gccacatcct tgagagccgt gagcaacttg     1140
ctcagcacac agctcacctt ccaggccatt cacaagccca gagtgaatcc cgttacttcg     1200
ctcagtgaaa actatacctg ttctgactct gaagagagct ctgaaaaaga caagcttgct     1260
attccaaagc gcctgagaag gagtttgcct cctggcttgt tgagacgagt tcttccact      1320 tggaccacca ccacctcggc cacaggtcta cccaccttgg agcctgcacc agtacggaga     1380
gaccgcagca ccagcatcaa actgcaggaa gcaccttcat ccagtcctga ttcttggaat     1440
aatccagtga tgatgacccct caccaaaagc agatcctta cttcatccta tgctatttct      1500
gcagctaacc atgtaaaggc taaaaagcaa agtcgaccag gtgccctcgc taaaatttca     1560 cctcttttcat cgccctgctc ctcacctctc caagggactc ctgccagcag cctggtcagc     1620
aaaatttctg cagtgcagtt tccagaatct gctgacacaa ctgccaaaca agcctaggt     1680 tctcacaggg ccttaactta cactcagagt gccccagacc tatcccctca aatcctgact     1740
ccacctgtta tatgtagcag ctgtggcaga ccatattccc aagggaatcc tgctgatgag     1800
cccctggaga gaagtggggt agccactcgg acaccaagtc gaacagatga cactgctcaa     1860
gttacctctg attatgaaac caataacaac agtgacagca gtgacattgt acagaatgaa     1920
gatgaaacag agtgcctgag agagcctctg aggaaagcat cggcttgcag cacctatgct     1980
cctgagacca tgatgtttct ggacaaacca attcttgctc ccgaacctct tgtcatggat     2040
aacctggact caattatgga gcagctaaat acttggaatt ttccaatttt tgatttagtg     2100
gaaaatatag aagaaaatg tggccgtatt cttagtcagg tatcttacag acttttgaa      2160 gacatgggcc tctttgaagc ttttaaaatt ccaattaggg aatttatgaa ttatttcat      2220 gctttgagag ttggatatag ggatattcct tatcataaca gaatccatgc cactgatgtt     2280
ttacatgctg tttggtatct tactacacag cctattccag gcctctcaac tgtgattaat     2340
gatcatggtt caaccagtga ttcagattct gacagtggat ttacacatgg acatatggga     2400
tatgtattct caaaaacgta taatgtgaca gatgataaat acggatgtct gtctgggaat     2460
atccctgcct tggagttgat ggcgctgtat gtggctgcag ccatgcacga ttatgatcat     2520
ccaggaagga ctaatgcttt cctggttgca actagtgctc ctcaggcggt gctatataac     2580
gatcgttcag ttttggagaa tcatcacgca gctgctgcat ggaatctttt catgtcccgg     2640
```

```
ccagagtata acttcttaat taaccttgac catgtggaat ttaagcattt ccgtttcctt    2700
gtcattgaag caattttggc cactgacctg aagaaacact ttgacttcgt agccaaattt    2760
aatggcaagg taaatgatga tgttggaata gattggacca atgaaaatga tcgtctactg    2820
gtttgtcaaa tgtgtataaa gttggctgat atcaatggtc cagctaaatg taaagaactc    2880
catcttcagt ggacagatgg tattgtcaat gaattttatg aacagggtga tgaagaggcc    2940
agccttggat tacccataag ccccttcatg gatcgttctg ctcctcagct ggccaacctt    3000
caggaatcct tcatctctca cattgtgggg cctctgtgca actcctatga ttcagcagga    3060
ctaatgcctg gaaatgggt ggaagacagc gatgagtcag gagatactga tgacccagaa     3120
gaagaggagg aagaagcacc agcaccaaat gaagaggaaa cctgtgaaaa taatgaatct    3180
ccaaaaaaga agactttcaa aaggagaaaa atctactgcc aaataactca gcacctctta    3240
cagaaccaca agatgtggaa gaaagtcatt gaagaggagc aacggttggc aggcatagaa    3300
aatcaatccc tggaccagac ccctcagtcg cactcttcag aacagatcca ggctatcaag    3360
gaagaagaag aagagaaagg gaaccaaga ggcgaggaga taccaaccca aaagccagac     3420
cagtgacaat ggatagaatg ggctgtgttt ccaaacagat tgacttgtca aagactctct    3480
tcaagccagc acaagcattt agatcacaac actgtagaaa tttgagatgg caaatggct    3540
attgcattt gggattcttc gcattttgtg tgtatatttt tacagtgagg tacattgtta    3600
aaaactttt gctcaaagaa gctttcacat tgcaacacca gcttctaagg attttttaag    3660
gagggaatat atatgtgtgt gtgtatataa gctcccacat agatacatgt aaaacatatt    3720
cacacccatg cacgcacaca catacacact gaaggccacg attgctggct ccacaattta    3780
gtaacattta tattaagata tatatatagt ggtcactgtg atataataaa tcataaagga    3840
aaccaaatca caaggagat ggtgtggctt agcaaggaaa cagtgcagga aatgtaggtt     3900
accaactaag cagcttttgc tcttagtact gagggatgaa agttccagag cattatttga    3960
attctgatac atcctgccaa cactgtgtgt gtgtgtgtgt gtgtgtgtgt gtgtgtgtgt    4020
gtgtgtgaaa gagagacaga agggatggtt tgagagggg cgcttgtgtg catgtgtgtg     4080
ctatatgtaa agagatttt gtggtttaag taactcagaa tagctgtagc aaatgactga     4140
atacatgtga acaaacagaa ggaagttcac tctggagtgt ctttgggagg caggctattc    4200
caaatgccct cgtcgattta gcttcaataa agggcttttt gctggtggag ggcactcaag    4260
ggctcctca gagggccacg tgtttggtat tacattactg ctatgcacca cttgaaggag     4320
ctctatcacc agcctgaaac ccgaagactg aggcatttc caggtctact tgcctaatga     4380
atgtatagga actgtctatg agtatggatg tcactcaact aagatcaaat caccatttaa    4440
gggggatggc attctttata cctaaacacc taagagctga agtcaggtct tttaatcagg    4500
ttagaattct aaatgatgcc agagaaggct tgggaaattg tacttcaggg tgatagcctg    4560
tgtcttctta atttactggg aaatatgtgg tagagaaagg aaagga                  4606
```

<210> SEQ ID NO 15
<211> LENGTH: 4306
<212> TYPE: DNA
<213> ORGANISM: Homo sapiens

<400> SEQUENCE: 15

```
gaggaagcag ccccgggagc agaaggggcc gtcttcccgg ggcctcgggg aggtgctccc      60
gggggcggtg cgcggctcag cccctggctg cagcccctcgg cgctgctctt cagtctcctg    120
tgtgccttct tctggatggg cttgtacctc ctgcgcgccg gggtgcgcct gcctctggct    180
```

```
gtcgcgctgc tggccgcctg ctgcgggggg gaagcgctcg tccagattgg gctgggcgtc    240
ggggaggatc acttactctc actccccgcc gcggggtgg tgctcagctg cttggccgcc    300
gcgacatggc tggtgctgag gctgaggctg ggcgtcctca tgatcgcctt gactagcgcg    360
gtcaggaccg tgtccctcat ttccttagag aggttcaagg tcgcctggag accttacctg    420
gcgtacctgg ccggcgtgct ggggatcctc ttggccaggt acgtggaaca aatcttgccg    480
cagtccgcgg aggcggctcc aagggagcat ttggggtccc agctgattgc tgggaccaag    540
gaagatatcc cggtgtttaa gaggaggagg cggtccagct ccgtcgtgtc cgccgagatg    600
tccggctgca gcagcaagtc ccatcggagg acctccctgc cctgtatacc gagggaacag    660
ctcatggggc attcagaatg ggaccacaaa cgagggccaa gaggatcaca gtcttcagga    720
accagtatta ctgtggacat cgccgtcatg ggcgaagcca cggcctcatt accgacctcc    780
tggcagaccc ttctcttcca ccaaacgtgt gccacatcct tgagagccgt gagcaacttg    840
ctcagcacac agctcacctt ccaggccatt cacaagccca gagtgaatcc cgttacttcg    900
ctcagtgaaa actatacctg ttctgactct gagagagct ctgaaaaaga caagcttgct    960
attccaaagc gcctgagaag gagtttgcct cctggcttgt tgagacgagt tcttccact   1020 tggaccacca ccacctcggc cacaggtcta cccaccttgg agcctgcacc agtacggaga   1080
gaccgcagca ccagcatcaa actgcaggaa gcaccttcat ccagtcctga ttcttggaat   1140
aatccagtga tgatgaccct caccaaaagc agatccttta cttcatccta tgctatttct   1200
gcagctaacc atgtaaaggc taaaaagcaa agtcgaccag gtgccctcgc taaaatttca   1260 cctcttttcat cgccctgctc ctcacctctc caagggactc ctgccagcag cctggtcagc   1320
aaaatttctg cagtgcagtt tccagaatct gctgacacaa ctgccaaaca aagcctaggt   1380
tctcacaggg ccttaactta cactcagagt gccccagacc tatcccctca atcctgact   1440 ccacctgtta tatgtagcag ctgtggcaga ccatattccc aagggaatcc tgctgatgag   1500
cccctggaga gaagtggggt agccactcgg acaccaagtc gaacagatga cactgctcaa   1560
gttacctctg attatgaaac caataacaac agtgacagca gtgacattgt acagaatgaa   1620
gatgaaacag agtgcctgag agagcctctg aggaaagcat cggcttgcag cacctatgct   1680
cctgagacca tgatgtttct ggacaaacca attcttgctc ccgaacctct tgtcatggat   1740
aacctggact caattatgga gcagctaaat acttggaatt ttccaatttt tgatttagtg   1800
gaaaatatag gaagaaaatg tggccgtatt cttagtcagg tatcttacag actttttgaa   1860
gacatgggcc tctttgaagc ttttaaaatt ccaattaggg aatttatgaa ttattttcat   1920
gctttggaga ttggatatag ggatattcct tatcataaca gaatccatgc cactgatgtt   1980
ttacatgctg tttggtatct tactacacag cctattccag gcctctcaac tgtgattaat   2040
gatcatggtt caaccagtga ttcagattct gacagtggat ttacacatgg acatatggga   2100
tatgtattct caaaaacgta taatgtgaca gatgataaat acggatgtct gtctgggaat   2160
atccctgcct ggagttgat ggcgctgtat gtggctgcag ccatgcacga ttatgatcat   2220
ccaggaagga ctaatgcttt cctggttgca actagtgctc ctcaggcggt gctatataac   2280
gatcgttcag ttttggagaa tcatcacgca gctgctgcat ggaatctttt catgtcccgg   2340
ccagagtata acttcttaat taaccttgac catgtggaat ttaagcattt ccgtttcctt   2400
gtcattgaag caattttggc cactgacctg aagaaacact ttgacttcgt agccaaattt   2460 aatgcaagg taaatgatga tgttggaata gattggacca atgaaaatga tcgtctactg   2520
gtttgtcaaa tgtgtataaaa gttggctgat atcaatggtc cagctaaatg taaagaactc   2580
```

```
catcttcagt ggacagatgg tattgtcaat gaattttatg aacagggtga tgaagaggcc    2640
agccttggat tacccataag ccccttcatg gatcgttctg ctcctcagct ggccaacctt    2700
caggaatcct tcatctctca cattgtgggg cctctgtgca actcctatga ttcagcagga    2760
ctaatgcctg gaaatgggt ggaagacagc gatgagtcag gagatactga tgacccagaa     2820
gaagaggagg aagaagcacc agcaccaaat gaagaggaaa cctgtgaaaa taatgaatct    2880 ccaaaaaga agactttcaa aaggagaaaa atctactgcc aaataactca gcacctctta     2940
cagaaccaca agatgtggaa gaaagtcatt gaagaggagc aacggttggc aggcatagaa    3000
aatcaatccc tggaccagac ccctcagtcg cactcttcag aacagatcca ggctatcaag    3060
gaagaagaag aagagaaagg gaaaccaaga ggcgaggaga taccaaccca aaagccagac    3120
cagtgacaat ggatagaatg ggctgtgttt ccaaacagat tgacttgtca aagactctct    3180
tcaagccagc acaagcattt agatcacaac actgtagaaa tttgagatgg caaatggct     3240 attgcatttt gggattcttc gcattttgtg tgtatatttt tacagtgagg tacattgtta    3300 aaaactttt gctcaaagaa gctttcacat tgcaacacca gcttctaagg atttttaag      3360 gagggaatat atatgtgtgt gtgtatataa gctcccacat agatacatgt aaaacatatt    3420
cacacccatg cacgcacaca catacacact gaaggccacg attgctggct ccacaattta    3480
gtaacattta tattaagata tatatatagt ggtcactgtg atataataaa tcataaagga    3540
aaccaaatca caaggagat ggtgtggctt agcaaggaaa cagtgcagga atgtaggtt      3600 accaactaag cagcttttgc tcttagtact gagggatgaa agttccagag cattatttga    3660
attctgatac atcctgccaa cactgtgtgt gtgtgtgtgt gtgtgtgtgt gtgtgtgtgt    3720
gtgtgtgaaa gagagacaga agggatggtt tgagagggggt cgcttgtgtg catgtgtgtg   3780
ctatatgtaa agagattttt gtggtttaag taactcagaa tagctgtagc aaatgactga    3840
atacatgtga acaaacagaa ggaagttcac tctggagtgt cttttggagag caggctattc   3900 caaatgccct cgtcgattta gcttcaataa agggcctttt gctggtggag ggcactcaag    3960
ggctccctca gagggccacg tgtttggtat tacattactg ctatgcacca cttgaaggag    4020
ctctatcacc agcctgaaac ccgaagactg aggcatttc caggtctact tgcctaatga    4080
atgtatagga actgtctatg agtatggatg tcactcaact aagatcaaat caccatttaa    4140
gggggatggc attctttata cctaaacacc taagagctga agtcaggtct tttaatcagg    4200
ttagaattct aaatgatgcc agagaaggct tgggaaattg tacttcaggg tgatagcctg    4260
tgtcttctta atttactggg aaatatgtgg tagagaaagg aaagga                   4306

<210> SEQ ID NO 16
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 16
tgatcgtttc tgcccgtgct tgttttc                                           27

<210> SEQ ID NO 17
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 17
```

```
cagggaaagt tccgagagc tccggag                                             27

<210> SEQ ID NO 18
<211> LENGTH: 1890
<212> TYPE: DNA
<213> ORGANISM: Homo sapiens

<400> SEQUENCE: 18
ctagatccca gggaacatca atagagttta agtccattga acagatactg aattcttttt       60
cataatctgc caaaaaaagg ttagcttgaa aattttcttt tagtttctca aatatcacac      120
tgctgcagta cacgaacctt tactcattaa taactaaggt cctgattttt ttcatatgct      180
ttgctcgaag atgtagtatt tgcagccat agacagtctt ctaagatctc tcctagtgtt       240
aaccacctat gctcacctct cccttgagat tttctttat tttttgatga actatctggg       300
cttttaaact tgttaacct tttttgagga tacggtcact taatctcaat gtaattttac        360
tttccacagt caaaaactat tgtgaatact catgcactgg atttaaatga ctgctgcctc      420
tccttccttt cttttatac tattgtggtc taggtaaggc tgattcttcc atcatttgaa       480
ccaacaggcc aggcttgggt tctcataaag cagaccttcc agcaggagcg accaaaggat      540
gacactgtca cctgaaattg gactgctgtt gtacctgact tgggaacatc tttgaatcag      600
acagtagaag tggctgtcat ttcagggac agtagaaagt atgttggctc tcatctgcca       660
agtaggcaaa cacaatcttt tttttttttt tttccttcca acgttctagg gagctcagcc      720
tcagggctag ccgcagcccc ccacaccccg gggctgcggt gggctgcgcg gtggatcaac      780
ctcagcagcc cctgctccag cctgtagggt gaaccggccg cttcccagc aaaggagcaa       840 tcgagctgag ggtagcgcct cctccgcagg aggggcggg agctcggctg agaaagcttt       900
cctagggagt tgccttaaag aaagaaagcg gaattgtcga tcactccagt tgccagtttt      960
atacaatttt aagcagtcgt cgccactcgt ttcccctttg caaaactgca atcaccacc      1020 aaccttgcat caaatagaag tggggaggga aaaaaaaagc aaatctcctt ctcccttctc     1080
accctccctt tcttctcacc ctcccttcct ctcttactcg ctccttctcc ctccctccct     1140
tctgcggctg ccgctagtct ctcggtcctg gctctctctc cgacgggact tagcaacttc     1200
ttatttctca gccccttgtc attttttttt ttccatcctt tgccatgaat tggattgaca     1260
gaggcggggg aggcttttgct ttctagccca gggaatggcg atcgcgtcct ggggccgtgc    1320
ggggagaacg gcagaggaga aagaaagagt gatagaaaaa gagctgcagg aaggaggaga     1380
aggagacctc catctacctg cgggcccggc gcgctgcagc gcacgcagcg cgacgtgcgc     1440
ctcggaatgg cccggagccc gccctgcgcc ccggctcctc cagcgtcagc ggctcctgcg     1500
cgcgggatgc attgggcaat ttttgaaatc ctgaagtagg aagagacccc ggaggataga     1560 agtcggggt gggggtggag cagagaatct gtgaaagata ttcaaagaga aaagggaat      1620 cctgatcctt tctgcccgtg cttgttttca acttgagcgt gctagccttt aacttgaaga     1680
agtctcattg gagcatctag cattctccag gagttattcg aaagctgaaa ctttcagtgg     1740
attgtgggcc tggggagaag aaggattccg agggtgaat tggaagagc gtgcgtgcgt       1800 gtgtgtgtgt gtgtgtgtgc gcgcgcgcgt gggtcggggc gggggcgtcg gggggccact     1860
gggaattcag tgaagagggc accctatacc                                    1890
```

ISOFORM-SELECTIVE INHIBITORS AND ACTIVATORS OF PDE3 CYCLIC NUCLEOTIDE PHOSPHODIESTERASES

CROSS-REFERENCE TO RELATED APPLICATIONS

This application is a divisional of U.S. patent application Ser. No. 10/175,161, filed Jun. 19, 2002, now abandoned, which application claims the benefit under 35 U.S.C. §119(e) of U.S. Provisional Patent Application Ser. No. 60/309,271, filed Aug. 1, 2001, the disclosure of each of which is hereby incorporated herein by this reference in its entirety.

STATEMENT REGARDING FEDERALLY SPONSORED RESEARCH OR DEVELOPMENT

The invention described herein was made with Government support under Merit Review and Career Development Enhancement Awards from the Department of Veterans Affairs. The Federal Government has certain rights in the invention.

BACKGROUND OF THE INVENTION

1. Field of the Invention

The present invention relates to the field of cardiovascular and other diseases. More particularly, the present invention concerns compositions and methods of identification and use of isoform-selective activators or inhibitors of type 3 phosphodiesterase (PDE3). Other embodiments of the invention concern high-throughput screening for novel pharmaceuticals directed against PDE3 isoforms. In certain embodiments, the compositions and methods disclosed herein are of use for treatment of cardiomyopathy, pulmonary hypertension and related conditions.

2. Description of Related Art

PDE3 cyclic nucleotide phosphodiesterases hydrolyze cAMP and cGMP and thereby modulate cAMP- and cGMP-mediated signal transduction (Shakur et al., 2000a). These enzymes have a major role in the regulation of contraction and relaxation in cardiac and vascular myocytes. PDE3 inhibitors, which raise intracellular cAMP and cGMP content, have inotropic effects attributable to the activation of cAMP-dependent protein kinase (PK-A) in cardiac myocytes and vasodilatory effects attributable to the activation of cGMP-dependent protein kinase (PK-G) in vascular myocytes (Shakur et al., 2000a). When used in the treatment of dilated cardiomyopathy, PDE3 inhibitors such as milrinone, enoximone and aminone initially elicit favorable hemodynamic responses, but long-term administration increases mortality by up to 40% (Nony et al., 1994). This linkage of short-term benefits of PDE3 inhibition to deleterious effects on long-term survival in dilated cardiomyopathy is one of the most perplexing problems in cardiovascular therapeutics. However, it is thought that these biphasic effects reflect the compartmentally nonselective increases in intracellular cAMP content in cardiac myocytes current inhibitors display.

Clinical trials of the use of β-adrenergic receptor agonists, which, like PDE3 inhibitors, increase intracellular cAMP content in cardiac myocytes, were terminated prior to completion because of increased mortality in treated patients, while β-adrenergic receptor antagonists, which reduce intracellular cAMP content, have been shown to improve long-term survival despite initially adverse hemodynamic effects. These findings suggest that both the short-term benefits and long-term adverse effects of PDE3 inhibition are attributable to increases in intracellular cAMP content in cardiac myocytes (Movsesian, 1999).

The contradictory effects of nonspecific PDE3 antagonists may relate to the diverse intracellular processes regulated by cAMP in cardiac and vascular cells. Upon activation by cAMP, PK-A phosphorylates dozens of proteins in separate intracellular compartments that are involved in contraction and relaxation, glycogen metabolism, gene transcription, intracellular $Ca^{2+}$ cycling and signal autoregulation. Phosphorylation of cAMP-response element-binding protein (CREB), for example, activates the transcription of genes containing cAMP response elements (Shaywitz and Greenberg, 1999). Transgenic mice expressing a dominant non-phosphorylatable CREB in cardiac myocytes develop a dilated cardiomyopathy that very closely resembles the human disease (Fentzke et al., 1998), suggesting that CREB phosphorylation may be desirable in dilated cardiomyopathy.

Another example of cAMP effects is the phosphorylation of phospholamban, which relieves its inhibition of SERCA2, the $Ca^{2+}$-transporting ATPase of the sarcoplasmic reticulum (Simmerman and Jones, 1998). Ablation of phospholamban in muscle LIM protein $(MLP)^{-/-}$ mice with dilated cardiomyopathy results in the restoration of normal chamber size and contractility (Minamisawa et al., 1999), suggesting that phospholamban phosphorylation may also be beneficial in cardiomyopathy.

Other substrates phosphorylated by PK-A may contribute to adverse effects on long-term survival. Phosphorylation of L-type $Ca^{2+}$ channels increases their open probability and may be arrhythmogenic (Fischmeister and Hartzell, 1990), while phosphorylation of proteins in the mitogen-activated protein kinase (MAP kinase) cascade may alter myocardial gene transcription so as to speed the progression of the disease (Cook and McCormick, 1993; Lazou et al., 1994).

Raising cAMP content in cardiac myocytes via mechanisms such as activation of $β_1$-adrenergic, $β_2$-adrenergic or prostaglandin receptors or non-selective phosphodiesterase inhibition by isobutylmethylxanthine, affects cAMP content differentially in intracellular compartments represented in cytosolic and microsomal fractions of cardiac muscle, resulting in different patterns of protein phosphorylation and different physiologic responses (Hayes et al., 1980; Xiao and Lakatta, 1993; Xiao et al., 1994; Rapundalo et al., 1989; Jurevicius and Fischmeister, 1996). These considerations are particularly relevant to the pathophysiology of dilated cardiomyopathy, in which receptor-mediated and receptor-independent reductions in cAMP generation are prominent features (Movsesian, 1999; Lutz, et al., 2001). Comparison of cytosolic cAMP content in cytosolic and microsomal fractions between failing and non-failing hearts shows greater reduction in cAMP content in microsomal fractions of failing myocardium than in cytosolic fractions (Bohm, 1994).

The phosphorylation of individual substrates of PK-A may be differentially regulated in response to extracellular signals. Evidence for differential regulation comes from experiments examining the effects of stimulating adenylate cyclase activity and cAMP formation via $β_1$-adrenergic, $β_2$-adrenergic or PGE1 receptors. Activation of β-adrenergic receptors increases cAMP content in both cytosolic and microsomal fractions of cardiac myocytes and elicits contractile responses, while activation of PGE1 receptors increases cytosolic but not microsomal cAMP content and evokes no contractile response (Hayes et al., 1980; Buxton and Brunton, 1983). Increases in the amplitude of intracellular $Ca^{2+}$ transients in response to $β_1$-adrenergic receptor activation correlate with changes in microsomal cAMP content and are accompanied by increases in phospholamban phosphorylation. Conversely, activation of $\beta_2$-adrenergic receptors results in an increase in the amplitude of intracellular $Ca^{2+}$ transients that does not correlate with changes in microsomal cAMP content and occurs without increases in phospholamban phosphorylation (Hohl and Li, 1991; Xiao et al., 1993, 1994). Thus, activation of different receptors linked to cAMP metabolism can elicit different responses in cardiac tissues.

$\beta$-adrenergic receptor stimulation and nonselective phosphodiesterase inhibition have different effects on cAMP-activated protein phosphorylation in cardiac myocytes (Rapundalo et al., 1989; Jurvicius and Fischmeister, 1996) that are relevant to the pathophysiology of dilated cardiomyopathy. In that condition, a down-regulation of $\beta_1$-adrenergic receptors and an uncoupling of $\beta$-adrenergic receptor occupancy and adenylate cyclase stimulation (attributable to increases in $\beta$-adrenergic receptor kinase, G$\alpha$i and nucleoside diphosphate kinase) contribute to an impairment in cAMP generation (Movsesian, 1999; Lutz et al., 2001). Studies of cAMP content in cytosolic and microsomal fractions of failing and non-failing hearts demonstrate a far greater reduction in cAMP content in microsomal fractions than in cytosolic fractions of failing myocardium (Bohm et al., 1994). Taken together, these results indicate that cAMP content in different intracellular compartments can be selectively regulated to invoke different responses reflecting the phosphorylation of different substrates of PK-A. Further, this regulation is altered in dilated cardiomyopathy.

Different isoforms of PDE3 are expressed in cardiac and vascular myocytes and are localized to different intracellular compartments. The different PDE3 isoforms may differ in their regulation by PK-A and PK-B (protein kinase B, also known as Akt). PK-B, a downstream effector of insulin-like growth factors, is an anti-apoptotic mediator in cardiac myocytes (Fujio et al., 2000; Matsui et al., 1999; Wu et al., 2000). PK-B may also be involved in proliferative responses in vascular myocytes (Rocic and Lucchesi, 2001; Duan et al., 2000; Sandirasegarane et al., 2000). These findings suggest that different PDE3 isoforms may be involved in cell- and compartment-selective responses to different signals that have been implicated in the pathophysiology of dilated cardiomyopathy and/or pulmonary hypertension. Different PDE3 isoforms in cardiac and vascular myocytes may regulate functionally distinct pools of cAMP and cGMP involved in the phosphorylation of different substrates of PK-A and PK-G, and these isoforms may be regulated in response to different extracellular signals.

Until the present invention, it was not possible to develop isoform-selective inhibitors or activators of PDE3 to use in the treatment of cardiomyopathy and/or pulmonary hypertension. Isoform-selective PDE3 inhibitors may provide a beneficial effect on cardiac output without the long-term mortality associated with non-specific PDE3 inhibitors. Isoform-selective PDE3 activators may have beneficial anti-apoptotic effects in patients with dilated cardiomyopathy and/or pulmonary hypertension whose hemodynamic status is not too compromised to tolerate a reduction in cardiac contractility, without concomitant arrhythmogenic effects attributable to increases in cytosolic cAMP content. A paradigm for the latter is the use of $\beta$-adrenergic receptor antagonists in the treatment of dilated cardiomyopathy.

SUMMARY OF THE INVENTION

Agents capable of selectively activating or inhibiting individual PDE3 isoforms or of disrupting their intracellular localization may selectively affect the phosphorylation of smaller subsets of PK-A and PK-G substrates to therapeutic advantage. Without wishing to be limited to any one specific embodiment, an agent that selectively inhibits sarcoplasmic reticulum-associated PDE3A-136 may help to preserve intracellular $Ca^{2+}$ cycling and contractility in patients with dilated cardiomyopathy taking $\beta$-adrenergic receptor agonists, which may reduce arrhythmogenic effects attributable to increases in cytosolic cAMP content. Alternatively, if the activation of PDE3A-136 by PK-B is anti-apoptotic in cardiac myocytes, its inhibition may be pro-apoptotic (possibly explaining the increased long-term mortality seen with PDE3 inhibition in dilated cardiomyopathy), and the selective activation of this isoform may be desirable. In addition, currently available competitive PDE3 inhibitors inhibit cAMP activity more potently than they inhibit cGMP hydrolytic activity, owing to the higher Kms of the hydrolytic enzymes for cAMP than for cGMP. Agents that inhibit PDE3 activity through other mechanisms, identified by the methods described herein, may affect hydrolysis of the two substrates differentially, resulting in different cellular actions of therapeutic benefit.

As disclosed herein, N-terminal differences exist between the different isoforms of PDE3. Without wishing to be limited to any one specific embodiment, these N-terminal differences may offer opportunities for targeting individual isoforms of PDE3. Differences with respect to phosphorylation sites that stimulate catalytic activity suggest that agents that bind to domains containing these sites so as to either block phosphorylation or mimic its effects may be useful as isoform-selective PDE3 inhibitors or activators. As an example, an agent that binds to the P1 phosphorylation site could selectively inhibit or activate PDE3A-136 or PDE3B-137. A similar rationale would apply to agents that bind to N-terminal protein-interacting domains so as to either block or mimic the effects of these interactions, with the paradigm of peptides that modulate cAMP-mediated signaling by blocking PK-A/ AKAP interactions (Rosenmund, et al., 1994). Without wishing to be limited to any one specific embodiment, the typical accessibility of phosphorylation sites and protein-interacting domains makes them propitious drug targets. Differences between PDE3A and PDE3B in the N-terminal regions are sufficient to permit selective targeting of PDE3A-136 v. PDE3B-137, which may allow selective modulation of PDE3 activity in cardiac and vascular myocytes.

As shown herein, the different isoforms of PDE3 are translated from different mRNAs. In some cases, these mRNAs are generated from different genes (PDE3A and PDE3B). In the case of PDE3A, different isoforms are generated from different mRNAs transcribed from the same gene (e.g., PDE3A1 and PDE3A2 mRNAs). The open reading frame (ORF) of PDE3A1 is indicated in SEQ ID NO:14. The 5' untranslated region (5'-UTR) of PDE3A1, starting with the first ATG codon, is listed in SEQ ID NO:18. The approximate ORF of PDE3A2 is indicated in SEQ ID NO:15. A nucleotide sequence unique to PDE3A1 mRNA has been identified, and cDNA probes have been designed that react with PDE3A1 mRNA but not PDE3A2 mRNA. Without wishing to be limited to any one specific embodiment, these differences make PDE3 mRNAs propititious targets for decreasing the activity of individual protein isoforms by inhibiting the translation of their mRNAs via antisense constructs, ribozymes or small interfering RNAs ("siRNAs").

The present invention fulfills an unresolved need in the art by identifying differences between PDE3 isoforms that may be used to develop isoform-selective inhibitors or activators of PDE3 activity. Such inhibitors or activators are proposed to allow the differential regulation of cAMP and cGMP levels in different subcellular compartments, cell types and tissues. In certain embodiments, the present invention concerns methods for identifying isoform-selective PDE3 inhibitors or activators. Certain embodiments concern compounds identified by such methods that are of use for the therapeutic treatment of cardiomyopathy and/or pulmonary hypertension. In preferred embodiments, such compounds result in improved cardiac output while exhibiting little or no long-term toxicity. In other embodiments, the isoform-selective inhibitors or activators of PDE3 find utility for therapeutic treatment of a number of disease states related to defects in the regulation of cAMP concentration, such as diabetes mellitus, peripheral vascular disease and coronary artery stenosis (especially, but not limited to, stenoses occurring after coronary angioplasty).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A: Western blotting of rtPDE3A1 (containing the full ORF product of PDE3A1) and microsomal and cytosolic fractions of human myocardium. A lysate of Sf21 cells expressing a full-length open reading frame ORF of rePDE3A1 (1.0 µg/lane) and microsomal and cytosolic fractions of human myocardium (50 and 20 µg/lane, respectively) were subjected to SDS-PAGE, followed by electrophoretic transfer to nitrocellulose membranes and Western blotting, using anti-NT, anti-MID and anti-CT antibodies.

FIG. 5B: Location of anti-NT, anti-MD and Anti-CT binding sites on the full-length ORF of PDE3A1.

FIG. 11: Open reading frame of PDE3A (see SEQ ID NO:14). The apparent N-terminal methionine residues of the three isoforms are indicated in bold for PDE3A-136 (amino acid 146), PDE3A-118 (amino acid 300) and PDE3A-94 (amino acids 484 or 485). The phosphorylation sites on the PDE3A isoforms are indicated by underlining for P1 (amino acids 288-294), P2 (amino acids 309-312) and P3 (amino acids 435-438).

DETAILED DESCRIPTION OF THE INVENTION

Figure 1:
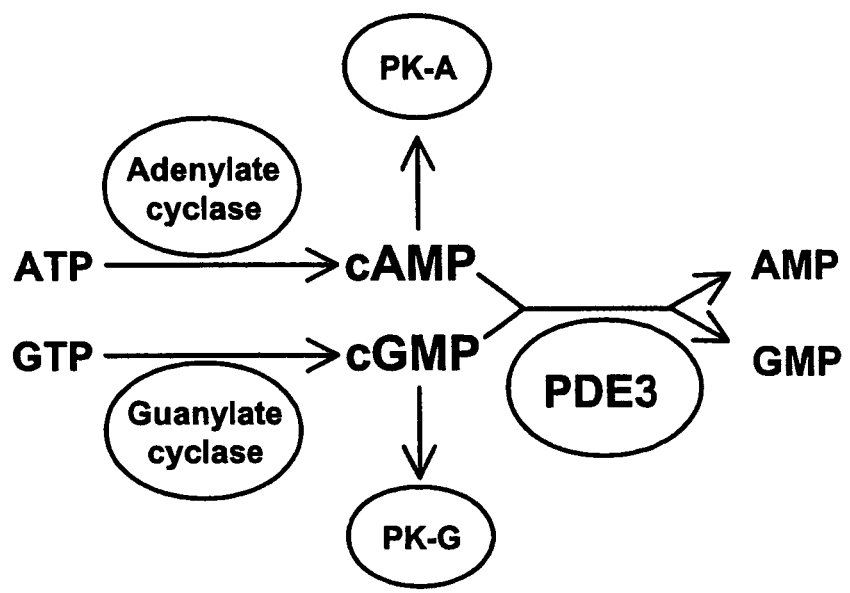
FIG. 1: Role of PDE3 in cAMP- and cGMP-mediated signal transduction. PK-A: cAMP-dependent protein kinase; PK-G: cGMP-dependent protein kinase.

The following abbreviations are used herein. Other abbreviations not listed below have their plain and ordinary meaning.

AKAP: PK-A ("A kinase") anchoring protein;
Akt: protein kinase B;
anti-CT: a polyclonal antibody raised against the C-terminus of PDE3A;
anti-MID: a polyclonal antibody raised against a mid-protein amino acid sequence in PDE3A;
anti-NT: a polyclonal antibody raised against the N-terminus of PDE3A;
CaM: calmodulin;
CCR: conserved catalytic region;
CK2: casein kinase 2;
CREB: cAMP response element-binding protein;
G: G protein (Gα, Gβ, Gγ);
Gly Syn: glycogen synthase;
IB: immunoblotting;
IP: immunoprecipitation;
IGF: insulin-like growth factor;
INS: 44-amino acid insert in CCR;
MAP kinase: mitogen-activated protein kinase;
MLP: muscle LIM protein;
NHR: N-terminal hydrophobic region;
p34$^{cdc2}$: cyclin-dependent protein kinase;
P1, P2, P3: phosphorylation sites in PDE3;
PDE: phosphodiesterase;
PDE3: type 3 phosphodiesterase;
PDE3-BP: PDE3-binding protein;
PGE1: prostaglandin E1;

Ph K: phosphorylase kinase;
PI3-K: phosphatidylinositol 3-kinase;
PK-A: cAMP-dependent protein kinase;
PK-B: protein kinase B, also known as Akt;
PK-C: protein kinase C;
PK-G: cGMP-dependent protein kinase;
PKI: a protein kinase inhibitor specific for PK-A;
PL: phospholamban;
RACK: receptor for activated PK-C;
rtX: recombinant form of protein "X";
Ry: ryanodine;
SERCA: Sarcoplasmic/endoplasmic reticulum calcium ATPase;
Tn: troponin;
TM: tropomyosin; and
V8: endopeptidase Glu-C.

As used herein, "a" or "an" may mean one or more than one of an item.

This application concerns, at least in part, isolated proteins and nucleic acids encoded by type 3 phosphodiesterase (PDE3, GenBank Accession No. NM000921), as well as methods of identification of isoform-selective inhibitors or activators and methods of therapeutic treatment of cardiomyopathy and/or pulmonary hypertension directed towards such proteins. In the present disclosure, reference to "PDE3" or "type 3 phosphodiesterase," without further qualification or limitation, means any or all of the isoforms of PDE3, either identified herein or as discovered or characterized by the methods disclosed herein. Where the sequences of the disclosed PDE3A isoforms proteins (SEQ ID NO:1, SEQ ID NO:2, SEQ ID NO:3) differ from the GenBank sequence, the sequences disclosed herein are believed to be more accurate and are preferred.

A "PDE3 isoform" is a variant of type 3 phosphodiesterase that differs in its primary structure (i.e., amino acid sequence) from other isoforms of PDE3. The term encompasses, but is not limited to, isoforms that are produced by truncation, amino acid substitution (mutation) or by alternative mRNA splicing, so long as some difference in amino acid sequence results. For the purposes of the present invention, other types of covalent modification would be considered to fall within the scope of a single isoform. For example, both phosphorylated and unphosphorylated forms of PDE3A-136 would be considered to represent the same isoform. The amino acid sequences of the three isoforms of PDE3A are as disclosed in SEQ ID NO:1, SEQ ID NO:2 and SEQ ID NO:3.

As used herein, an "inhibitor" of PDE3 means any compound or combination of compounds that acts to decrease the activity of PDE3, either directly or indirectly, with respect to catalyzing the breakdown of cAMP and/or cGMP. An inhibitor can be a molecule, an atom, or a combination of molecules or atoms without limitation. The term "antagonist" of PDE3 is generally synonymous with an "inhibitor" of PDE3. Inhibitors may act directly on PDE3 by, for example, binding to and blocking the catalytic site or some other functional domain of PDE3 that is required for activity. An inhibitor may also act indirectly, for example, by blocking the phosphorylation (or its effect on activity) or facilitating the dephosphorylation of PDE3 or by facilitating or interfering with the binding of PDE3 to another protein or peptide. The skilled artisan will realize that inhibitors and/or activators may affect PDE3 isoform protein activity and/or may affect the transcription, processing, post-transcriptional modification, stability and/or translation of one or more mRNA species encoding PDE3 isoform proteins (see, e.g., GenBank Accession No. NM000921, SEQ ID NO:14, SEQ ID NO:15, SEQ ID NO:18).

As used herein, an "activator" of PDE3 means any compound or combination of compounds that acts to increase the activity of PDE3, either directly or indirectly, with respect to catalyzing the breakdown of cAMP and/or cGMP. An activator can be a molecule, an atom, or a combination of molecules or atoms without limitation. The term "agonist" of PDE3 is generally synonymous with an "activator" of PDE3. Activators may act directly on PDE3 by, for example, binding some functional domain of PDE3 that is required for activity or by altering the secondary, tertiary or quaternary structure of PDE3 in a way that increases activity. An activator may also act indirectly, for example, by facilitating the phosphorylation or mimicking its effect, by blocking the dephosphorylation of PDE3 or by facilitating or interfering with the binding of PDE3 to another protein or peptide. As discussed above, activators may affect PDE3 isoforms at the level of mRNA and/or protein.

An "isoform-selective" inhibitor or activator of PDE3 is one that has a greater effect on one isoform of PDE3 than on any other isoform of PDE3. In preferred embodiments, an "isoform-selective" inhibitor or activator has at least a two-fold greater, more preferably three-fold greater, even more preferably four-fold greater, yet more preferably five-fold, and most preferably ten-fold or more greater effect on one isoform of PDE3 than on any other isoform of PDE3. For purposes of the present invention, the precise degree of selectivity of an inhibitor or activator for one isoform of PDE3 compared to other isoforms is not significant, so long as a desired therapeutic effect is achieved. For example, a desired therapeutic effect might be an improvement in cardiac output, with a decrease in long-term mortality, resulting from administration of an isoform-selective PDE3 inhibitor or activator compared with nonspecific PDE3 inhibitors. An "isoform-selective" inhibitor or activator of PDE3 encompasses, but is not limited to, an isoform-specific inhibitor or activator of PDE3. An isoform-specific inhibitor or activator of PDE3 is one that acts almost exclusively upon a single isoform of PDE3, so that the effect of the inhibitor or activator on one isoform of PDE3 compared to any other PDE3 isoform is at least an order of magnitude greater, more preferably two orders of magnitude greater, and most preferably three orders of magnitude or more greater.

Type 3 Phosphodiesterase

Cyclic nucleotide phosphodiesterases have a ubiquitous role in regulating cAMP- and cGMP-mediated intracellular signaling. Eleven families of these enzymes have been identified. Those in the PDE3 family are dual-specificity phosphodiesterases that bind both cAMP and cGMP with high affinity and hydrolyze them in a mutually competitive manner (FIG. 1). PDE3 inhibitors, which raise intracellular cAMP and cGMP content, have inotropic effects attributable to the activation of cAMP-dependent protein kinase (PK-A) in cardiac myocytes and vasodilatory effects attributable to the activation of cGMP-dependent protein kinase (PK-G) in vascular myocytes.

Figure 2:
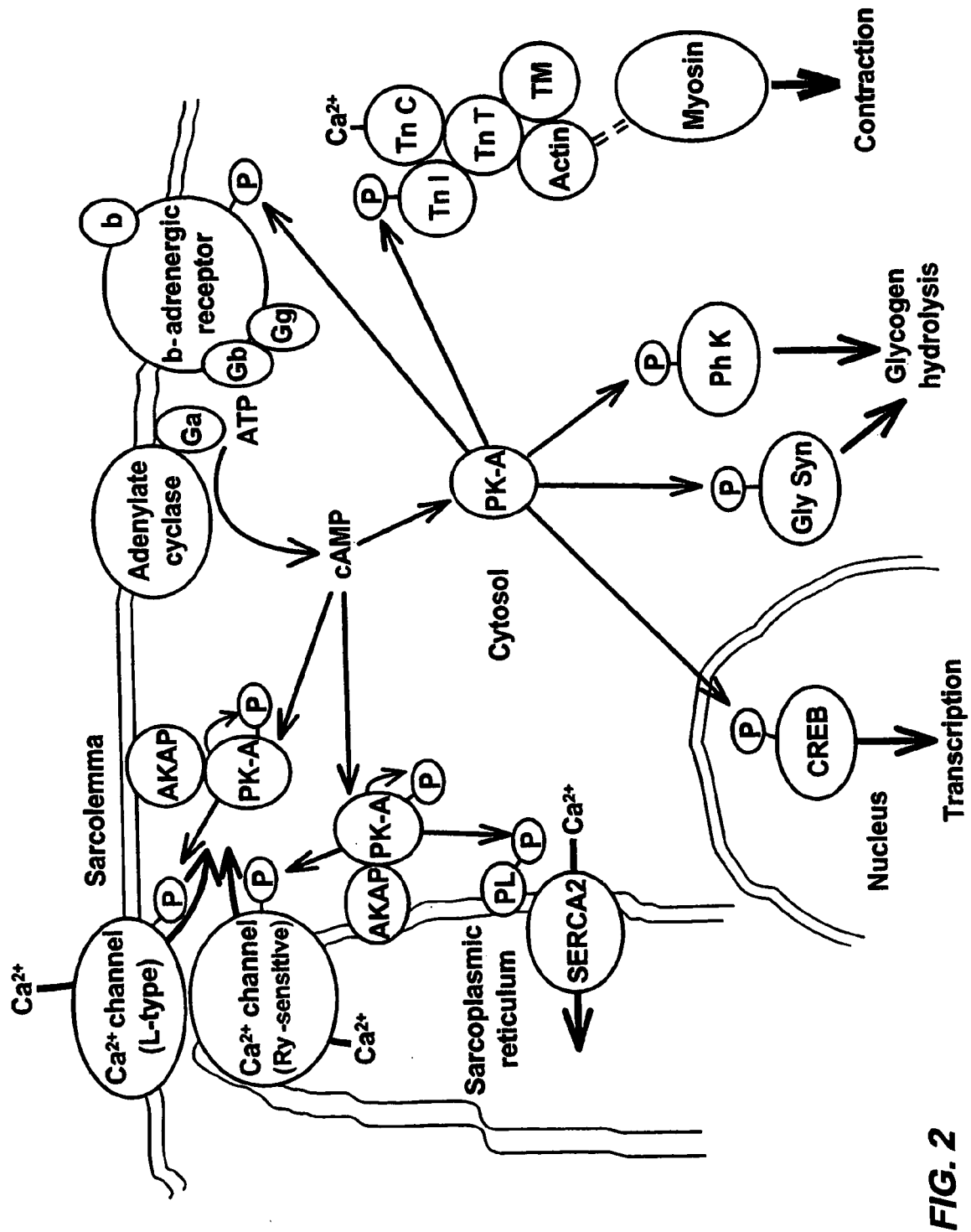
FIG. 2: PK-A substrates in cardiac myocytes. AKAP: PK-A ("A kinase") anchoring protein; CREB: cAMP response element-binding protein; Gly Syn: glycogen synthase; Ph K: phosphorylase kinase; PI3-K: phosphatidylinositol 3-kinase; PL: phospholamban; Ry: ryanodine; SERCA: Sarcoplasmic/endoplasmic reticulum calcium ATPase; Tn: troponin; TM: tropomyosin.

In addition to regulating contraction and relaxation in cardiac and vascular myocytes, PDE3 cyclic nucleotide phosphodiesterases are involved in platelet aggregation, anti-lipolytic responses to insulin in adipocytes, insulin secretion by pancreatic 13 cells and maturation of oocytes (Shakur et al., 2000a; Zhao et al., 1998; Andersen et al., 1998). FIG. 2 illustrates the numerous targets and the intracellular compartmentation of PK-A activity.

Figure 3:
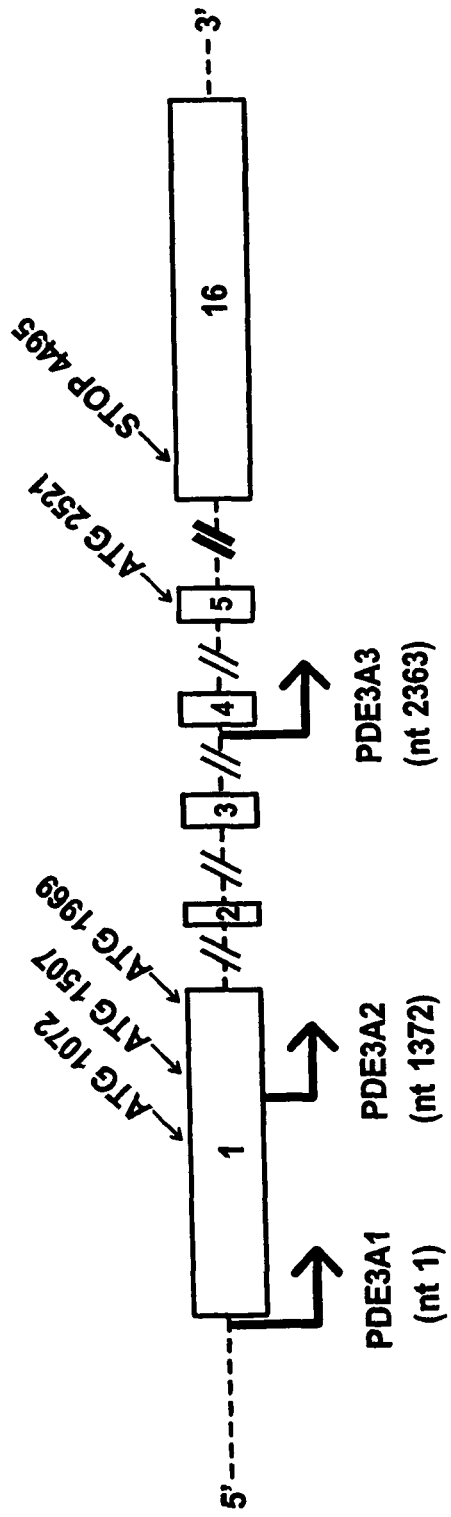
FIG. 3: Generation of PDE3A mRNAs by alternative transcription. Shaded boxes represent exons of PDE3A.

Two subfamilies of PDE3, products of genes designated PDE3A and PDE3B, have been identified. PDE3A is expressed primarily in cardiac and vascular myocytes and platelets, while PDE3B is expressed primarily in adipocytes, hepatocytes and pancreatic cells (but also in vascular myocytes) (Reinhardt et al., 1995). To date, one PDE3B (Taira et al., 1993) and three PDE3A cDNAs have been cloned. The latter are generated by transcription from alternative start sites in PDE3A. PDE3A1 (SEQ ID NO:14, SEQ ID NO:18), which was cloned from human myocardium, incorporates all sixteen exons of PDE3A (Meacci et al., 1992; Kasuya et al., 2000). PDE3A2 (SEQ ID NO:15), which was cloned from aortic myocytes, is transcribed from a start site in exon 1 (Choi et al., 2001). PDE3A3, cloned from placenta, is transcribed from a start site between exons 3 and 4 (Kasuya et al., 1995). The alternative start sites used for transcription of the three PDE3A mRNAs are illustrated in FIG. 3. The encoded amino acid sequences of the PDE3A isoforms are disclosed herein as SEQ ID NO:1 (PDE3A-136), SEQ ID NO:2 (PDE3A-118) and SEQ ID NO:3 (PDE3A-94). The skilled artisan will realize that the protein isoforms of PDE3 do not precisely correspond to the mRNA species transcribed from the PDE3A gene. For example, both PDE3A-118 and PDE3A-94 are translated from the PDE3A2 mRNA (SEQ ID NO:15).

Figure 4:
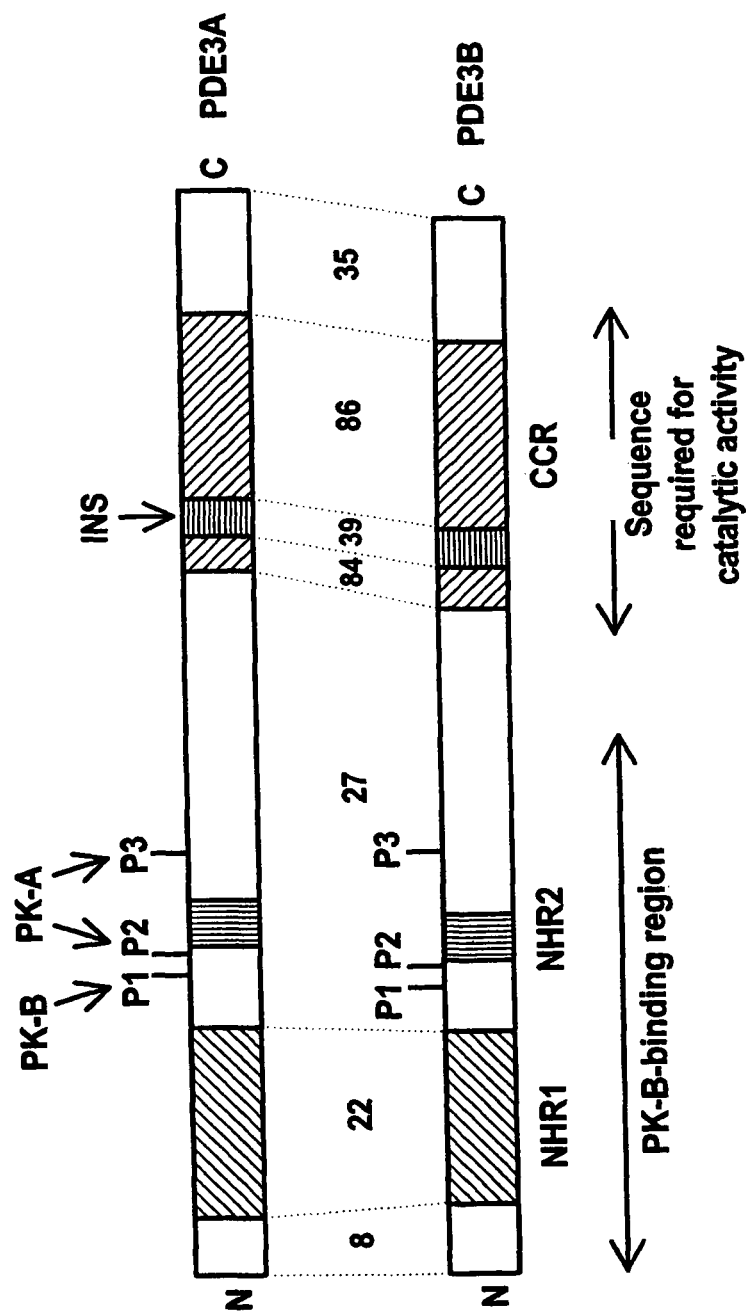
FIG. 4: Functional topography of PDE3A and PDE3B open reading frames showing NHR1 and 2, CCR with INS and PK-B and PK-A sites ("B," "$A_{up}$" and "$A_{down}$"). Numbers between dotted lines denote percent amino acid sequence identities of homologous regions.

The functional topographies of the proteins corresponding to the longest open reading frames (ORFS) of PDE3A and PDE3B are similar (FIG. 4). The C-terminus includes a sequence of about 280 amino acids, designated as "CCR" (FIG. 4), which is highly conserved among cyclic nucleotide phosphodiesterase families and in which catalytic activity resides. Within CCR lies a 44-amino acid insert, designated "INS," that is unique to the PDE3 family of cyclic nucleotide phosphodiesterases. The N-terminus contains two hydrophobic sequences, designated "NHR1" (about 200 amino acids) and "NHR2" (about 50 amino acids). NHR1 and NHR2 appear to be implicated in intracellular targeting. Between NHR1 and NHR2 are sites phosphorylated by PK-A and PK-B that, despite their distance from CCR, modulate catalytic activity. A second PK-A site whose function is unclear is located between NHR2 and CCR.

Despite the structural similarities, there are considerable differences between PDE3A and PDE3B with respect to their amino acid sequences. PDE3A and PDE3B are 84 to 86% identical within the CCR region, exclusive of INS. However, INS and the extreme C-terminus are only 35 to 39% identical, and the remaining upstream regions are less than 30% identical. Thus, while the catalytic sequences of the isoforms are similar, the regulatory portions of the isoforms appear to be very different and are likely to be differentially affected by the various inhibitors and activators of the present invention.

Structure/Function Relations

Catalytic activity. The catalytic activity of PDE3 enzymes requires almost the entire C-terminal sequence downstream of about amino acid 650, including the CCR domain that is largely conserved among all PDE families, as well as the INS and the CCR-flanking regions that are unique to the PDE3 family (FIG. 4). (Cheung et al., 1996; He et al., 1998.) The recent determination of the crystal structure of the related enzyme PDE4B2B has led to the identification of its catalytic site (Xu et al., 2000). The catalytic domain consists of three subdomains comprising 17 α-helices.

The active site, preserved in all PDE families, is at the junction of these three subdomains and is formed by the apposition of discontinuous amino acids. Differences in substrate affinity and selectivity among isoform families may be influenced in large part by differences in amino acid sequences that allosterically affect Glu1001 of PDE3A, which "reads" the 1- and 6-positions of the cyclic nucleotide purine ring and determines affinity (and, hence, selectivity) for cAMP and cGMP. Experiments involving PDE3/PDE4 chimeras indicate that the regions adjacent to this site contain the determinants of sensitivity to phosphodiesterase inhibitors (Atienza et al., 1999). This model, in which the active site is formed by discontinuous domains with allosteric determination of substrate affinity, may explain why so much sequence is required for catalytic activity. It may also explain why mutations of some amino acids preferentially affect binding of either cAMP or cGMP, while others affect the binding of both nucleotides (Zhang and Colman, 2000). While the N-terminus is not required for catalytic activity, N-terminal deletions increase the ratio of $V_{max}$ cGMP/$V_{max}$ cAMP, suggesting that the N-terminal region is involved in regulating catalytic activity (Tang et al., 1997).

The structural model described above has important implications regarding the feasibility of selective PDE3 inhibition or activation. The sequences of regions required for catalytic activity, INS and the regions flanking CCR, differ sufficiently between PDE3A and PDE3B to be reasonable targets for isoform-selective inhibitors or activators. As described in the Examples below, the development of anti-peptide antibodies selective for the C-terminus of either PDE3A or PDE3B is further evidence that selective inhibition or activation may occur. The existence of allosteric sites that differentially affect cAMP and cGMP hydrolysis allows for the identification of small molecules that selectively bind to these sites and affect either cAMP or cGMP hydrolysis.

Intracellular localization. Intracellular targeting of PDE3 appears to be determined principally by the N-terminal domains NHR1 and NHR2. NHR1 contains six transmembrane helices, the last two of which are sufficient to localize recombinant proteins containing these domains exclusively to intracellular membranes (Kenan et al., 2000; Shakur et al., 2000b). Such recombinants can be solubilized only by a combination of high salt and detergent, suggesting that they are intrinsic membrane proteins. Recombinants lacking NHR1 but retaining NHR2 are found in both microsomal and cytosolic fractions of transfected cells. High salt alone is sufficient to solubilize these proteins, suggesting that interactions with other proteins are involved in their intracellular localization. Recombinants lacking both NHR1 and NHR2 are predominantly cytosolic.

Regulation by protein phosphorylation. Phosphorylation of PDE3 plays a major role in the regulation of its function. In adipocytes, phosphorylation of PDE3 by PK-A and perhaps PI3-K are involved in the anti-lipolytic response to insulin (Smith et al., 1991). In oocytes, phosphorylation by PK-B results in the resumption of meiosis (Zhao et al., 1998). In promyeloid cells, phosphorylation by PK-B regulates cAMP pools that modulate DNA synthesis (Ahmad et al., 2000). In platelets, phosphorylation of PDE3A by PK-A and an insulin-activated protein kinase is associated with inhibition of aggregation (Grant et al., 1988; Lopez-Aparicio et al., 1993).

As described in more detail in the Examples below, three phosphorylation sites have been identified for the PDE3 isoforms (FIG. 4). PDE3B is phosphorylated in vivo by PK-A and possibly by PI3-K at Ser318 (site P2) (Rahn et al., 1996; Rondinone et al., 2000). The P2 site is dephosphorylated by a PP2A serine/threonine phosphatase (Resjö et al., 1999). PDE3B is also phosphorylated in vivo by PK-B at Ser296 (site P1) (Kitamura et al., 1999). Phosphorylation at either site increases catalytic activity. The fact that P1 and P2 lie between NHR1 and NHR2 raises the possibility that phosphorylation at these sites also affects intracellular targeting.

A third site, Ser421 in PDE3B (site P3), is phosphorylated by PK-A in vitro (Rascón et al., 1994). In adipocytes, it is unclear whether PDE3B is phosphorylated at P3 in response to isoproterenol or insulin in vivo. It is unknown whether this site is phosphorylated in PDE3B in other cell types and, if so, how phosphorylation at this site affects activity. It is also unknown whether phosphorylation at any of these sites affects inhibitor sensitivity, but a relevant paradigm is the reduction in the sensitivity of another phosphodiesterase, PDE4D3, to the inhibitor rolipram that results from phosphorylation of PDE4D3 by PK-A (Hoffmann et al., 1998). Prior to the present invention, the phosphorylation sites on the PDE3A isoforms were unknown. Numerous consensus phosphorylation sites are present in the PDE3A amino acid sequence and it was unknown which of these sites was phosphorylated in vivo.

The identification of protein kinases that phosphorylate PDE3 isoforms and alter their function may elucidate their role in dilated cardiomyopathy. Phosphorylation and activation of PDE3 by PK-B, for example, may be an anti-apoptotic mechanism related to the deleterious long-term effects of PDE3 inhibition in dilated cardiomyopathy. The sequences of PDE3A and PDE3B contain multiple consensus sites for CK2, PK-C and other protein kinases. It may be especially important to consider cross-regulation by these kinases in the pathophysiology of cardiomyopathy and/or pulmonary hypertension. By analogy, PDE4D3 phosphorylation by ERK2 profoundly reduces its activity, and this reduction is reversed by phosphorylation by PK-A (Hoffmann et al. 1999).

Protein-Protein Interactions

Interactions with other proteins are involved in the regulation of activity and intracellular localization of other families of PDE. Binding of $Ca^{2+}$/CaM stimulates catalytic activity of PDE1 via multiple CaM-binding domains (Sonnenburg et al., 1995). The activities of PDE6 $\alpha\beta$ and $\alpha'\alpha'$ dimers are inhibited by their interaction with PDEγ. Phototransduction occurs when this inhibition is relieved by interaction with the rhodopsin-coupled G protein transducin (Granovsky et al., 2000). PDE6 dissociates from intracellular membranes upon binding to PDEδ (Florio et al., 1996). Interactions with RACK1 and AKAPs are involved in the subcellular targeting of PDE4 isoforms to multi-enzyme complexes (Yarwood et al., 1999; Dodge et al., 2001). The interactions of PDE4 with SH3 domains of SRC family tyrosine kinases affect intracellular localization and inhibitor sensitivity (McPhee et al., 1999).

Prior to the present invention, it was unknown whether PDE3 is catalytically regulated or intracellularly targeted via interactions with other proteins. PDE3B, insulin receptor, the p85 and p110 subunits of PI3-K and an unidentified 97-kDa protein are co-immunoprecipitated from human adipocytes with anti-insulin receptor antibodies (Rondinone et al., 2000). Preliminary data on the interaction of PDE3B with 14-3-3 proteins has been reported (Palmer et al., 2000). 14-3-3 proteins bind to phosphorylated serine residues in consensus motifs and affect intracellular localization of proteins in diverse ways (Fu et al., 2000). As discussed in the Examples below, site P1 in PDE3A and PDE3B approximates this consensus motif, raising the possibility that phosphorylation affects intracellular localization through interaction with 14-3-3 proteins. The Examples further show the existence of stable complexes of PDE3B with PK-B and AKAP220. Taken together, these observations indicate that interactions of other proteins with the N-terminus are involved in PDE3 function, and that phosphorylation of PDE3 may affect these interactions.

Proteins

In referring to the function of PDE3 or "wild-type" activity, it is meant that the molecule in question has the ability to catalyze the breakdown of cAMP and cGMP. Molecules possessing this activity may be identified using assays familiar to those of skill in the art. For example, in vitro assay of homogenates containing PDE3 activity, or variants thereof, will identify those molecules having PDE3 activity by virtue of their ability to degrade cAMP or cGMP. The skilled artisan will realize that a variety of phosphodiesterases are endemic to various cell lines and tissues and will select an appropriate system lacking endogenous phosphodiesterase to perform such assays.

The term "PDE3 gene" refers to any DNA sequence that is substantially identical to a DNA sequence encoding a PDE3 protein as defined above. Allowing for the degeneracy of the genetic code, sequences that have at least about 50%, usually at least about 60%, more usually about 70%, most usually about 80%, preferably at least about 90%, more preferably at least about 95%, most preferably 98% or more of nucleotides that are identical to the cDNA sequences of PDE3 are "as set forth in" those sequences. Sequences that are substantially identical or "essentially the same" as the cDNA sequences of PDE3 also may be functionally defined as sequences that are capable of hybridizing to a nucleic acid segment containing the complement of the cDNA sequences of PDE3 under conditions of relatively high stringency. Such conditions are typically relatively low salt and/or high temperature conditions, such as provided by about 0.02 M to about 0.15 M NaCl at temperatures of about 50° C. to about 70° C. Such selective conditions tolerate little, if any, mismatch between the complementary strands and the template or target strand. Any such gene sequences may also comprise associated control sequences.

In certain embodiments, the present invention relates to fragments of PDE3 polypeptides that may or may not retain the phosphodiesterase activity of PDE3, although in preferred embodiments, the fragments exhibit phosphodiesterase activity. Fragments including the N-terminus of the molecule may be generated by genetic engineering of translation stop sites within the coding region (discussed below). Alternatively, treatment of the protein molecule with proteolytic enzymes can produce a variety of N-terminal, C-terminal and internal fragments. Examples of fragments may include contiguous residues of the PDE3 amino acid sequences of 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500 or more amino acids in length. These fragments may be purified according to known methods, such as precipitation (e.g., ammonium sulfate), HPLC, ion exchange chromatography, affinity chromatography (including immunoaffinity chromatography), or various size separations (e.g., sedimentation, gel electrophoresis, gel filtration).

Substantially identical analog proteins will be greater than about 80% identical, more preferably 90% identical, even more preferably 95% identical, yet more preferably 98% identical, even more preferably 99% identical, yet even more preferably 99.5% identical, and most preferably 99.9% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Protein Purification

Certain embodiments may involve purification of one or more individual PDE3 isoforms or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast protein liquid chromatography (FPLC) or even HPLC.

Certain aspects of the present invention concern the purification, and in particular embodiments, the substantial purification, of an encoded protein or peptide. The terms "isolated" or "purified" as applied to a protein or peptide, are intended to refer to a composition, isolatable from other components, wherein the protein or peptide is purified to any degree relative to its naturally obtainable state. A purified protein or peptide, therefore, also refers to a protein or peptide free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, about 98%, about 99% or more of the proteins in the composition.

Various methods for quantifying the degree of purification of a protein or peptide will be known to those of skill in the art. These include, for example, determining the specific activity of an active fraction or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the protein or peptide exhibits a detectable activity.

Various techniques suitable for use in protein purification will be well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the proteins or peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of protein product or in maintaining the activity of an expressed protein.

It is known that the migration of a polypeptide can vary, sometimes significantly, with different conditions of SDS/PAGE (Capaldi et al., 1977). It will, therefore, be appreciated that under differing electrophoresis conditions, the apparent molecular weights of purified or partially purified expression products may vary.

High Performance Liquid Chromatography (HPLC) is characterized by a very rapid separation with high resolution of peaks. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a type of partition chromatography that is based on molecular size. As long as the material of which the particles are made does not adsorb the molecules, the sole factor determining rate of flow is the size of the pores. Hence, molecules are eluted from the column in decreasing size, so long as the shape is relatively constant. In gel chromatography, separation is independent of all other factors such as pH, ionic strength, temperature, etc.

Affinity chromatography relies on the specific affinity between a substance to be isolated and a molecule to which it can specifically bind. The column material is synthesized by covalently coupling one of the binding partners, such as an antibody or an antibody-binding protein to an insoluble matrix. The column material is then able to specifically adsorb the target substance from the solution. Elution occurs by changing the conditions to those in which binding will not occur (e.g., altered pH, ionic strength, temperature, etc.). One of the most common forms of affinity chromatography is immunoaffinity chromatography. The generation of antibodies that would be suitable for use in accord with the present invention is discussed below.

Synthetic Peptides

In some embodiments, the present invention concerns smaller peptides for various uses, such as antibody generation or screening for potential inhibitors or activators that can bind to various epitopes of PDE3. Smaller peptides of about 100 amino acids or less can be synthesized in solution or on a solid support in accordance with conventional techniques. Various automated peptide synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to selected regions of the PDE3 protein, can be readily synthesized and then screened in screening assays designed to identify reactive peptides or other small molecules. Alternatively, recombinant DNA technology may be employed wherein a nucleotide sequence which encodes a peptide of the invention is inserted into an expression vector, transformed or transfected into an appropriate host cell, and cultivated under conditions suitable for expression. Expression of cloned PDE3 sequences is preferred in embodiments where PDE3 peptides of greater than about 50 amino acids in length are desired. The skilled artisan will realize that it is also possible to synthesize short peptide fragments and covalently link them together, for example, using carbodiimides as cross-linking groups. In this manner, a peptide of any desired length can be produced by synthesizing shorter fragments and joining them in the appropriate order.

Two-Dimensional Mapping

Two-dimensional mapping, also known as proteome analysis, is a useful tool for characterization of cellular protein expression. Specifically contemplated are the methods described in Gibson (1974); Beemon and Hunter (1978); and Luo, et al. (1990), each of which is incorporated herein by reference in their entirety. Two-dimensional mapping is based on two-dimensional electrophoretic separation of proteins in a cellular lysate or homogenate so that each protein can be identified using specific coordinates in a two-dimensional protein map from which it can be extracted and further identified (by, e.g., micro sequencing or mass spectrometry).

For mapping, the proteins in a cellular homogenate or lysate are immunoprecipitated, using an antibody or series of antibodies specific for the proteins of interest, and run on a preparative electrophoretic protein gel. The proteins from this gel are then transferred to an immobilizing matrix. Various immobilizing matrices are available and may be used. Preferred matrices for purposes of the present invention are nitrocellulose or a nylon matrix such as Immobilon (Millipore, Bedford, Mass.). The resulting protein-matrix hybrid, called a blot, is then washed with water in order to remove any non-bound cellular debris from the initial homogenate or lysate, which may cause interference in subsequent steps. The blot is then contacted with an antibody, or series of antibodies, specific to the protein or proteins of interest in the cellular homogenate or lysate. The skilled artisan will realize that these antibodies may be monoclonal, polyclonal, or both and use of any will not substantially change the outcome of this procedure. Once the protein or proteins of interest from the cellular homogenate or lysate are identified by the antibodies binding to the proteins and forming an antibody-protein complex, they are physically excised from the rest of the blot matrix. One of reasonable skill in the art will recognize that any common method of antibody detection may be used to identify the aforementioned antibody-protein complex. These may include, but are not limited to, ELISA, alkaline-phosphatase-conjugated secondary antibody, enzyme-conjugated antibodies, radiolabeled antibodies, or any other common method of detection. For purposes of the present invention, radiolabeled antibodies are the preferred method of detection.

The protein or proteins, still in the form of bands from the immobilizing matrix, are digested by one of several common peptidase enzymes. These are enzymes that cleave proteins at specific locations only and include, but are not limited to, trypsin, chymotrypsin, CNBr and V8. Digestion may be allowed to run to completion, i.e., where every possible site that the chosen peptidase could recognize in the sample is cleaved, or it may be a partial digestion, merely run for a shorter period of time and not to completion. Once the desired level of digestion is completed, the peptidase chosen is removed from the sample, typically by centrifugation and transfer of the supernatant to a new container or vessel.

These digested samples are then loaded onto a cellulose thin layer plate for pH-driven electrophoresis, the first "dimension" in the mapping process. The digested proteins will behave on this thin layer plate much as they would when subjected to standard SDS-PAGE, except that the digested protein fragments will separate by charge according to the pH of the electrophoresis buffer. By way of example only, if the electrophoresis buffer chosen has a pH ranging from 1.9 to 4.72, then the majority of the digested peptide fragments in the sample will be positively charged. The thin layer plate should thus be loaded appropriately for optimal separation of the digested peptide fragments. In this example, the plate should be loaded at a distance closer to the positive electrode and farther from the negative electrode. The skilled artisan will recognize that the pH used in any individual electrophoresis should be that which will give an optimal distribution of the peptides. Preferred pH values include 8.9, more preferably 4.72, even more preferably 1.9. After electrophoresis is complete, the thin layer plate is typically dried in an oven. It is thought that this step irreversibly binds the digested peptide fragments to the cellulose on the thin layer plate.

Chromatography, the second "dimension" in the mapping, is next performed. The thin layer plate is placed in a chamber with a chromatography liquid, but only one side of the thin layer plate is immersed in this liquid. The thin layer plate should be placed in the liquid in such a manner that the liquid used, as it travels up through the thin layer plate via capillarity, does so at a ninety (90) degree angle from the direction electrophoresis was performed on the plate. When chromatography is performed in this way, it will separate the digested peptide fragments in some manner apart from overall charge. Thus, when chromatography has completed, the digested peptides will have been separated first by overall charge, then by a property driven by the chromatography liquid, hence the "two-dimensional" separation.

The skilled artisan will recognize that the chromatography buffer will differ based upon the desired property for separation and will use that buffer that will give optimal separation of the peptides in question. By way of example only, chromatography buffers may be selected that separate according to hydrophobicity, alkalinity, water solubility, or any other common means of separation apart from overall charge.

Once chromatography is complete, the thin layer plate is dried and the digested peptide fragments thus separated are detected using common means (such as detection of a radioactively labeled antibody).

Protein Chips

Protein chip technology provides a means of rapidly screening sample compounds for their ability to hybridize to PDE3 isoform proteins, peptides or subunits immobilized on a solid substrate. Specifically contemplated are protein array-based technologies such as those disclosed by Cheng et al. (U.S. Pat. No. 6,071,394), Zanzucchi et al. (U.S. Pat. No. 5,858,804) and Lee et al. (U.S. Pat. No. 5,948,627), each of which is incorporated herein by reference in their entirety. These techniques involve methods for analyzing large numbers of samples rapidly and accurately. The technology capitalizes on the binding properties of proteins or peptides to screen samples.

A protein chip or array consists of a solid substrate upon which an array of proteins or peptides have been attached. For screening, the chip or array is contacted with a sample containing one or more test compounds that may function as PDE3 inhibitors or activators. The degree of stringency of binding of test compound to peptides may be manipulated as desired by varying, for example, salt concentration, temperature, pH and detergent content of the medium. The chip or array is then scanned to determine which proteins or peptides have bound to a test compound.

The structure of a protein chip or array comprises: (1) an excitation source; (2) an array of probes; (3) a sampling element; (4) a detector; and (5) a signal amplification/treatment system. A chip may also include a support for immobilizing the probe.

In particular embodiments, a protein or peptide may be tagged or labeled with a substance that emits a detectable signal. The tagged or labeled species may be fluorescent, phosphorescent, or luminescent, or it may emit Raman energy or it may absorb energy. When the protein or peptide binds to a test compound, a signal is generated that is detected by the chip. The signal may then be processed in several ways, depending on the nature of the signal. In alternative embodiments, the test compounds may be labeled.

The proteins or peptides may be immobilized onto an integrated microchip that also supports a phototransducer and related detection circuitry. Alternatively, PDE3 proteins or peptides may be immobilized onto a membrane or filter that is then attached to the microchip or to the detector surface itself. The proteins or peptides may be directly or indirectly immobilized onto a transducer detection surface to ensure optimal contact and maximum detection. A variety of methods have been utilized to either permanently or removably attach proteins to a substrate. When immobilized onto a substrate, the proteins are stabilized and may be used repeatedly.

Exemplary substrates include nitrocellulose, nylon membrane or glass. Numerous other matrix materials may be used, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly (methyl methacrylate), poly(dimethyl siloxane) and photopolymers that contain photoreactive species such as nitrenes, carbenes and ketyl radicals capable of forming covalent links with target molecules (U.S. Pat. Nos. 5,405,766 and 5,986,076, each incorporated herein by reference).

Binding of proteins or peptides to a selected support may be accomplished by any of several means. For example, proteins may be bound to glass by first silanizing the glass surface, then activating with carbodiimide or glutaraldehyde. Alternative procedures may use reagents such as 3-glycidoxypropyltrimethoxysilane (GOP) or aminopropyltrimethoxysilane (APTS) linked via amino groups. With nitrocellulose membranes, the protein probes may be spotted onto the membranes.

Specific proteins or peptides may first be immobilized onto a membrane and then attached to a membrane in contact with a transducer detection surface. This method avoids binding the protein onto the transducer and may be desirable for large-scale production. Membranes particularly suitable for this application include nitrocellulose membrane (e.g., from BioRad, Hercules, Calif.) or polyvinylidene difluoride (PVDF) (BioRad, Hercules, Calif.) or nylon membrane (Zeta-Probe, BioRad) or polystyrene base substrates (DNA.BIND™ Costar, Cambridge, Mass.).

Antibodies

Antibody Production

Certain embodiments of the present invention involve antibody production against one or more PDE3 isoforms. Means for preparing and characterizing antibodies are well known in the art (see, e.g, Harlow and Lane, *Antibodies: A Laboratory Manual*, Cold Spring Harbor Laboratory, 1988, incorporated herein by reference).

Methods for generating polyclonal antibodies are well known in the art. Briefly, a polyclonal antibody is prepared by immunizing an animal with an immunogenic composition and collecting antisera from that immunized animal. A wide range of animal species may be used for the production of antisera. Typically, the animal used for production of antiantisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary, therefore, to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes may be used to administer the immunogen (subcutaneous, intramuscular, intradermal, intravenous and intraperitoneal). The production of polyclonal antibodies may be monitored by sampling blood of the immunized animal at various points following immunization. Later, booster injections may also be given. The process of boosting and titering is repeated until a suitable titer is achieved. When a desired level of immunogenicity is obtained, the immunized animal may be bled and the serum isolated and stored, and/or the animal may be used to generate MAbs. For production of rabbit polyclonal antibodies, the animal may be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. Following immunization, somatic cells with the potential for producing antibodies, specifically B lymphocytes (B cells), are selected for use in the MAb-generating protocol. These cells may be obtained from biopsied spleens, tonsils or lymph nodes, or from a peripheral blood sample. Often, a panel of animals will have been immunized and the spleen of the animal with the highest antibody titer will be removed and the spleen lymphocytes obtained by homogenizing the spleen with a syringe.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are nonantibody-producing, have high fusion efficiency, and enzyme deficiencies that render them incapable of growing in certain selective media that support the growth of only the desired fused cells (hybridomas). Any one of a number of myeloma cells may be used, as are known to those of skill in the art (e.g., Goding, pp. 65-66, 1986). For example, where the immunized animal is a mouse, one may use P3-NS-1-Ag4-1, Sp2/0, P3-X63/Ag8, X63-Ag8.653, NS1/1.Ag41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71-74, 1986).

Viable, fused hybrids are differentiated from the parental, unfused cells by culturing in a selective medium. The selective medium generally contains an agent that blocks the de novo synthesis of nucleotides in the tissue culture media. Exemplary and preferred agents are aminopterin, methotrexate, and azaserine. Where aminopterin or methotrexate is used, the media is supplemented with hypoxanthine and thymidine as a source of nucleotides (HAT medium). Where azaserine is used, the media is supplemented with hypoxanthine. A preferred selection medium is HAT. The only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones may then be propagated indefinitely to provide MAbs.

In accordance with the present invention, fragments of the monoclonal antibody of the invention may be obtained from the monoclonal antibody produced as described above, by methods that include digestion with enzymes such as pepsin or papain and/or cleavage of disulfide bonds by chemical reduction. Alternatively, monoclonal antibody fragments encompassed by the present invention may be synthesized using an automated peptide synthesizer.

Immunoassay Methods

Immunocomplex formation. In still further embodiments, the present invention concerns immunodetection methods for binding, purifying, removing, quantifying or otherwise generally detecting peptides of interest. The PDE3 proteins or peptides of the present invention may be employed to detect antibodies having reactivity therewith or, alternatively, antibodies prepared in accordance with the present invention may be employed to detect or purify the PDE3 proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. One may find additional advantages through the use of a secondary binding ligand such as a second antibody or a biotin/avidin ligand binding arrangement, as is known in the art.

Further methods include the detection of primary immune complexes by a two-step approach. A second binding ligand, such as an antibody, that has binding affinity for the target protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention may be of utility in the diagnosis of various disease states. A biological or clinical sample suspected of containing either the target protein or peptide or corresponding antibody is used. In certain embodiments, samples from patients with cardiomyopathy and/or pulmonary hypertension may be immunoassayed to determine the type and abundance of different PDE3 isoforms present in one or more tissues. Targeted therapy directed towards PDE3 may utilize inhibitors and/or activators known to be selective or specific for one or more PDE3 isoforms that are detected in the patient's affected tissues.

Immunohistochemistry. The antibodies of the present invention may be used in conjunction with fresh-frozen or formalin-fixed, paraffin-embedded tissue blocks prepared by immunohistochemistry (IHC). Any IHC method well known in the art may be used, such as those described in *Diagnostic Immunopathology*, 2nd edition, edited by Robert B. Colvin, Atul K. Bhan and Robert T. McCluskey. Raven Press, New York, 1995 (incorporated herein by reference).

ELISA. Certain immunoassays are the various types of enzyme-linked immunosorbent assays (ELISAs) and radio-immunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, antibodies binding to the PDE3 proteins of the invention are immobilized onto a selected surface exhibiting protein affinity, such as a well in a polystyrene microtiter plate. Then, a test composition suspected of containing the PDE3 isoforms, such as a clinical sample, is added to the wells. After binding and washing to remove non-specifically bound immunocomplexes, the bound antigen may be detected. Detection is generally achieved by the addition of a second antibody specific for the target protein, linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label. The skilled artisan will realize that a variety of ELISA and other immunoassay techniques are known in the art, any of which may be performed within the scope of the present invention.

Methods of Immobilization

In various embodiments, the PDE3 proteins or peptides or anti-PDE3 antibodies of the present invention may be attached to a solid surface ("immobilized"). In a preferred embodiment, immobilization may occur by attachment to a solid surface, such as a magnetic, glass or plastic bead, a plastic microtiter plate or a glass slide.

Immobilization of proteins or peptides may be achieved by a variety of methods involving either non-covalent or covalent interactions between the immobilized protein or peptide and an anchor. In an exemplary embodiment, immobilization may be achieved by coating a solid surface with a cross-linkable group, such as an amino, carboxyl, sulfhydryl, alcohol or other group and attaching a protein or peptide using a cross-linking reagent.

Homobifunctional reagents that carry two identical functional groups are highly efficient in inducing cross-linking. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino or carboxyl-specific groups. Of these, reagents directed to free amino groups have become especially popular because of their commercial availability, ease of synthesis and the mild reaction conditions under which they can be applied.

Exemplary methods for cross-linking molecules are disclosed in U.S. Pat. Nos. 5,603,872 and 5,401,511. Amine residues may be introduced onto a surface through the use of aminosilane. Cross-linking reagents include bisimidates, dinitrobenzene, N-hydroxysuccinimide ester of suberic acid, disuccinimidyl tartarate, dimethyl-3,3'-dithiobispropionimidate, N-succinimidyl-3-(2-pyridyldithio)-propionate, 4-(bromoaminoethyl)-2-nitrophenylazide, 4-azidogyloxal and a water-soluble carbodiimide, preferably 1-ethyl-3-(3-dimethylaminopropyl)carbodiimide (EDC). The present invention is not limiting as to the cross-linking agents that may be used.

Nucleic Acids

The present invention also provides in another embodiment, genes encoding PDE3. As discussed below, a "PDE3 gene" may contain a variety of different bases and yet still produce a corresponding polypeptide that is indistinguishable functionally, and in some cases structurally, from the genes disclosed herein. Other embodiments of the invention may concern nucleic acids (antisense RNAs, ribozymes) that can bind to and inhibit transcription and/or translation of one or more RNA species encoding a PDE3A isoform protein. The design and production of antisense RNAs, or cDNAs encoding antisense RNAs, are well known in the art and any such known method may be used in the practice of the present invention (e.g., U.S. Pat. Nos. 6,210,892; 6,248,724; 6,277,981; 6,300,492; 6,303,374; 6,310,047; 6,365,345). In certain embodiments, an antisense RNA may be targeted against a particular PDE3A isoform, for example, by selecting a target sequence that is present in one PDE3A isoform mRNA but not in another. The term "nucleic acid" encompasses single-stranded, double-stranded, triple-stranded DNA and/or RNA of any type, as well as analogs of and chemically modified forms of DNA and/or RNA.

Any reference to a nucleic acid should be read as encompassing a host cell containing that nucleic acid and, in some cases, capable of expressing the product of that nucleic acid. Cells expressing nucleic acids of the present invention may prove useful in the context of screening for agents that induce, repress, inhibit, augment, interfere with, block, abrogate, stimulate, or enhance the catalytic activity, regulatory properties or subcellular localization of PDE3 isoforms.

Nucleic Acids Encoding PDE3

Nucleic acids may contain an entire gene, a cDNA, or a domain of a PDE3 isoform that expresses catalytic activity, or any other fragment of the sequences set forth herein. The nucleic acid may be derived from genomic DNA, i.e., cloned directly from the genome of a particular organism. In preferred embodiments, however, the nucleic acid would comprise complementary DNA (cDNA).

The DNA segments of the present invention include those encoding biologically functional equivalent PDE3 proteins and peptides. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

Assay of PDE3A Isoform mRNA Levels

Some embodiments of the invention concern methods for determining the levels of mRNA species encoding the three PDE3A isoforms in various cells, tissues, organs or other samples. A variety of assays for mRNA levels are known in the art and any such known assay may be used. The three PDE3A isoform mRNAs differ in length, not in sequence. Therefore, any assay for mRNA levels must either separate the mRNAs by size or must be performed by a subtraction process. The skilled artisan is aware that RNA species are particularly sensitive to endogenous and/or exogenous RNAse degradation and that great care must be taken to inhibit or inactivate RNAse before RNA levels can be determined. Typical procedures involve treatment of solutions with diethylpyrocarbonate (DEPC) and autoclaving, as well as addition of commercial RNAse inhibitors.

Northern blotting is a well-known method for assaying mRNA species that differ by size. Either total cell RNA or polyadenylated mRNA may be purified from a sample by known techniques (e.g., Sambrook et al., 1989). The purified RNA is separated by size using gel electrophoresis. After transfer to a nylon, nitrocellulose or other membrane, the size-separated RNAs are probed with a labeled oligonucleotide that hybridizes specifically with one or more target RNAs. The presence of an RNA species that hybridizes with the oligonucleotide probe is detected by autoradiography, fluorography or other known techniques. Further examples of the use of Northern blotting to detect PDE3A mRNAs are disclosed below in the Examples section. It appears that in most cell types, a given PDE3A isoform mRNA will either be present or absent. Thus, generally it will be sufficient to detect the presence or absence of a PDE3A isoform mRNA. However, the amounts of each isoform mRNA present in a sample may also be determined by standard techniques, such as using autoradiography or fluorography to expose a film (e.g., Kodak X-Omat, Eastman Kodak, Rochester, N.Y.), and scanning the band intensity on the developed film.

Other well known methods for detecting and/or quantifying mRNA species may be used. For example, the target nucleic acids of interest may be amplified as disclosed below. Amplification products may be attached to a membrane, 96-well plate, nucleic acid chip or other substrate and detected. Because the PDE3A isoforms do not differ in sequence, determination of the amounts of each mRNA species would require three separate probes. One probe would be designed to be complementary to the PDE3A3 mRNA sequence and would detect PDE3A1, PDE3A2 and PDE3A3. A second probe would be designed to be complementary to the 5' portion of the PDE3A2 mRNA sequence (see SEQ ID NO:15), for example, to the 3' end of exon 1 or to exons 2 or 3. That probe would hybridize with mRNAs for PDE3A1 and PDE3A2. A third probe would be designed to be complementary with the 5' end of exon 1. That probe would only hybridize with the mRNA encoding PDE3A1 (SEQ ID NO:14, SEQ ID NO:18). By assaying the levels of PDE3A mRNAs using the three different probes, it would be possible to determine the amount of each isoform mRNA species by subtraction.

As discussed in further detail in the Examples section, the PDE3A isoforms are encoded by at least two, and possibly by three different mRNAs. PDE3A1 mRNA is translated to a 136 kDa protein isoform, while a PDE3A2 mRNA may be translated to give both 94 kDA and 118 kDA protein isoforms. Alternatively, each of the different sized protein isoforms may be encoded by a separate mRNA species.

Apparatus and kits for assay of mRNA expression levels are commercially available, such as the Nanochip™ Workstation (Nanogen, Inc., San Diego, Calif.), Affymetrix Genechip® (Affymetrix, Inc., Santa Clara, Calif.), etc.

High Through-Put Screening

In certain embodiments of the invention, high throughput screening (HTS) methods directed towards mRNA may be used to assay for inhibitors and/or activators that affect expression of specific PDE3 isoforms. Such methods are known in the art and, in some embodiments, may be performed using kits and/or apparatus obtained from commercial vendors (e.g., Xpress-Screen mRNA Detection Assay Service, Applied Biosystems, Foster City, Calif.). The object of high throughput screening is to survey thousands of compounds, for example, in the form of small molecule libraries, phage display libraries, native plant or animal extracts, combinatorial chemistry libraries, etc., for a pharmaceutically significant effect on a target protein, cell, tissue, organ or organism. Effective compounds may be further modified by chemical substitution and/or modification to provide increased efficacy, safety, duration of effect, etc.

HTS assays may be directed against one or more proteins or peptides of interest, such as PDE3A-136, PDE3A-118, PDE3A-94 or PDE3B-137 using known techniques. Preferably, libraries of potential inhibitors and/or activators are exposed to PDE3 proteins and/or peptides and enzyme catalytic activity and/or regulatory properties are assayed. Such assays may be performed, for example, in 96-well microtiter plates using known colorimetric, luminescent and/or radioactive assays for enzyme activity. In other alternative embodiments, the test peptides and/or proteins may be attached to a surface, such as a protein chip, microtiter wells, membrane or other surface known in the art and libraries of compounds may be screened for their ability to bind to the various PDE3 isoforms.

Protein-based HTS assays can be laborious and time-consuming. An alternative method for performing HTS analysis is to screen targets, such as cells, tissues, organs or organisms, for an effect of a test compound on mRNA levels. With respect to PDE3 isoforms, such assays may potentially be directed towards identifying compounds that directly or indirectly affect PDE3A1 or PDE3A2 mRNA levels. The cell or tissue of interest, for example, a tissue sample from an individual with dilated cardiomyopathy or an Sfo cell transfected with a PDE3A-encoding gene, may be exposed to a series of test compounds in 96- or 384-well microplates. After incubation and cell lysis, a biotinylated probe specific for the mRNA of interest is used to hybridize to total cell RNA or to purified polyadenylated mRNA. The DNA-RNA hybrid may be transferred to a streptavidin-coated plate, which binds to the biotinylated probe. A labeled antibody, such as an alkaline phosphatase-conjugated antibody that binds specifically to RNA-DNA hybrids, is incubated with the plate. Unbound antibody is removed by washing and the presence of RNA-DNA hybrids is detected by developing the labeled antibody, for example, using a chemiluminescent substrate (Xpress-Screen, Applied Biosystems). In this way, hundreds of test compounds may be screened simultaneously for an effect on PDE3 isoform expression.

In alternative embodiments, test compounds may be screened by looking for secondary effects of PDE3A isoform proteins. Inhibition or activation of PDE3 activity and/or expression may be determined indirectly. By affecting the cellular levels of cAMP and/or cGMP, PDE3 isoforms may affect the expression of known cyclic nucleotide-regulated genes. Cells or tissues that have been exposed to test compounds may be screened, as described above, for mRNAs encoded by genes that are known to be dependent on cyclic nucleotide levels. Effects of inhibitors and/or activators of PDE3 isoforms may be monitored by screening normal, diseased and/or transformed cells for changes in expression levels of cAMP- or cGMP-regulated genes.

Nucleic Acid Amplification

Nucleic acids of use as a template for amplification may be isolated from cells contained in a biological sample according to standard methodologies (Sambrook et al., 1989). The nucleic acid may be genomic DNA or fractionated or whole cell RNA. Where RNA is used, it may be desired to convert the RNA to a complementary cDNA. In one embodiment, the RNA is whole-cell RNA and is used directly as the template for amplification. In other embodiments, the RNA may be polyadenylated mRNA. Purification of mRNA, for example, by affinity chromatography to oligo-dT columns, is well known in the art.

Pairs of primers that selectively hybridize to nucleic acids corresponding to specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax Technology; Bellus, 1994).

Following detection, one may compare the results seen in a given patient with a statistically significant reference group of normal patients and patients exhibiting a disease state. In this way, it is possible to correlate the amount of marker detected with various clinical states.

Primers

The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

Template-Dependent Amplification Methods

A number of template-dependent processes are available to amplify the marker sequences present in a given template sample. One of the best known amplification methods is the polymerase chain reaction (referred to as PCR), which is described in detail in U.S. Pat. Nos. 4,683,195, 4,683,202 and 4,800,159, and in Innis et al., 1990, each of which is incorporated herein by reference in its entirety.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in European Application No. 320, 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that may then be detected.

An isothermal amplification method in which restriction endonucleases and ligases are used to achieve the amplification of target molecules that contain nucleotide 5'-[alpha-thio]-triphosphates in one strand of a restriction site may also be useful in the amplification of nucleic acids in the present invention. Walker et al., Proc. Nat'l Acad. Sci. USA 89:392-396 (1992), incorporated herein by reference in its entirety.

Strand Displacement Amplification (SDA) is another method of carrying out isothermal amplification of nucleic acids that involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target-specific sequences may also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still other amplification methods described in GB Application No. 2 202 328 and in PCT Application No. PCT/US89/01025, each of which is incorporated herein by reference in its entirety, may be used in accordance with the present invention. In the former application, "modified" primers are used in a PCR-like template and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence-based amplification (NASBA) and 3SR (Kwoh et al., Proc. Nat'l Acad. Sci. USA 86:1173 (1989); Gingeras et al., PCT Application WO 88/10315, incorporated herein by reference in their entirety). In NASBA, the nucleic acids may be prepared for amplification by standard phenol/chloroform extraction, heat denaturation of a clinical sample, treatment with lysis buffer and minispin columns for isolation of DNA and RNA, or guanidinium chloride extraction of RNA. These amplification techniques involve annealing a primer that has target-specific sequences. Following polymerization, DNA/RNA hybrids are digested with RNase H, while double-stranded DNA molecules are heat denatured again. In either case, the single-stranded DNA is made fully double-stranded by addition of a second target-specific primer, followed by polymerization. The double-stranded DNA molecules are then multiply transcribed by a polymerase, such as T7 or SP6. In an isothermal cyclic reaction, the RNAs are reverse transcribed into double-stranded DNA, and transcribed once again with a polymerase, such as T7 or SP6. The resulting products, whether truncated or complete, indicate target-specific sequences.

Davey et al., European Application No. 329 822 (incorporated herein by reference in its entirety), disclose a nucleic acid amplification process involving cyclically synthesizing single-stranded RNA ("ssRNA"), single-stranded DNA ("ssDNA"), and double-stranded DNA ("dsDNA"), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety), disclose a nucleic acid sequence amplification scheme based on the hybridization of a promoter/primer sequence to a target single-stranded DNA ("ssDNA"), followed by transcription of many RNA copies of the sequence. This scheme is not cyclic, i.e., new templates are not produced from the resultant RNA transcripts. Other amplification methods include "race" and "one-sided PCR" (M. A. Frohman, in *PCR PROTOCOLS: A GUIDE TO METHODS AND APPLICATIONS*, Academic Press, N.Y. (1990), and Ohara et al., *Proc. Nat'l Acad. Sci. USA*, 86:5673-5677 (1989), each herein incorporated by reference in their entirety).

Methods based on ligation of two (or more) oligonucleotides in the presence of nucleic acid having the sequence of the resulting "di-oligonucleotide," thereby amplifying the di-oligonucleotide, may also be used in the amplification step of the present invention (Wu et al., *Genomics* 4:560 (1989), incorporated herein by reference in its entirety).

Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography that may be used in the present invention: adsorption, partition, ion-exchange and molecular sieve, and many specialized techniques for using them including column, paper, thin-layer and gas chromatography (Freifelder, 1982).

Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Antisense Constructs, Ribozymes and Small Interfering RNAs

Antisense

The term "antisense" refers to polynucleotide molecules complementary to a portion of a targeted gene or mRNA species. Complementary polynucleotides are those that are capable of base-pairing according to the standard Watson-Crick complementarity rules. That is, purines will base pair with pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or I, such as within a host animal, including a human subject.

The intracellular concentration of monovalent cations is approximately 160 mM (10 mM $Na^+$; 150 mM $K^+$). The intracellular concentration of divalent cations is approximately 20 mM (18 mM $Mg^+$; 2 mM $Ca^{++}$). The intracellular protein concentration, which would serve to decrease the volume of hybridization and, therefore, increase the effective concentration of nucleic acid species, is 150 mg/ml. Constructs may be tested for specific hybridization in vitro under conditions that mimic these in vivo conditions.

Antisense constructs may be designed to bind to the promoter and other control regions, exons, introns or even exon-intron boundaries of a gene. In certain embodiments, it is contemplated that effective antisense constructs may include regions complementary to the mRNA start site. In preferred embodiments, the antisense constructs are targeted to a sequence of an hnRNA and/or mRNA that is present in one PDE3A isoform and not in another. For example, one might target the 5' end of the mRNA encoding PDE3A1 (SEQ ID NO:14, SEQ ID NO:18), which is missing in the PDE3A2 mRNA (SEQ ID NO:15). One of ordinary skill in the art can readily test such constructs to determine whether levels of the target protein are affected.

As used herein, the terms "complementary" or "antisense" mean polynucleotides that are substantially complementary to the target sequence over their entire length and have very few base mismatches. For example, sequences of fifteen bases in length may be termed complementary when they have a complementary nucleotide at thirteen or fourteen nucleotides out of fifteen. Naturally, sequences that are "completely complementary" will be sequences that are entirely complementary throughout their entire length and have no base mismatches.

Other sequences with lower degrees of homology also are contemplated. For example, an antisense construct that has limited regions of high homology, but also contains a non-homologous region (e.g., a ribozyme) could be designed. These molecules, though having less than 50% homology, would bind to target sequences under appropriate conditions.

Although the antisense sequences may be full-length cDNA copies, or large fragments thereof, they also may be shorter fragments, or "oligonucleotides," defined herein as polynucleotides of 50 or less bases. Although shorter oligomers (8 to 20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45, 50 or 100 base pairs will be used. While all or part of the gene sequence may be employed in the context of antisense construction, statistically, any sequence of 14 bases long should occur only once in the human genome and, therefore, suffice to specify a unique target sequence.

In certain embodiments, one may wish to employ antisense constructs that include other elements, for example, those that include C-5 propyne pyrimidines. Oligonucleotides that contain C-5 propyne analogues of uridine and cytidine have been shown to bind RNA with high affinity and to be potent antisense inhibitors of gene expression (Wagner et al., 1993).

Alternatively, the antisense oligo- and polynucleotides according to the present invention may be provided as RNA via transcription from expression constructs that carry nucleic acids encoding the oligo- or polynucleotides. Throughout this application, the term "expression construct" is meant to include any type of genetic construct containing a nucleic acid encoding a product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by an RNA polymerase to initiate the specific transcription of a gene. The phrase "under transcriptional control" means that the promoter is in the correct location and orientation in relation to the nucleic acid to control RNA polymerase initiation.

The term promoter will be used herein to refer to a group of transcriptional control modules that are clustered around the initiation site for RNA polymerase II. Promoters are composed of discrete functional modules, each consisting of approximately 7 to 20 bp of DNA, and containing one or more recognition sites for transcriptional activator or repressor proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30 to 110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding the inhibitory polynucleotide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level transcription. The use of other viral or mammalian cellular or bacterial phage promoters that are well-known in the art is contemplated as well, provided that the levels of transcription and/or translation are sufficient for a given purpose.

Selection of a promoter that is regulated in response to specific physiologic signals can permit inducible expression of an antisense sequence. For example, a nucleic acid under control of the human PAI-1 promoter results in expression inducible by tumor necrosis factor. Additionally, any promoter/enhancer combination also could be used to drive expression of a nucleic acid according to the present invention. Tables 1 and 2 list elements/promoters that may be employed to regulate transcription and/or translation of operably coupled genes. This list is exemplary only and any known promoter and/or regulatory element may be used.

TABLE 1

| ENHANCER/PROMOTER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Prealbumin (Transthyretin) |
| Muscle Creatine Kinase |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |

TABLE 2

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X, poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, |
|  | Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Ribozymes

Another method for inhibiting the expression of specific PDE3A isoforms is via ribozymes. Ribozymes are RNA-protein complexes that cleave nucleic acids in a site-specific fashion. Ribozymes have specific catalytic domains that possess endonuclease activity (Kim and Cech, 1987). For example, a large number of ribozymes accelerate phosphoester transfer reactions with a high degree of specificity, often cleaving only one of several phosphoesters in an oligonucleotide substrate (Cech et at, 1981). This specificity has been attributed to the requirement that the substrate bind via specific base-pairing interactions to an internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases. Thus, sequence-specific ribozyme-mediated inhibition of gene expression may be particularly suited to therapeutic applications (Scanlon et al., 1991; Sarver et al., 1990; Sioud et al., 1992). It was reported that ribozymes elicited genetic changes in some cell lines to which they were applied. The altered genes included the oncogenes H-ras, c-fos and genes of HIV.

Several different ribozyme motifs have been described with RNA cleavage activity (Symons, 1992). Examples that are expected to function equivalently include sequences from the Group I self-splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozymes. Other suitable ribozymes include sequences from RNase P (Yuan et al., 1992; Yuan and Altman, 1994; U.S. Pat. Nos. 5,168,053 and 5,624,824), hairpin ribozyme structures (Berzal-Herranz et al., 1992; Chowrira et al., 1993) and Hepatitis Delta virus-based ribozymes (U.S. Pat. No. 5,625,047). The general design and optimization of ribozyme-directed RNA cleavage activity has been discussed in detail (Haseloff and Gerlach, 1988; Symons, 1992; Chowrira et al., 1994).

The other variable in ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence that is the cleavage site. For hammerhead ribozymes, the cleavage site is a dinucleotide sequence on the target RNA, a uracil (U) followed by either an adenine, cytosine or uracil (A, C or U) (Perriman et al., 1992).

The large number of possible cleavage sites in genes of moderate size, coupled with the growing number of sequences with demonstrated catalytic RNA cleavage activity, indicates that a large number of ribozymes that have the potential to down-regulate gene expression are available. Additionally, due to the sequence variation among different genes, ribozymes could be designed to specifically cleave individual genes or gene products. Designing and testing ribozymes for efficient cleavage of a target RNA is a process well known to those skilled in the art. Examples of scientific methods for designing and testing ribozymes are described by Chowrira et al., (1994), incorporated herein by reference.

Small Interfering mRNAs

Another possibility is to inhibit the translation of individual PDE3 mRNAs by RNA interference. This method of post-transcriptional gene silencing involves the use of a 21- or 22-nucleotide double-stranded synthetic RNA molecule homologous to a unique nucleotide sequence in the mRNA of interest. Through a mechanism yet to be determined, such small interfering RNA molecules (siRNAs) have the ability to reduce expression of the cognate protein. This approach has been used to reduce the expression of several cytoskeletal proteins. As noted above, a unique sequence in PDE3A1 mRNA (SEQ ID NO:14, SEQ ID NO:18) has been identified that may allow specific interference with the expression of PDE3A-136.

Methods for selectively interfering with gene expression using small interfering RNA species ("siRNA") are known in the art (e.g., Bass, 2001; Elbashir et al., 2001). Short, double-stranded RNAs (dsRNA) of about 30 bp or less that are homologous in sequence to a gene to be silenced (e.g., PDE3A) are introduced into a target cell (Elbashir et al., 2001). By a poorly understood endogenous pathway, the dsRNAs are broken into smaller fragments of about 21 to 22 bp (siRNAs). These fragments trigger the degradation of homologous mRNA sequences (Elbashir et al., 2001), e.g., PDE3A1 mRNA (SEQ ID NO:14, SEQ ID NO:18). Use of siRNAs can decrease expression of a target gene or even eliminate it entirely (Bass, 2001). Another advantage of siRNAs is that they are effective at lower concentrations (about 1 to 25 nM) than antisense constructs (Bass, 2001; Elbashir et al., 2001).

Transfection of 21 bp dsRNA sequences into NIH/3T3 cells, COS-7 cells and Hela S3 cells using cationic liposomes resulted in inhibition of homologous reporter genes (Elbashir et al., 2001). The effectiveness of inhibition appeared to be inversely related to the expression levels of the target gene, with highly expressed genes showing less inhibition by siRNA constructs (Elbashir et al., 2001). Because the PDE3 genes are expressed at relatively low levels compared to highly expressed mammalian genes, the use of siRNA inhibitors should prove effective at inhibiting or eliminating expression of targeted PDE3 isoforms.

Expression Vectors

Nucleic acids encoding PDE3 isoform proteins or peptides may be incorporated into expression vectors for production of the encoded proteins or peptides. Non-limiting examples of expression systems known in the art include bacteria such as

*E. coli*, yeast such as *Pichia pastoris*, baculovirus, and mammalian expression systems such as in COS or CHO cells. A complete gene can be expressed or, alternatively, fragments of the gene encoding portions of polypeptide can be produced.

The gene or gene fragment encoding a polypeptide may be inserted into an expression vector by standard subcloning techniques. An *E. coli* expression vector may be used that produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6xHis system add only short sequences, both of which are known to be poorly antigenic and which do not adversely affect folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See U.S. Pat. No. 4,215,051 (incorporated herein by reference).

Amino acid sequence variants of the polypeptide may also be prepared. These may, for instance, be minor sequence variants of the polypeptide that arise due to natural variation within the population or they may be homologues found in other species. They also may be sequences that do not occur naturally but are sufficiently similar so that they function similarly and/or elicit an immune response that cross-reacts with natural forms of the polypeptide. Sequence variants may be prepared by standard methods of site-directed mutagenesis such as those described herein.

Substitutional variants typically contain an alternative amino acid at one or more sites within the protein, and may be designed to modulate one or more properties of the polypeptide such as stability against proteolytic cleavage. Substitutions preferably are conservative, that is, one amino acid is replaced with one of similar size and charge. Conservative substitutions are well known in the art and include, for example, the changes of: arginine to lysine; asparagine to glutamine or histidine; aspartate to glutamate; cysteine to serine; glutamine to asparagine; glutamate to aspartate; histidine to asparagine or glutamine; isoleucine to leucine or valine; leucine to valine or isoleucine; lysine to arginine or glutamine; methionine to leucine or isoleucine; phenylalanine to tyrosine; serine to threonine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte and Doolittle, 1982); these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity (U.S. Pat. No. 4,554,101, incorporated herein by reference). The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Insertional variants include fusion proteins such as those used to allow rapid purification of the polypeptide and also may include hybrid proteins containing sequences from other proteins and polypeptides that are homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells that do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention, one would prepare an expression vector that comprises one of the claimed isolated nucleic acids under the control of, or operatively linked to, one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used (Stinchcomb et al., 1979; Kingsman et al., 1979; Tschemper et al., 1980). This plasmid already contains the trp1 gene that provides a selection marker for a mutant strain of yeast lacking the ability to grow in tryptophan, for example, ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, the aforementioned glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographa californica* nuclear polyhidrosis virus (AcNPV) is used as a vector to express foreign genes. The virus grows in *Spodoptera frugiperda* cells. The isolated nucleic acid coding sequences are cloned into non-essential regions (for example, the polyhedrin gene) of the virus and placed under control of an AcNPV promoter (for example, the polyhedrin promoter). Successful insertion of the coding sequences results in the inactivation of the polyhedrin gene and production of non-occluded recombinant virus (i.e., virus lacking the protein coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter, the vaccinia virus 7.5K promoter). Further, it is also possible, and may be desirable, to utilize promoter or control sequences normally associated with the desired gene sequence, provided such control sequences are compatible with the host cell systems.

A number of viral-based expression systems may be utilized; for example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for one to two days in an enriched media, and then are switched to a selective media. The selectable marker in the recombinant plasmid confers resistance to the selection and allows cells to stably integrate the plasmid into their chromosomes and grow to form foci, which in turn may be cloned and expanded into cell lines.

A number of selection systems may be used including, but not limited to, the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, site-directed mutagenesis is performed by first obtaining a single-stranded vector, or melting of two strands of a double-stranded vector that includes within its sequence a DNA sequence encoding the desired protein. An oligonucleotide primer bearing the desired mutated sequence is synthetically prepared. This primer is then annealed with the single-stranded DNA preparation and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

Phage Display

In certain embodiments, it may be desirable to use random amino acid sequences in the form of a phage display library for use as potential isoform-selective PDE3 inhibitors or activators. The phage display method has been used for a variety of purposes (see, for example, Scott and Smith, 1990, 1993; U.S. Pat. Nos. 5,565,332, 5,596,079, 6,031,071 and 6,068,829, each incorporated herein by reference).

Generally, a phage display library is prepared by first constructing a partially randomized library of cDNA sequences, encoding a large number of amino acid combinations. The cDNA sequences are inserted in frame into, for example, a viral coat protein for a phage such as the fuse 5 vector (U.S. Pat. No. 6,068,829). The cDNAs are expressed as random amino acid sequences, incorporated into a coat protein. The randomized peptides are thus displayed on the external surface of the phage, where they can bind to proteins or peptides. Phage binding to PDE3 proteins or peptides may be separated from unbound phage using standard methods, for example, by affinity chromatography to PDE3 peptides covalently linked to a solid support such as a membrane or chromatography beads. If desired, it is possible to collect bound phage, detach them from the PDE3 peptides by exposure to an appropriate solution and proceed with another round of binding and separation. This iterative process results in the selection of phage with an increased specificity for PDE3.

Once phage of an appropriate binding stringency have been obtained, it is possible to determine the amino acid sequence of the binding peptide by sequencing the portion of the phage genome containing the cDNA, for example, by using PCR primers that flank the cDNA insertion site. Phage lacking any cDNA insert may be used as a control to ensure that binding is specific.

The skilled artisan will realize that phage display may be used to select for peptides (between 3 and 100, more preferably between 5 and 50, even more preferably between 7 and 25, amino acid residues long) that can bind to a desired protein or peptide. Such peptides may be of use, for example, as potential inhibitors or activators of PDE3 catalytic activity or protein-protein binding.

Methods for Screening Active Compounds

The present invention also contemplates the use of PDE3 isoform proteins, peptides and active fragments, and nucleic acids encoding PDE3, in the screening of potential PDE3 inhibitors or activators. These assays may make use of a variety of different formats and may depend on the kind of "activity" for which the screen is being conducted. Contemplated functional "read-outs" include binding to a substrate (e.g., cAMP or cGMP), inhibition of binding to a membrane or another protein, phosphorylation or dephosphorylation of PDE3, or inhibition or stimulation of a variety of cAMP-dependent processes, such as calcium channel activation or protein kinase activity.

In Vitro Assays

In one embodiment, the invention is to be applied for the screening of compounds that bind to the PDE3 isoforms or a fragment thereof. The polypeptide or fragment may be either free in solution, fixed to a support, or expressed in or on the surface of a cell. Either the polypeptide or the compound may be labeled, thereby permitting the determination of binding.

In another embodiment, the assay may measure the inhibition of binding of PDE3 to a natural or artificial substrate or binding partner. Competitive binding assays can be performed in which one of the agents is labeled. Usually, the polypeptide will be the labeled species. One may measure the amount of free label versus bound label to determine binding or inhibition of binding.

Another technique for high throughput screening of compounds is described in WO 84/03564, the contents of which are incorporated herein by reference. Large numbers of small peptide test compounds are synthesized on a solid substrate, such as plastic pins or some other surface. The peptide test compounds are reacted with PDE3 and washed. Bound polypeptide is detected by various methods.

Purified PDE3 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the PDE3 active region to a solid phase.

Various cell lines containing wild-type or natural or engineered mutations in PDE3 can be used to study various functional attributes of these proteins and how a candidate compound affects these attributes. Methods for engineering mutations are described elsewhere in this document. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of PDE3 or related pathways may be explored. This may involve assays such as those for phosphorylation states of various molecules, cAMP levels, mRNA expression for CREB-linked genes, or any other process regulated in whole or in part by PDE3 activity. For certain embodiments, it may be desirable to create "knock-out" cells that are lacking in endogenous phosphodiesterase activity in order to specifically assay the effects of various compounds on inserted isoforms of PDE3.

In Vivo Assays

The present invention also encompasses the use of various animal models. By developing or isolating mutant cells lines that show differential expression of one or more PDE3 isoforms, one can generate animal models that will be predictive of cardiomyopathy and/or pulmonary hypertension in humans and other mammals. These models may employ transgenic animals that differentially express one or more PDE3 isoforms.

Treatment of animals with test compounds will involve the administration of the compound, in an appropriate form, to the animal. Administration will be by any route that could be utilized for clinical or non-clinical purposes including, but not limited to, oral, nasal, buccal, rectal, vaginal or topical. Alternatively, administration may be by intratracheal instillation, bronchial instillation, intradermal, subcutaneous, intramuscular, intraperitoneal, intravenous or intra-arterial injection.

Determining the effectiveness of a compound in vivo may involve a variety of different criteria. Such criteria include, but are not limited to: survival, increased cardiac output, increased ventricular ejection fraction, reduced pulmonary arterial pressure, improved exercise tolerance, improved quality-of-life index, reduced incidence of myocardial ischemia or infarction, reduced incidence of ventricular ectopic activity or arrhythmia, reduced or increased blood pressure, decreased myocardial mass (reduced hypertrophy), reduced vascular hyperplasia, reduced vascular resistance, reduced platelet aggregation.

Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs that are more active or stable than the natural molecules, which have different susceptibility to alteration or which may affect the function of various other molecules. In one approach, one would generate a three-dimensional structure for PDE3 or a fragment thereof. This could be accomplished by x-ray crystallography, computer modeling based on the 3-D structures of other phosphodiesterases or by a combination of both approaches. In addition, knowledge of the polypeptide sequences permits computer-employed predictions of structure-function relationships. An alternative approach, an "alanine scan," involves the random replacement of residues throughout a protein or peptide molecule with alanine, followed by determining the resulting effect(s) on protein function.

It also is possible to isolate a PDE3-specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of an anti-idiotype antibody would be expected to be an analog of the original antigen. The anti-idiotype could then be used to identify and isolate peptides from banks of chemically or biologically produced peptides. Selected peptides would then serve as the pharmacore. Anti-idiotypes may be generated using the methods described herein for producing antibodies, using an antibody as the antigen.

Thus, one may design drugs that have improved PDE3 isoform-selective activity or that act as stimulators, inhibitors, agonists, or antagonists of PDE3.

Knock-Out

The technique known as homologous recombination allows the precise modification of existing genes, including the inactivation of specific genes, as well as the replacement of one gene for another. Methods for homologous recombination are described in U.S. Pat. No. 5,614,396, incorporated herein by reference.

Homologous recombination relies on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

First, a site for integration is selected within the host cell, such as the PDE3A or PDE3B genes. Sequences homologous to the integration site are included in a genetic construct, flanking the selected gene to be integrated into the genome. "Flanking," in this context, simply means that target homologous sequences are located both upstream (5') and downstream (3') of the selected gene. The construct is then introduced into the cell, permitting recombination between the cellular sequences and the construct.

It is common to include within the construct a selectable marker gene. This gene permits selection of cells that have integrated the construct into their genomic DNA by conferring resistance to various biostatic and biocidal drugs. In addition, this technique may be used to "knock-out" (delete) or interrupt a particular gene. Thus, another approach for inhibiting gene expression involves the use of homologous recombination, or "knock-out technology." This is accomplished by including a mutated or vastly deleted form of the heterologous gene between the flanking regions within the construct. The arrangement of a construct to effect homologous recombination might be as follows:

vector•5'-flanking sequence•selected gene•selectable marker gene•flanking sequence-3'•vector Using this kind of construct, it is possible, in a single recombinatorial event, to (i) "knock out" an endogenous gene, (ii) provide a selectable marker for identifying such an event, or (iii) introduce a transgene for expression.

Another refinement of the homologous recombination approach involves the use of a "negative" selectable marker. One example of the use of the cytosine deaminase gene in a negative selection method is described in U.S. Pat. No. 5,624,830. The negative selection marker, unlike the selectable marker, causes death of cells that express the marker. Thus, it is used to identify undesirable recombination events. When seeking to select homologous recombinants using a selectable marker, it is difficult in the initial screening step to identify proper homologous recombinants from recombinants generated from random, non-sequence-specific events. These recombinants also may contain the selectable marker gene and may express the heterologous protein of interest, but will, in all likelihood, not have the desired phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

Formulations and Routes for Administration to Patients

In certain embodiments, the isoform-selective inhibitors or activators of PDE3 may be used for therapeutic treatment of medical conditions, such as dilated cardiomyopathy and/or pulmonary hypertension. Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

Aqueous compositions of the present invention comprise an effective amount of PDE3 inhibitor or activator, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the PDE3 inhibitors or activators of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions normally would be administered as pharmaceutically acceptable compositions.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

The compositions of the present invention may be formulated in a neutral or salt form. Pharmaceutically acceptable salts include the acid addition salts that are formed by reaction of basic groups with inorganic acids such as, for example, hydrochloric or phosphoric acids, or such organic acids as acetic, oxalic, tartaric, mandelic, and the like. Salts formed with free acidic groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion (see, for example, *Remington's Pharmaceutical Sciences*, 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics' standards.

EXAMPLES

The following examples are included to demonstrate preferred embodiments of the invention. It should be appreciated by those of skill in the art that the techniques disclosed in the Examples that follow represent techniques discovered by the inventors to function well in the practice of the invention and, thus, can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Materials and Methods

Preparation of rtPDE3A1

A human myocardial PDE3A construct was generated by inserting an eight amino acid Flag epitope (Asp-Tyr-Lys-Asp-Asp-Asp-Asp-Lys) immediately upstream from the stop codon of PDE3A1 (SEQ ID NO:14). Using 50 ng PDE3A1 cDNA as template (GenBank accession number NM_000921), PCR amplification was performed in a Gene-Amp PCR system (Perkin Elmer, Wellesley, Mass.) with Pfu polymerase (Stratagene, La Jolla, Calif.) using 3 pmol each of sense primer corresponding to nt 3009-3027 of the PDE3A1 ORF:

CTTCATCTCTCACATTGTGGGGCCTCTGTG (SEQ ID NO:4) and antisense primer corresponding to nt 3423-3403 and the Flag epitope:

TTTGCGGCCGCCTCGAGTTATTTATCAT-CATCATCTTTATAATCC TGGTCTGGCTTTTGGT-TGG (SEQ ID NO:5).

The resulting PCR product contained a unique PDE3 DraIII site at the 5' end and a stop codon at the 3' end. The stop codon was flanked upstream by a Flag epitope-coding sequence and downstream by an XhoI site. The PCR products were subcloned into the pCRII vector (Invitrogen, Carlsbad, Calif.) and isolated from this vector as DraIII/XhoI fragments. XhoI/DraIII fragments containing the ORF sequence of PDE3A1 (SEQ ID NO:14) upstream from the unique DraIII site were restricted from pBluescript. In a three-way ligation, these 5' XhoI/DraIII fragments were ligated via the DraIII site to the 3' DraIII/XhoI Flag epitope-containing fragments and to XhoI-cut pZero vector (Invitrogen), to give PDE3A1 Flag-pZero. PDE3A1-Flag was then excised from pZero with XhoI, ligated into pAcSG2 vector, subcloned and amplified.

PDE3A1-Flag-pAcSG2 plasmid (2 µg) was co-transfected with linearized BaculoGold DNA into Sf21 cells (BaculoGold transfection kit; Pharmingen, San Diego, Calif.). After five days, fresh Sf21 cells (10-20)×$10^6$ cells per 75 $cm^2$ flask, grown in TNM-FH media (BD-Pharmingen, San Diego, Calif.), were infected with medium containing PDE3A1-Flag baculovirus. For amplification, 100-500 µl of medium was collected after 72 to 96 hours and used to infect fresh cultures, after which viral titers were determined by twelve-well end-point dilution assay. Cells from 75 $cm^2$ flasks, usually 10-20×$10^6$ cells per flask, were sedimented for ten minutes at 1000× g, washed twice with ice-cold PBS and resuspended in 10 mM HEPES, 1 mM EDTA, 250 mM sucrose, 10 mM pyrophosphate, 5 mM NaF, 1 mM PMSF, 1 mM sodium orthovanadate, 1% NP-40 and 10 µg/ml each of aprotinin, leupeptin and pepstatin. Lysates were prepared by sonication on ice (two 20-second pulses, output 2, 40% of cycle) with a Sonifier Cell Disruptor 350 (Branson Sonic Power, Danbury, Conn.). Lysates were sedimented for ten minutes at 12,000×g; supernatant fractions were used for Western blotting. C-terminally Flag-tagged rtPDE3A1 was purified to apparent homogeneity by immunoprecipitation with anti-Flag antibodies followed by competitive release with Flag peptide.

Preparation of Subcellular Fractions of Human Myocardium and Cultured Aortic Myocytes Cytosolic and KCl-washed microsomal fractions, from the left ventricular myocardium of explanted hearts of cardiac transplant recipients with idiopathic dilated cardiomyopathy, were prepared by homogenization, differential sedimentation and high-salt washing. Each preparation was made from tissue pooled from at least three different hearts. Tissue from left ventricular free walls was trimmed of epicardium and endocardium, cut into roughly 0.5 $cm^3$ pieces, rapidly frozen in liquid nitrogen, and stored at −80° C. until use. To prepare subcellular fractions, 0.3 g of the frozen tissue were added to five volumes of buffer (5 mM KH2PO4/K2HPO4 and 2 mM EDTA (pH 6.8, 4° C.), 1 mM dithiothreitol, 1 mM benzamidine, 0.8 mM PMSF, and 1 µg/ml each of pepstatin A, leupeptin, and antipain). The tissue was homogenized twice for ten seconds each. The homogenate was sedimented at 14,000 rpm for 20 minutes using an Eppendorf Model 5415 centrifuge. The supernatant was saved and the pellet resuspended in 1.5 ml of buffer, then rehomogenized and resedimented in order to solubilize any trapped cytosolic proteins. The supernatants containing cytosolic proteins were pooled and diluted 1:1 with buffer containing 40% v/v glycerol and stored at −80° C. until use. Comparable fractions of cultured human aortic myocytes (Clonetics, East Rutherford, N.J.; seventh passage) were similarly prepared.

Western Blotting

Lysates of Sf21 cells expressing rtPDE3A1 and subcellular fractions of human myocardium and aortic myocytes were precipitated with trichloroacetic acid (final concentration 50%), dissolved in SDS buffer, subjected to SDS-PAGE (8% acrylamide) and transferred electrophoretically to nitrocellulose membranes (Schleicher and Schuell, Kenne, N.H.). After transfer, membranes were blocked, washed and incubated for at least two hours at room temperature with polyclonal antibodies raised against synthetic peptides whose sequences correspond to selected regions of the open reading frame of PDE3A1 (SEQ ID NO:14). The polyclonal antibodies corresponded to N-terminal amino acids 29-42 (anti-NT), mid-sequence amino acids 424-460 (anti-MID), and C-terminal amino acids 1125-1141 (anti-CT) of PDE3A1 (see SEQ ID NO:1). Immunoreactive bands were detected with a horseradish peroxidase-conjugated second antibody (Promega, Madison, Wis.) and an enhanced chemiluminescence luminescent reagent (Pierce, Rockford, Ill.) in accordance with the manufacturer's instructions.

Expression of rtPDE3A1 Isoforms by In Vitro Transcription/Translation

The entire coding region of PDE3A1 cDNA (SEQ ID NO:14) was inserted into pBluescript. In addition, a plasmid with an ATGATG to CTGCTG mutation (Met-Met>Leu-Leu) at nt 1450-5 (ATG7/8) was generated by PCR using a QuikChange Site-Directed Mutagenesis kit (Stratagene, La Jolla, Calif.). The sense primer GGAATAATCCAGTGCTGCTGACCCTCACCAAAAGCAGATCC (SEQ ID NO:6) and the complementary anti-sense primer (corresponding to nt 1435-76 of the PDE3A1 ORF—SEQ ID NO:14) were used for mutagenesis. After amplification in E. coli (XL1-Blue), mutated plasmids were purified using a QIAprep Spin Miniprep kit (Qiagen, Valencia, Calif.) and sequenced.

PCR products with different five deletions were generated from the wild-type and mutated pBluescript-PDE3A1 plasmids using five sense primers containing T7 promoter sites immediately upstream from gene-specific sequences and an anti-sense primer containing the stop codon and a poly-A tail. The sense primers used for amplification in these reactions were as follows:

TAATACGACTCACTATAGGGAGTGAA-
    GAGGGCACCCTATAC CATGGCAG (SEQ ID NO:7)
TAATACGACTCACTATAGGGT-
    TCAGTCTCCTGTGTGCCTTCT TCTGGATG (SEQ ID NO:8)
TAATACGACTCACTATAGGG-
    GAAGCGCTCGTCCAGATTGGG CTGGGC (SEQ ID NO:9)
TAATACGACTCACTATAGGGTGGAGAC-
    CTTACCTGGCGTAC CTGTCC (SEQ ID NO:10)
TAATACGACTCACTATAGGGACTGCAG-
    GAAGCACCTTCATC CAGTCC (SEQ ID NO:11)

The primers correspond, respectively, to nucleotides (−)22 to (−)7 in the 5-untranslated region, nucleotides 409-438, nucleotides 511-537, nucleotides 706-732, and nucleotides 1401-1427 of the open reading frame of PDE3A1 (SEQ ID NO:14, GenBank Accession No. NM000921). In each case, the antisense primer, corresponding to nucleotides 3400-3426 of PDE3A1 (SEQ ID NO:14), was: TTTTTTTTTTTTTTTTTTTTCACTG-GTCTGGCTTTTGGGTTGGTAT (SEQ ID NO:12).

In vitro translation products were synthesized from the PCR fragment templates and labeled with 4 µCi [$^{35}$S]methionine (1000 Ci/mmol) in reticulocyte lysates using the TnT T7 Quick for PCR DNA system (Promega, Madison, Wis.). To make a synthetic protein, a PCR product containing a 5 deletion and a T7 promoter sequence was added to the TnT T7 PCR Quick Master Mix and incubated for roughly 60 to 90 minutes at 30° C. This process was repeated for each PCR construct containing a 5 deletion. Proteins thus created were isolated and subsequently analyzed by autoradiography.

5' RACE

PCR amplification was performed on Marathon RACE-Ready cDNA from human myocardium (Clontech, Palo Alto, Calif.) using 1 pmol gene-specific anti-sense primer and 1 pmol sense primer corresponding to the 5' end of the manufacturer's 5' tag. A second round of PCR was performed for 35 cycles using 1 pmol nested gene-specific primer and 1 pmol nested sense primer corresponding to a second sequence within the manufacturer's tag. RACE products were purified on agarose gels and ligated into the pCR2.1 vector with T4 ligase (14° C. overnight) using a TA cloning kit (Invitrogen, San Diego, Calif.). Competent cells (INV F') were transformed using a One Shot Kit (Invitrogen, Austin, Tex.) and plated on X-gal LB-ampicillin plates (100 µg/ml ampicillin). Positive colonies were grown overnight in LB-ampicillin medium. Plasmids were purified using Mini- or Midiprep Plasmid purification systems (Qiagen) and inserts were excised with EcoRI. Insert sizes were estimated by electrophoresis through agarose gels.

Southern and Northern Blotting

DNA probes were prepared from PDE3A1 plasmid by PCR using region-specific primers. PCR products were purified using QIA Quick Kits (Qiagen). DNA was labeled with [$^{32}$P]dCTP (3000 Ci/mmol, 10 mCi/ml) using a random primer labeling kit (Stratagene). Unincorporated nucleotides were removed using Sepahadex G-50 (fine) columns (Roche, Indianapolis, Ind.). For Southern blotting, linear DNA corresponding to nt (−)268 to nt 2610 of the PDE3A1 ORF (SEQ ID NO:14, SEQ ID NO:18) was prepared from PDE3A1 template by PCR and purified as described above. The PCR product was quantified by measurement of the A260/A280 ratio and its purity confirmed by agarose gel electrophoresis. PCR product samples were subjected to electrophoresis on 0.7% agarose gels, transferred to Gene Screen Plus Nylon Membranes (New England Nuclear, Boston, Mass.), cross-linked and pre-hybridized for two to three hours in QuikHyb (Stratagene). Labeled DNA probes were hybridized with DNA blots at 65° C. for three to four hours using 1.25×10$^6$ cpm/ml of probe and 0.1 mg/ml salmon sperm DNA. Following hybridization, excess radiolabeled probe was removed by rinsing in SSC/0.1% SDS and autoradiography was performed at −80° C. For Northern blotting, RNA was extracted from human left ventricular myocardium from the excised hearts of transplant recipients with dilated cardiomyopathy using TRI reagent (Molecular Research Center, Cincinnati, Ohio). PolyA RNA was prepared from total RNA using a Message Maker kit (Life Technologies, Rockville, Md.). RNA was quantified and its purity confirmed as described above. PolyA RNA samples were subjected to electrophoresis on 1% agarose 0.5 M formaldehyde gels, transferred to Gene Screen Plus Nylon Membranes, cross-linked and pre-hybridized for two to three hours in QuikHyb. Labeled DNA probes were hybridized with RNA blots, excess radiolabeled probe was removed.

Example 2

PDE3 Isoforms in Cardiac and Vascular Myocytes

It has been shown that proteins of three different apparent molecular weights can be immunoprecipitated from mammalian myocardium with anti-PDE3 antibodies (Smith et al., 1993). These proteins are identified herein as PDE3 isoforms by Western blotting of cytosolic and microsomal fractions of human myocardium, using antibodies raised against peptides derived from the PDE3A ORF.

An antibody against the C-terminus of PDE3 ("anti-CT") reacted with three proteins in these fractions (FIG. 5). The largest, with an apparent MW of 136,000 on SDS-PAGE ("PDE3A-136"), was present exclusively in microsomal fractions (FIG. 5). Another PDE3 isoform, with an apparent MW of 118,000 ("PDE3A-118"), was present in both microsomal and cytosolic fractions, as was a third isoform with an apparent MW of 94,000 ("PDE3A-94") (FIG. 5).

An antibody against an amino acid sequence between NHR2 and CCR ("anti-MID") reacted with PDE3A-136 and PDE3A-118 but not PDE3A-94 (FIG. 5). An antibody against amino acids 25-49 ("anti-NT") did not react with any protein in microsomal or cytosolic fractions, indicating the absence of this region from cardiac and vascular PDE3 isoforms (FIG. 5). However, anti-NT did react with an rtPDE3A1 containing the full-length ORF (FIG. 5).

The antibodies were used to identify PDE3 isoforms in subcellular fractions of aortic myocytes (Choi et al., 2001). Anti-CT reacted with 94-kDA and 118-kDa proteins in microsomal and cytosolic fractions of aortic myocytes (not shown). Anti-MID reacted only with the 118-kDa proteins (not shown). No proteins were visualized with anti-NT, and the 136-kDa protein band was absent in all cases (not shown).

Western blotting was used to show that PDE3B is present in vascular myocytes, where it appears as a 137-kDa band in the microsomal fraction (PDE3B-137) (Liu and Maurice, 1998). Western blots (not shown) indicate PDE3B-137 is absent from myocardium (not shown). These results are summarized in Table 3.

TABLE 3

Distribution of PDE3 isoforms in cardiac and vascular myocytes

| Cell/tissue | Fraction | PDE3A-136 | PDE3A-118 | PDE3A-94 | PDE3B-137 |
|---|---|---|---|---|---|
| Cardiac | Microsomes | + | + | + | |
| | Cytosol | | + | + | |
| Vascular | Microsomes | | + | + | + |
| | Cytosol | | + | + | |

All three polyclonal antibodies (anti-NT, anti-MID and anti-CT) reacted with recombinant PDE3A1. Anti-CT reacted with proteins in the cytosolic and microsomal fractions of human myocardium that had apparent molecular weights of 94,000 Da and 118,000 Da. Anti-CT also reacted with a protein with an apparent molecular weight of 136,000 Da that was seen only in microsomal myocardial fractions. Anti-MID also reacted with the 118,000 and 136,000 proteins, but not the 94,000 Da protein.

Example 3

Mechanisms for Generating Cardiac and Vascular PDE3A Isoforms

Addition of [$^{35}$S]-labeled rtPDE3A (full-length ORF, SEQ ID NO:14) to a sample of human myocardium prior to the preparation of cytosolic and microsomal fractions provided no evidence for the generation of smaller isoforms by proteolysis of the labeled full-length rtPDE3A (not shown). Other potential mechanisms were investigated.

Figure 6:
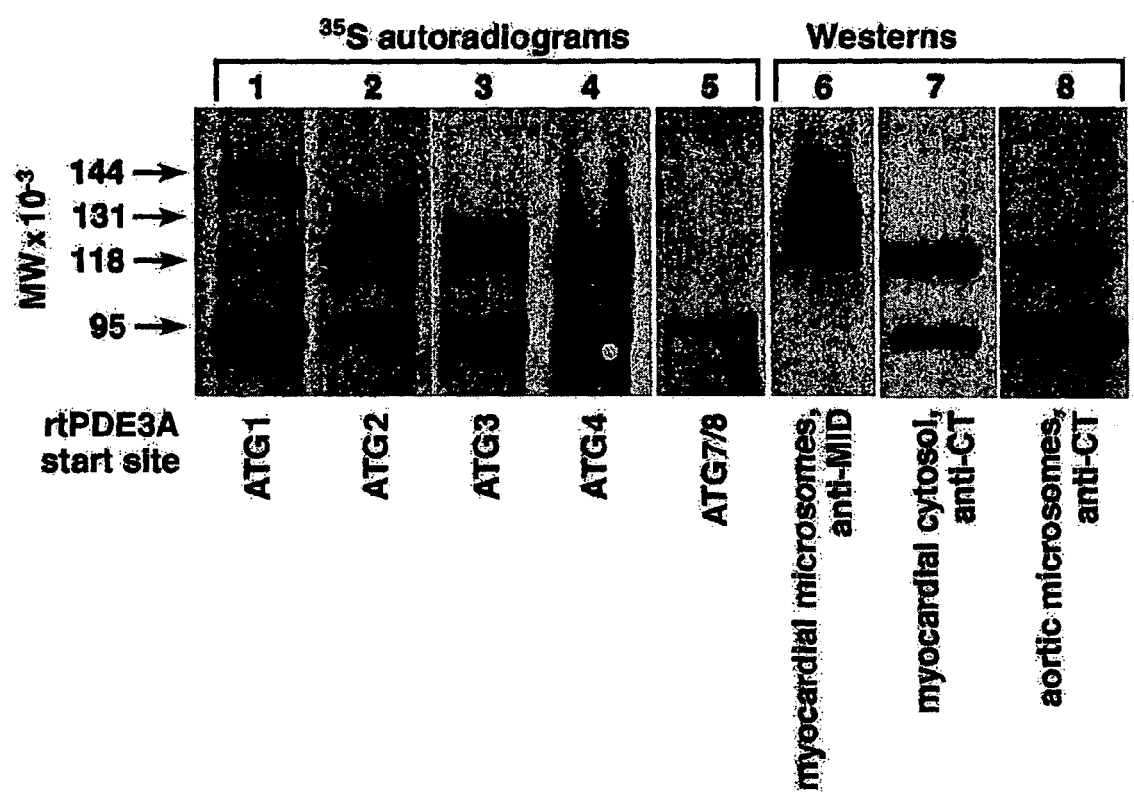
FIG. 6: Comparison of molecular weights of [$^{35}$S]-labeled rtPDE3A proteins, showing SDS-PAGE autoradiograms, and native cardiac and aortic isoforms of PDE3A, identified by Western blotting of membranes prepared from the same gels with antibodies as indicated. The numbers below the autoradiograms indicate the initial start codon of the PDE3A-derived construct.

The migration of cardiac and vascular isoforms of PDE3A were compared to those of recombinant proteins generated by in vitro transcription/translation. PDE3A constructs were prepared with 5' deletions designed to yield rtPDE3As starting from different in-frame ATGs, inserted downstream from a T7 promoter and Kozak sequence (FIG. 3). PDE3A-136, PDE3A-118 and PDE3A-94 migrated with the same apparent molecular weights as the rtPDE3As starting at ATGs 1507, 1969 and 2521, respectively (FIG. 6). This is consistent with the three PDE3A isoforms being generated by transcription from alternative start sites. Transcription/translation from every PDE3A-derived construct generated an rtPDE3A whose apparent MW corresponded to PDE3A-94. To determine whether the latter might be generated by translation from a downstream AUG, a full-length rtPDE3A construct was prepared in which the ATG at nt 2521 was mutated to CTG (M to L). This mutation resulted in the disappearance of rtPDE3A-94 (not shown). It is concluded that the PDE3A-94 isoform is generated by transcription from the ATG initiation codon at nt 2521.

Figure 7:
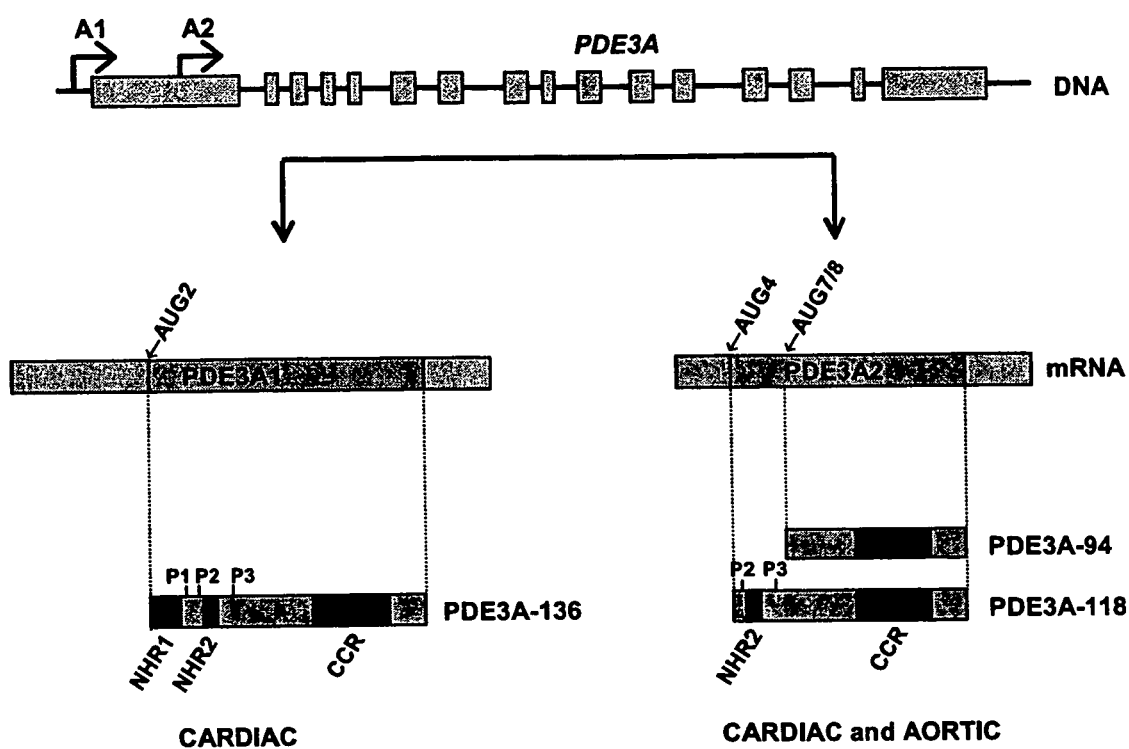
FIG. 7: Generation of cardiac and aortic isoforms of PDE3A. PDE3A1 and PDE3A2 mRNAs were generated by alternative transcription. PDE3A1 is expressed only in cardiac myocytes. PDE3A2 is expressed in both cardiac and aortic myocytes. PDE3A-136 is translated from PDE3A1. PDE3A-118 and PDE3A-94 are translated from alternative sites in PDE3A2. Numbers in "mRNA" refer to start codons. P1, P2 and P3 designate phosphorylation sites.

At least two different messenger RNA species are expressed in different tissues: PDE3A1 mRNA (SEQ ID NO:14, SEQ ID NO:18) in cardiac myocytes and PDE3A2 mRNA (SEQ ID NO:15) in both cardiac and vascular myocytes (Choi et al., 2001). It appears that transcription from alternative start sites in PDE3A results in the expression of PDE3A1 mRNA (SEQ ID NO:14, SEQ ID NO:18) in cardiac myocytes and of PDE3A2 mRNA (SEQ ID NO:15) in cardiac and vascular myocytes. From the above results, it is concluded that PDE3A-136 is generated in cardiac myocytes by translation from the second AUG in PDE3A1 mRNA (SEQ ID NO:14), while PDE3A-118 and PDE3A-94 are generated in cardiac and vascular myocytes by translation from alternative downstream AUGs in PDE3A2 mRNA (SEQ ID NO:15) (FIG. 7).

Example 4

Structure-Function Relationships in PDE3A Isoforms

FIG. 11 shows the complete amino acid sequence of the open reading frame (ORF) for PDE3A. To date, three isoforms of PDE3A have been characterized. These are apparently generated by N-terminal truncation of the PDE3A ORF (SEQ ID NO:14). The apparent N-terminal methionine residues of the three isoforms are indicated in bold in FIG. 11. Those are located at residues 146 for PDE3A-136, 300 for PDE3A-118 and either 484 or 485 for PDE3A-94. The locations of the phosphorylation sites on the PDE3A isoforms are indicated by underlining in FIG. 11. The P1 site is located at residues 288-294, the P2 site at residues 309-312 and the P3 site at residues 435-438. The P2 and P3 sites on the PDE3A isoforms contain a single serine residue and the phosphorylated amino acid is unambiguous. The P1 site contains multiple serine residues and it is presently unknown which of these is covalently modified by phosphorylation.

Example 5

Functional Domains of PDE3A Isoforms

Figure 12:
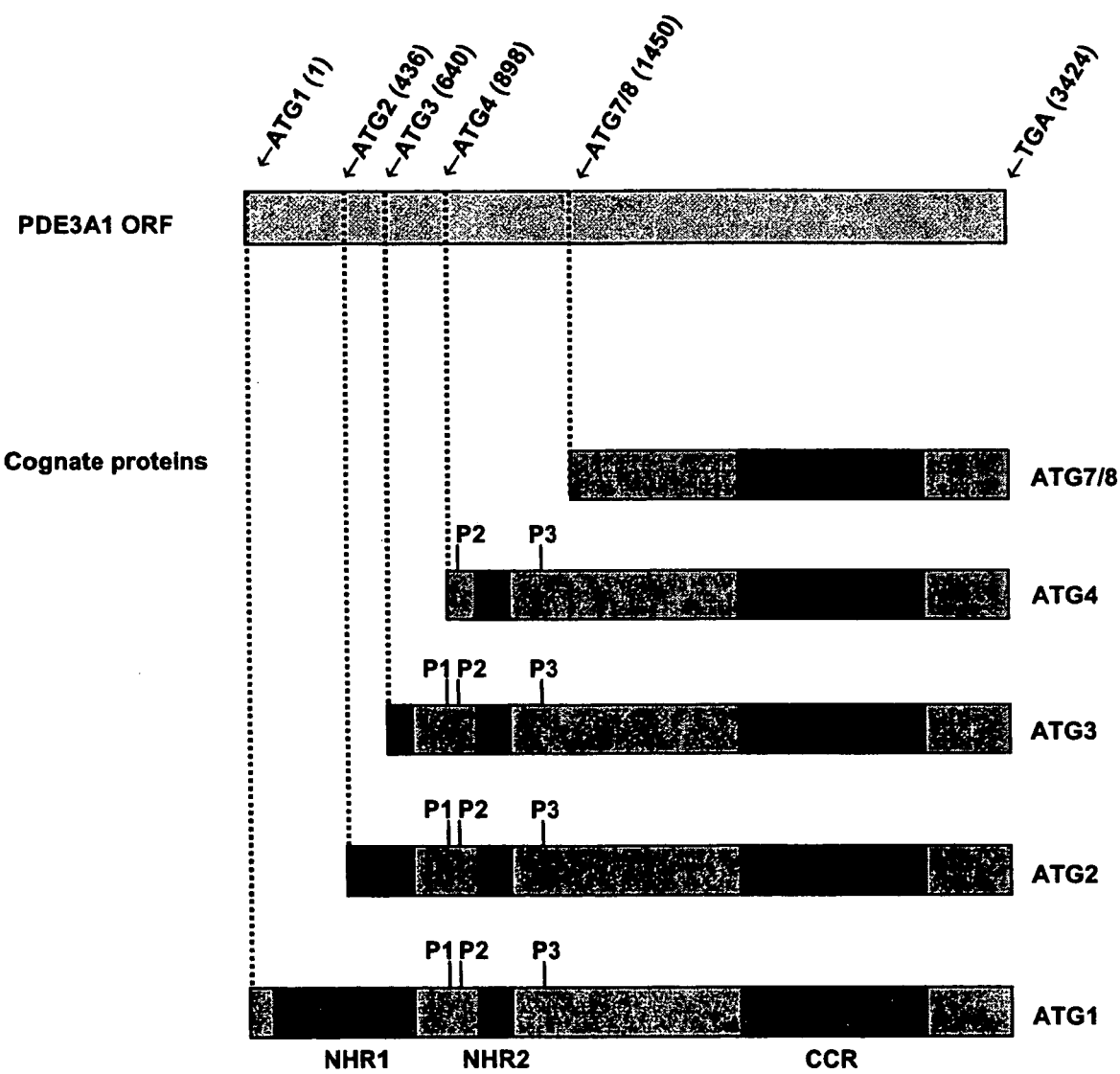
FIG. 12: Comparison of apparent molecular weights of [$^{35}$S] rtPDE3A proteins and native cardiac and aortic isoforms of PDE3A. rtPDE3A isoforms were generated by in vitro transcription/translation from constructs with 5' deletions designed to result in translation from different in-frame AUG codons in the PDE3A1 ORF.

The functional domains in the cardiac and vascular isoforms of PDE3 are shown in Table 4. The domains were elucidated in part by comparison of the electrophoretic migration, via SDS-PAGE, of native PDE3 isoforms and recombinant PDE3A isoforms generated by in vitro transcription/translation from constructs with 5 deletions of the open reading frame designed to result in translation from different in-frame start codons (ATG codon sequences). The rtPDE3A deletion constructs and the locations of the different ATG start codons in the PDE3A1 ORF (SEQ ID NO:14) are illustrated in FIG. 12. All recombinant isoforms migrated with apparent molecular weights approximately 20,000 higher than predicted by their amino acid sequences (SEQ ID NO:1, SEQ ID NO:2, SEQ ID NO:3).

TABLE 4

Functional domains in cardiac and vascular PDE3 isoforms

|  | NHR1 | PK-B site ("P1") | PK-A site upstream ("P2") | NHR2 | PK-A site, downstream ("P3") | CCR |
|---|---|---|---|---|---|---|
| PDE3B-137 | + | + | + | + | + | + |
| PDE3A-136 | + | + | + | + | + | + |
| PDE3A-118 |  |  | + | + | + | + |
| PDE3A-94 |  |  |  |  |  | + |

The apparent molecular weight of PDE3A-136 was slightly higher than the apparent molecular weight of 131,000 for the recombinant protein as translated from ATG-2 in the PDE3A1 open reading frame (SEQ ID NO:14), indicating that PDE3A1-136 contains part of the NHR1 site (a finding consistent with its recovery only in microsomal fractions), all of NHR2, and the P1, P2 and P3 sites for phosphorylation and activation by PK-B and PK-A. PDE3A-136 is, therefore, generated in cardiac myocytes from PDE3A1, either by translation from ATG1 followed by targeted N-terminal proteolysis or by some post-translational modification that reduces its electrophoretic mobility, resulting in a higher apparent molecular weight.

The apparent molecular weight of PDE3A-118 was indistinguishable from that of the recombinant PDE3A translated from ATG4, indicating that PDE3A-118 lacks NHR1 and the PK-B activation site, but includes the NHR2 and PK-A sites. PDE3A-118 is generated in cardiac and vascular myocytes from PDE3A2 mRNA (SEQ ID NO:15) by translation from ATG4, the third ATG in the open reading frame predicted by the cloned cDNA (GenBank Accession No. NM000921), or by translation from ATG2 or ATG3 followed by targeted N-terminal proteolysis.

The apparent molecular weight of PDE3A-94 was approximately equal to the apparent molecular weight of 94,000 for the recombinant PDE3A translated from ATG7/8, indicating that PDE3A-94 contains neither the membrane-association domains NHR1 and NHR2, nor any of the three phosphorylation sites. PDE3A-94 is generated in cardiac and vascular myocytes from PDE3A2 mRNA (SEQ ID NO:15), either by translation from AUG7/8 or by translation from a more upstream ATG followed by proteolytic removal of a more extensive length of N-terminal sequence. That PDE3A-118 and PDE3A-94 are generated from a single mRNA (SEQ ID NO:15) by alternative translational processing in vivo is consistent with the observation that a PDE3A-94-like protein is generated from longer constructs by translation from downstream ATG sequences in vitro.

The N-terminus predicted from the PDE3A1 open reading frame (SEQ ID NO:14) was absent from native PDE3A-136, the longest PDE isoform identified. All three isoforms contain the same C-terminal amino acid sequences, downstream of different N-terminal starting points.

PDE3A-136 and PDE3B-137, which contain the transmembrane helices of NHR1, would be expected to be exclusively membrane-bound in cardiac and vascular myocytes. PDE3A-118, which contains NHR2 but not NHR1, and PDE3A-94, which lacks both NHR1 and NHR2, would be expected to associate reversibly with intracellular membrane proteins or to be partitioned between the cytosolic and microsomal compartments. Their presence in both microsomal and cytosolic fractions is compatible with this conclusion. Further, the fact that PDE3A-I18 and PDE3A-94 can be recovered in microsomal fractions suggests that interactions with anchoring or targeting proteins are involved in their intracellular localization.

The N-terminal sequence differences may cause different PDE3 isoforms to interact with different anchoring or targeting proteins that localize them to different signaling modules. As a consequence, each PDE3 isoform may regulate the phosphorylation of different substrates of PK-A and PK-G.

Surprisingly, transcription/translation from every PDE3A-derived construct generated a recombinant PDE3A isoform whose apparent molecular weight corresponded to that of PDE3A-94. Determination whether the latter might be generated by translation from a downstream AUG in the full-length PDE3A mRNA (SEQ ID NO:14, SEQ ID NO:18) was performed by expression of a mutated construct starting from ATG1 in the PDE3A1 mRNA (SEQ ID NO:14) in which ATG7/8 was mutated to CTGCTG (Met-Met Leu-Leu). Expression of the mutated construct resulted in the disappearance of the 94,000 molecular weight recombinant PDE3A, a result consistent with the generation of PDE3A-94 from the full-length PDE3 mRNA by translation from AUG7/8.

Example 6

5 RACE PCR

Studies have shown that a PDE3A2 mRNA (SEQ ID NO:15), whose sequence is identical to that of the PDE3A1 cDNA downstream of roughly nucleotide 300 in the latter's open reading frame (SEQ ID NO:14) but which lacks PDE3A1's upstream sequence (SEQ ID NO:14, SEQ ID NO:18), is present in both cardiac and vascular myocytes, while PDE3A1 mRNA (SEQ ID NO:14, SEQ ID NO:18) is present in cardiac but not in vascular myocytes (Y. H. Choi et al., Biochem J., 2001). To determine if the PDE3A2 mRNA (SEQ ID NO:15) contained an alternative sequence upstream of roughly nucleotide 300, 5 RACE PCR was performed on a human myocardial cDNA library using three pairs of antisense primers derived from the shared sequences of PDE3A1 (SEQ ID NO:14) and PDE3A2 (SEQ ID NO:15).

Subcloning and sequencing of the multiple 5 RACE products indicated that the PDE3A2 mRNA (SEQ ID NO:15) contained no alternative sequence upstream of roughly nucleotide 300 (not shown). Similar results were obtained when 5 RACE was performed with comparable primers on a human aortic cDNA library (not shown).

Example 7

Southern and Northern Blotting

Northern and Southern blotting was performed on nucleic acids from human left ventricular myocardium using probes derived from different regions of the PDE3A1 open reading frame (see SEQ ID NO:14). The first nucleic acid probe, derived from nucleotides (−)268-189, corresponded to a region predicted to be present in PDE3A1 (SEQ ID NO:14), but not in PDE3A2 (SEQ ID NO:15). The other two nucleic acid probes used corresponded, respectively, to nucleotides 517-957 and 2248-2610 of PDE3A1 (SEQ ID NO:14), regions predicted to be present in both PDE3A1 (SEQ ID NO:14) and PDE3A2 (SEQ ID NO:15).

All three of the nucleic acid probes bound to an 8.2 kilobase band (not shown). The two downstream probes also bound to a 6.9 kilobase band to which the upstream probe did not bind (not shown). These results indicate that the 8.2 kilobase band is PDE3A1 (SEQ ID NO:14, SEQ ID NO:18) and the 6.9 kilobase band is PDE3A2 (SEQ ID NO:15). The size differences observed between the two hybridized bands are accounted for by the absence of the first roughly 300 nucleotides of the open reading frame of PDE3A1 (SEQ ID NO:14) from PDE3A2 (SEQ ID NO:15), consistent with the generation of the latter by alternative transcription or splicing within exon 1 of the open reading frame of PDE3A1 (SEQ ID NO:14). This result is consistent with a result predicted by ribonuclease protection assays of RNA prepared from human myocardium and cultured human aortic myocytes with antisense probes spanning nucleotides 208-537 and nucleotides 2248-2610 of PDE3A1 (SEQ ID NO:14) (Y. H. Choi et al., *Biochem J.*, 2001). Importantly, PDE3A1 mRNA (SEQ ID NO:14, SEQ ID NO:18) and PDE3A-136 were determined to be present in only cardiac myocytes while PDE3A2 mRNA (SEQ ID NO:15), PDE3A-118, and PDE3A-94 were present in both cardiac and vascular myocytes. This result indicates that PDE3A1 mRNA (SEQ ID NO:14, SEQ ID NO:18) gives rise to PDE3A-136 and PDE3A2 mRNA (SEQ ID NO:15) gives rise to both PDE3A-118 and PDE3A-94.

Example 8

Figure 8:
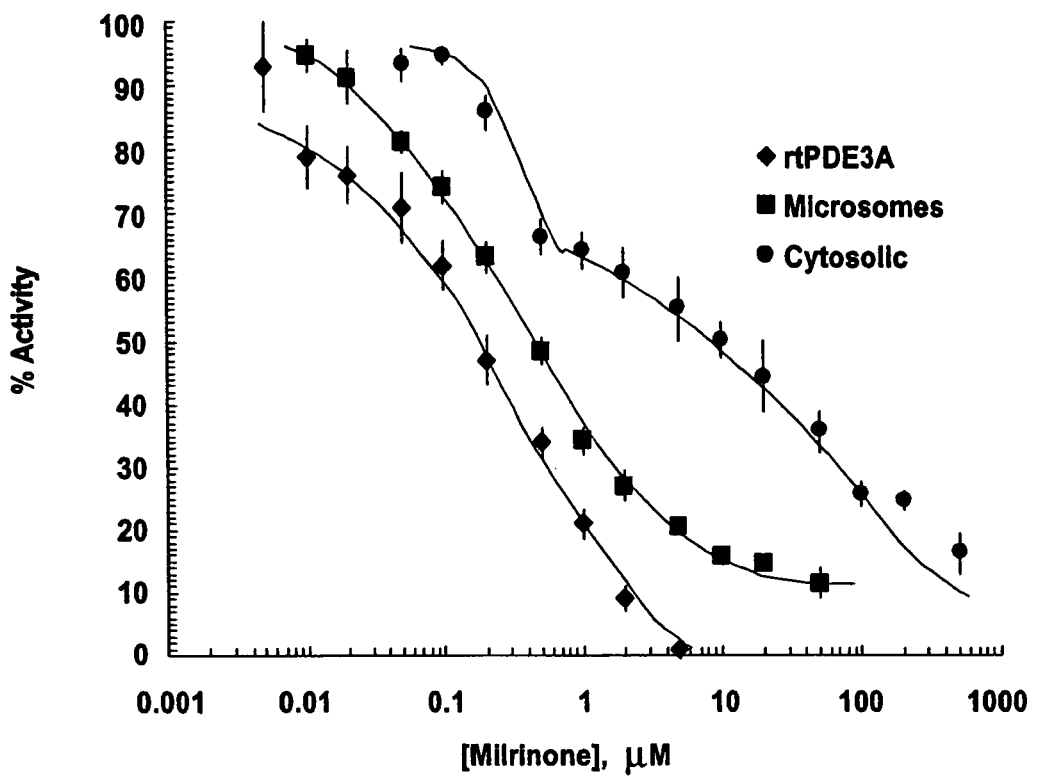
FIG. 8: Inhibition of cAMP hydrolytic activity of rtPDE3A1 (in Sf9 lysates) and cytosolic and microsomal fractions of human myocardium by milrinone.

Inhibitors of PDE3 Activity and Effects of Intracellular Localization on Catalytic Activity The effects of two PDE3 inhibitors, cilostazol (not shown) and milrinone (FIG. 8), on cAMP hydrolytic activity in cytosolic and microsomal fractions of human myocardium were examined. These drugs had more potent effects in microsomal fractions (FIG. 8).

The PDE3 inhibitor milrinone was used to quantify PDE3 cAMP- and cGMP-hydrolytic activity in lysates of Sf9 cells expressing recombinant PDE3A isoforms and in cytosolic and salt-washed microsomal fractions of human myocardium (Table 5). Catalytic activity was measured at 0.1 µM cAMP and cGMP. Milrinone-sensitive activity for tissue fractions was calculated by measuring cyclic nucleotide hydrolysis inhibited by milrinone at concentrations equal to its $IC_{50}$ values for cAMP and cGMP hydrolysis by recombinant PDE3A1, and dividing by 0.5.

TABLE 5

Milrinone-sensitive cAMP and cGMP hydrolytic activity in subcellular fractions of human myocardium

| Preparation | milrinone-sensitive cAMP hydrolytic activity, pmol/mg/min | milrinone-sensitive cGMP hydrolytic activity, pmol/mg/min | ratio milrinone-sensitive cAMP/cGMP hydrolytic activity |
|---|---|---|---|
| rtPDE3A1 (full ORF) | 1754 | 405 | 4.3 |
| cytosolic fraction, human myocardium | 169 | 75 | 2.3 |
| salt-washed microsomes, human myocardium | 64 | 10 | 6.4 |
| rtPDE3AΔ5 (aa 623-1141) | 1408 | 346 | 4.1 |

The ratio of milrinone-sensitive cAMP/cGMP hydrolytic activity in cytosolic fractions was lower than that observed with full-length recombinant PDE3A, while the ratio in microsomal fractions was higher. To determine if these differences were the result of N-terminal deletions, the same studies were performed on lysates of Sf9 cells expressing a recombinant PDE3A from which the N-terminus had been deleted (rtPDE3AΔ5). N-terminal truncation did not affect the cAMP/cGMP activity ratio.

The higher ratio of milrinone-sensitive cAMP/cGMP hydrolytic activity in the microsomal fraction relative to that seen in recombinant PDE3 isoforms suggests that localization to intracellular membranes increases the selectivity of PDE3 isoforms for cAMP, possibly resulting from the interaction of membrane-bound PDE3 with other proteins.

The contribution of PDE3 isoforms to compartmental regulation of cyclic nucleotide hydrolysis was examined in subcellular preparations from native human myocardium and cultured pulmonary artery myocytes. The results are presented in Table 6.

PDE3 comprises the majority of the total cAMP hydrolytic activity in microsomal fractions of human myocardium at both low and high cAMP concentrations. It comprises a smaller but significant fraction of cAMP hydrolytic activity in cytosolic fractions of these cells, probably reflecting the larger presence of other cAMP phosphodiesterases in the cytosol. In cultured pulmonary artery myocytes, these findings are reversed. PDE3 contributes less to membrane-bound cAMP hydrolytic activity but more to cytosolic cAMP hydrolytic activity.

PDE3 comprises a large portion of the total cGMP hydrolytic activity in microsomal fractions of human myocardium at low but not at high cGMP concentrations. This likely reflects the presence of other lower affinity cGMP phosphodiesterases in these fractions.

TABLE 6

Milrinone-sensitive cAMP and cGMP hydrolytic activities in subcellular fractions of human myocardium and cultured human pulmonary artery myocytes
% of total cAMP and cGMP hydrolytic activities in the identified fractions

| | 0.1 µM cAMP | 1.0 µM cAMP | 0.1 µM cGMP | 1.0 µM cGMP |
|---|---|---|---|---|
| Myocardium, cytosol | 52% | 54% | 10% | 9% |
| Myocardium, microsomes | 67% | 73% | 42% | 13% |
| Pulmonary artery, cytosol | 40% | 31% | 19% | 4% |
| Pulmonary artery, microsomes | 24% | 39% | 14% | 9% |

PDE3 contributes relatively little to cGMP hydrolytic activity in cytosolic fractions of human myocardium. PDE3 comprises a surprisingly small portion of the total cGMP hydrolytic activity in both microsomal and cytosolic fractions of pulmonary artery myocytes at both low and high concentrations of substrate. The fact that PDE3s contribute less to total cGMP hydrolytic activity than to total cAMP hydrolytic activity in subcellular fractions of these cells, taken in the context of the fact that competitive PDE3 inhibitors inhibit cAMP hydrolytic activity more potently than they inhibit cGMP hydrolytic activity of PDE3 (see Table 7), suggest that the clinical effects of currently available competitive PDE3 inhibitors are likely to be mediated to a greater degree by increases in cAMP content than by increases in cGMP content in both cardiac and vascular myocytes. This conclusion cannot be extrapolated to agents that may inhibit PDE3 activity through non-competitive mechanisms proposed herein. The latter may change the profile of cellular actions of PDE3 inhibition, representing an additional possible benefit to the approaches proposed over currently available therapies.

TABLE 7

$IC_{50}$s for inhibition of rtPDE3A by milrinone

| Substrate concentration | 0.1 μM cAMP | 1.0 μM cAMP | 0.1 μM cGMP | 1.0 μM cGMP |
|---|---|---|---|---|
| $IC_{50}$ | 0.9 μM | 6.0 μM | 2.4 μM | 23 μM |

Example 9

Phosphorylation Sites and Effects of Phosphorylation on PDE3A Isoforms

The phosphorylation sites on PDE3A-136 were localized by labeling studies to amino acid residues 288-294 (P1 site), 309-312 (P2 site) and 435-438 (P3 site). The P2 and P3 sites on PDE3A-136 only contain one serine residue each and the phosphorylated residue is unambiguous (FIG. 11). The P1 site contains multiple serine residues and it is not certain at present which is phosphorylated.

Differences with respect to the presence of PK-A and PK-B sites in the different isoforms of PDE3 indicate differences in regulation by phosphorylation. PDE3A-136 and PDE3B-137 contain sites P1, P2 and P3 and are thus potentially subject to regulation by both PK-A and PK-B (Table 4). PDE3A-118 contains only P2 and P3 and can thus be regulated only by PK-A (Table 4). PDE3A-94 contains none of these phosphorylation sites, therefore, its activity can be regulated by neither PK-A nor PK-B. These N-terminal sequence differences may lead to differences in regulation by other interacting partners.

The effects of phosphorylation at the P3 site of PDE3A, along with the apparently equivalent site on PDE3B-137, on phosphodiesterase catalytic activity are shown in Table 8. Flag-tagged rtPDE3B-137 isoforms (full ORFs) were prepared with mutations at P3, one of the two PK-A sites (FIG. 4). These included a constitutively nonphosphorylated form, in which Ser421 was mutated to alanine ("S421A") and a form that acted as if it were constitutively phosphorylated, in which Ser421 was mutated to aspartic acid ("S421D"). The charged group on the end of the aspartate side chain resembles a phosphate group in its effect on phosphodiesterase activity. These recombinant isoforms were used, together with the corresponding wild-type rtPDE3B, to examine the effects of phosphorylation at site P3 on catalytic activity and inhibitor sensitivity. Catalytic activity of PDE3 was measured in detergent-solubilized lysates of Sf21 cells expressing Flag-tagged rtPDE3 isoforms (full-length ORFs). Values for $V_{max}$ and $K_m$ were calculated by nonlinear regression (first-order kinetics). Preparations were diluted so that each contained equal concentrations of immunoreactive PDE3 as determined by quantitative Western blotting with anti-Flag antibodies. The three isoforms of rtPDE3B were observed to have comparable catalytic activity toward cAMP and cGMP (Table 8). The three isoforms also exhibited similar sensitivity to inhibition by cilostazol (data not shown). This suggests that phosphorylation at P3 has little, if any, direct effect on enzyme activity.

TABLE 8

Effect of $ser^{421}$ mutations on catalytic activity of PDE3B

| rtPDE3B isoform | cAMP hydrolysis | | cGMP hydrolysis | |
|---|---|---|---|---|
| | $V_{max}$ pmol/min/ml | $K_m$ μM | $V_{max}$ pmol/min/ml | $K_m$ μM |
| wild type | 977 ± 53 | 0.15 ± 0.03 | 325 ± 18 | 0.09 ± 0.02 |
| S421A | 968 ± 144 | 0.21 ± 0.09 | 300 ± 16 | 0.07 ± 0.02 |
| S421D | 809 ± 12 | 0.17 ± 0.01 | 241 ± 42 | 0.07 ± 0.04 |

Figure 9:
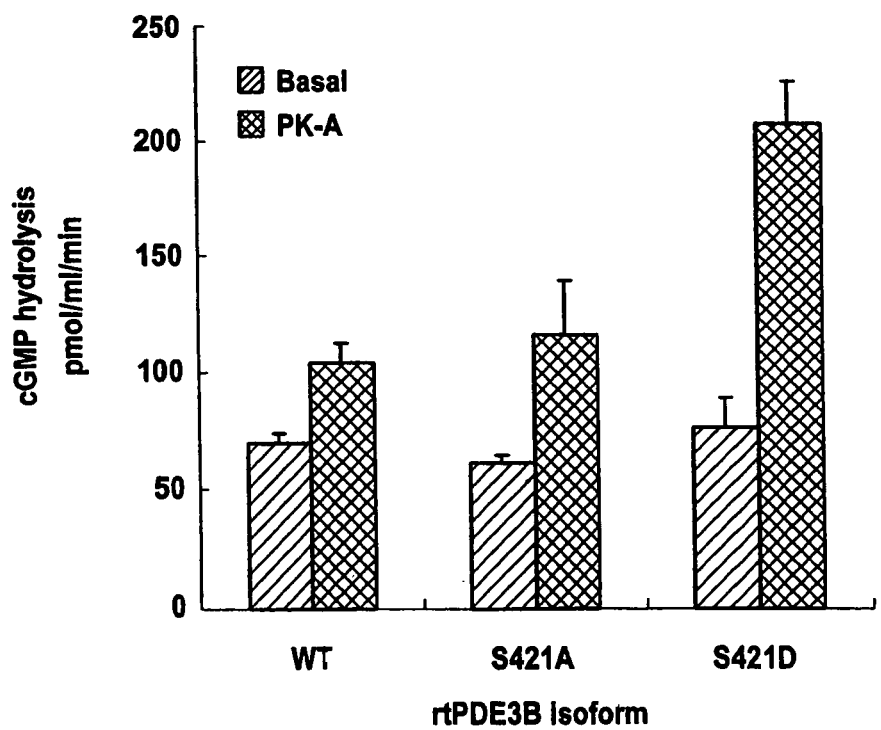
FIG. 9: Stimulation of cGMP hydrolytic activity by PK-A. Detergent-solubilized lysates of Sf21 cells expressing rtPDE3B isoforms (full-length ORFs, including wild-type, Ser→Ala and Ser→Asp, mutations) were prepared, and cGMP hydrolytic activity was determined at 0.03 µM cGMP after incubation in the presence or absence of PK-A and ATP. Values represent mean±standard deviation (each pair of values represents data from a single preparation).

The rtPDE3Bs were used to study the effects of phosphorylation by PK-A at other sites. Phosphorylation of these isoforms with PK-A caused a much greater stimulation of activity in S421D than in S421A or the wild-type rtPDE3B (FIG. 9). These results indicate an interaction between P3 and P2, the upstream PK-A site. Phosphorylation of P3 may increase the stimulation of activity by PK-A by facilitating phosphorylation at P2. The fact that stimulation of the wild-type rtPDE3B has less effect than a Ser→Asp mutation at P3 may reflect incomplete phosphorylation of the latter site. Alternatively, phosphorylation of P3 may potentiate the effect of phosphorylation of P2 on enzyme activity. Another possibility is that phosphorylation of P3 has an inhibitory effect on catalytic activity that is overcome by phosphorylation of P2.

Example 10

Site-Specific Mutations and Phosphorylation

The phosphorylation of PDE3B-137, PDE3A-136 and PDE3A-118 by PK-A and PK-B is examined using recombinant constructs with thrombin cleavage sites followed by $his_6$ tags at the C-terminus. Constructs are expressed in Sf9 cells by infection with baculovirus vector. $His_6$-tagged recombinant proteins are purified by $Co^{2+}$-affinity chromatography (Clontech resin) and their $his_6$ tags are removed by thrombin cleavage.

rtPDE3s are phosphorylated by PK-A (Sigma) and PK-B (Upstate Biotechnology). Varying concentrations of purified rtPDE3s are incubated in the presence of nanomolar concentrations of kinase, saturating concentrations of $[\gamma-^{32}P]ATP$ and phosphatase inhibitors. Reaction mixtures are subjected to SDS-PAGE, and $^{32}P$ incorporation is quantified in excised PDE3 bands following established protocols (Movsesian et al., 1984). Values for $K_m$ and $V_{max}$ for phosphorylation by PK-A and PK-B are calculated by nonlinear regression and standardized using peptide substrates as controls (Kemptide for PK-A, Crosstide for PK-B).

The use of rtPDE3s with Ser→Ala and Ser→Asp mutations at selected phosphorylation sites allows the isolation of individual sites (by rendering others nonphosphorylatable). Interactions between sites may also be examined. For example, to study the effect of phosphorylation at P2 by PK-A on phosphorylation at P1 by PK-B, rtPDE3s are prepared with Ser→Ala and Ser→Asp mutations at P2 and P3. The effects on $K_m$ and $V_{max}$ for phosphorylation by PK-B at P1 are examined.

Non-physiologic artifacts may be induced using Ser→Asp mutations. For example, they may mimic phosphorylation at a site that is not phosphorylated in vivo in the cell of interest. To address this problem, the phosphorylation of specific sites in aortic myocytes and HL-1 cells transfected with tagged rtPDE3s is examined. To examine phosphorylation at P1, HL-1 cells are transfected with PDE3 constructs with Ser→Ala and Ser→Asp mutations at P2 and P3, using HL-1 cells transfected with Ser→Ala mutations at P1 as a negative control. Cells are preincubated with $^{32}PO_4^{3-}$ and exposed to $\beta_1$- and $\beta_2$-adrenergic receptor agonists, forskolin, PGE2 and IBMX (to activate PK-A) and/or IGF-1±wortmannin (to activate PI3-K, which phosphorylates and activates PK-B). PDE3 is immunoprecipitated from the resulting cellular fractions with anti-Tag antibodies and subjected to SDS-PAGE and autoradiography to determine whether phosphorylation at P1 has occurred and is influenced by phosphorylation at other sites. Quantitative Western blotting is then performed to normalize $^{32}P$ incorporation to immunoreactive PDE3. This approach may be used to determine whether phosphorylation of one site affects phosphorylation of another in vivo (cultured cells). This approach has been validated in adipocytes where the sites phosphorylated in transfected proteins have been determined to be the same as those phosphorylated in native proteins (Kitamura, et al., 1999).

Two similar approaches may be performed to validate phosphorylation in cultured myocytes. First, antibodies are raised to synthetic peptides corresponding to phosphorylated P1, P2 and P3 domains. The studies described above are repeated in non-transfected cells (without radiolabeling). SDS-PAGE is performed on cell homogenates and the phosphor-specific antibodies are used to confirm or refute phosphorylation at individual sites by Western blotting. The same studies may be performed after preincubation with $^{32}PO_4^{3-}$. Native PDE3s are immunoprecipitated from cellular homogenates with anti-CT antibodies. SDS-PAGE is performed on these native proteins and the PDE bands are excised. The protein is extracted from the gel material and limited proteolysis with trypsin, chymotrypsin, CNBr and/or V8 is performed. The resulting peptide fragments are resolved via two-dimensional mapping, using two-dimensional peptide maps of mutagenized rtPDE3s phosphorylated in vitro as controls. Comparison thereof reveals which sites are phosphorylated in the HL-1 cells.

Example 11

Effects of Phosphorylation on Intracellular Localization

The role of the N-terminus in intracellular targeting was elucidated through an approach that involved the transfection of cultured cells with rtPDE3 constructs. This approach may be expanded by stably transfecting cultured aortic myocytes (Clonetics) with $his_6$- or Flag-tagged PDE3B-137- and PDE3A-118-derived constructs with Ser→Ala and Ser→Asp mutations at the three phosphorylation sites identified herein. PDE3A-94 is not included because it does not appear to contain any of the phosphorylation sites.

The protocol for stable transfection uses the vector pcDNA 3.1 (Invitrogen). This vector is driven by a CMV promoter, includes a neomycin resistance element for selection and adds a C-terminal myc-$his_6$ tag to the expressed protein. The choice of stable rather than transient transfection is based on the higher levels of recombinant protein expression observed in stable transformants (not shown). The intracellular localization of rtPDE3 isoforms is determined by indirect immunofluorescence using fluorophore-tagged anti-$his_6$ or anti-Flag antibodies. Co-localization relies on the use of antibodies to markers for different intracellular membranes. Phosphorylation does not induce translocation of PDE3B-137, as it contains the transmembrane helices of NHR1 and is, therefore, likely to be an intrinsic membrane protein. However, some combinations of Ser→Asp mutations induce a translocation of PDE3A-118 from intracellular membranes to the cytosol.

The results of these studies may not be applicable to cardiac myocytes, since the PDE3 isoforms are not identical and the intracellular targeting mechanisms may differ. For this reason, the studies described above may be repeated in cardiac myocytes or cells derived from cardiac myocytes using PDE3A-136 instead of PDE3B-137.

Example 12

Indirect Immunofluorescence and Intracellular Localization

The effects of phosphorylation of the sites P1, P2 and P3 on the membrane targeting domains NHR1 and NTIR2 and intracellular localization were studied. The role of the N-terminus of PDE3 in intracellular targeting was elucidated by transfecting cultured cells with rtPDE3 constructs and visualizing the intracellular localization of these rtPDE3 constructs by indirect immunofluorescence. COS-7 cells were transfected with PDE3A and PDE3B constructs with C-terminal Flag-tags and varying N-terminal deletions, and localization was visualized using fluorescein-labeled anti-Flag antibodies. Constructs containing NHR1 were found to be membrane-bound (not shown). Constructs lacking NHR1 but containing NHR2 were partially membrane-bound and partially cytosolic and constructs lacking both NHR1 and NHR2 were exclusively cytosolic (not shown). This distribution corresponds to the distribution of native PDE3s in human myocardium and aortic myocytes.

To extend this approach, cultured aortic myocytes (Clonetics, East Rutherford, N.J.) may be transfected with Flag-tagged PDE3B-137- and PDE3A-118-derived constructs with Ser→and Ser→Asp mutations at the P1, P2 and P3 PK-A and PK-B phosphorylation sites. Stable transfection utilizes the transcription vector pcDNA 3.1 (Invitrogen, Carlsbad, Calif.). The pcDNA vector is driven by a CMV promoter, includes a neomycin resistance element for selection, and adds a C-terminal Flag tag to the expressed protein. The intracellular localization of rtPDE3 isoforms with mutagenized phosphorylation sites may be determined by indirect immunofluorescence using fluorophore-tagged anti-Flag antibodies. Co-localization relies on the use of commercially available antibodies to markers for different intracellular membranes.

Results in vascular myocytes may not be applicable to cardiac myocytes. The PDE3 isoforms in the two cell types are not identical, and the intracellular targeting mechanisms may be different. For this reason, the above studies may be repeated in HL-1 cells, an immortalized cell line derived from atrial myocytes (Claycomb, et al., 1998). Western blotting indicates that the representation of PDE3 isoforms in subcellular fractions prepared from these cells is similar to that seen in preparations from human left ventricular myocardium, making these cells particularly suitable for these experiments. Transfections of HL-1 cells is performed with PDE3A-136- rather than PDE3B-derived constructs to reflect the different patterns of cellular expression. This transfection may be transient or stable. A high percentage of transfection efficiency with PDE3 constructs using transient transfection obviates the need for stable transfection of rtPDE3 isoforms.

Example 13

Protein-Protein Interactions

The interactions of PK-B with PDE3B were examined. Microsomal fractions of 3T3 adipocytes (which express PDE3B) were solubilized with NP-40 and fractionated by gel filtration. Western blotting showed the presence of separate peaks for PDE3B and PK-B, but some of the PK-B was found in the PDE3B peak (not shown). An association between PK-B and PDE3B was confirmed by the ability of anti-PDE3B antibodies to co-immunoprecipitate the two proteins in the PDE3B peak (not shown). Treatment with insulin increased the phosphorylation of PK-B and appeared to increase the percentage of PK-B co-purifying with PDE3B (not shown). These results suggest that PK-B and PDE3B form stable complexes in vivo, either by direct interaction or by co-interaction with another protein.

Figure 10:
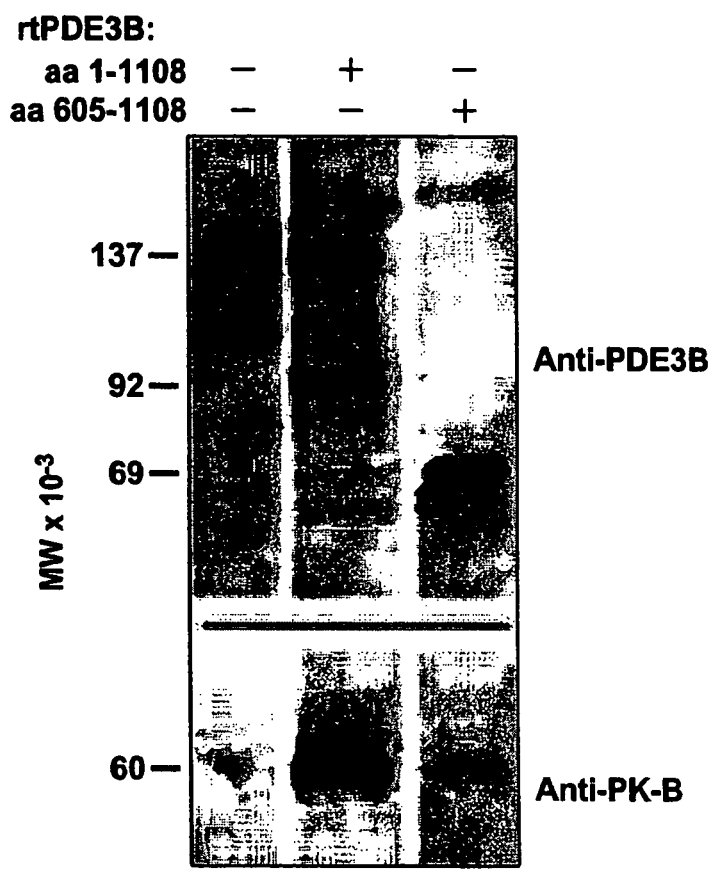
FIG. 10: Co-immunoprecipitation of rtPK-B and rtPDE3B. Amino acid sequences of rtPDE3B are shown at top. Detergent-solubilized lysates of Sf9 cells infected with rtPDE3B were mixed with lysates from Sf9 cells infected with rtPK-B. Proteins were immunoprecipitated with anti-PDE3B antibodies and subjected to Western blotting with anti-PDE3B and anti-PK-B antibodies. PK-B co-precipitates with the full-length but not the truncated rtPDE3B. The identity of the 92 kDa band is unknown.

Detergent-solubilized lysates of Sf9 cells expressing rtPK-B were mixed with detergent-solubilized lysates of Sf9 cells expressing one of two Flag-tagged forms of PDE3B. The first isoform of PDE3B contained its full ORF. The second lacked the N-terminal 604 amino acids containing the NHR1, NHR2 and the three phosphorylation sites. PK-B could be co-immunoprecipitated with anti-Flag antibodies in the presence of the full-length rtPDE3B but not in the presence of the N-terminal-deleted form (FIG. 10), confirming the role of the N-terminus of PDE3B in its association with PK-B.

The addition of Flag-tagged rtPDE3B to 3T3 lysates allowed the co-immunoprecipitation of AKAP220, which co-localizes PK-A and PP1 (Schillace et al., 2001). This indicates that interactions with other proteins serves to localize PDE3 to specific signaling modules, and suggests that blocking these interactions will alter the function of PDE3.

Example 14

Identification of PDE3 Kinases, Phosphatases and Binding Peptides/Interacting Partners Purified rtPDE3s may be used as affinity ligands to identify PDE3-binding proteins ("PDE3-BPs") by interaction cloning from phage-displayed myocardial and vascular smooth muscle cDNA libraries. This approach involves two basic steps: preparation of phage-displayed cDNA libraries and biopanning with rtPDE3.

Preparation of Phage-Displayed cDNA Libraries cDNA inserts from commercially available human cardiac (XbaI-(dT)$_{15}$-primed) and aortic (oligo(dT) and random-primed) libraries (Clontech, Palo Alto, Calif.) are PCR-amplified using vector-derived primers (λTriplEx for cardiac, λgt10 for aortic) with unique restriction sites. These libraries have been used to clone PDE3 isoforms, which are expressed in relatively low abundance. PCR products are size-fractionated on agarose gels. Products greater than 500 nucleotides in length are purified by agarose gel electrophoresis and ligated into the genes of phage coat proteins using unique restriction sites. Proteins or protein fragments encoded by the cDNA inserts are displayed on the phage surface.

Two phages with different reproductive biologies are used. One is M13, a non-lytic phage that is secreted after assembly in the bacterial periplasm. cDNA inserts up to 1000 amino acids in length can be expressed as C-terminal fusions to the pVI coat protein of M13. The protocols used are as disclosed in Fransen et al. (1999). The same vectors and protocols are used to insert human cardiac and aortic cDNA libraries into pVI. The second phage is T7 (Novagen, Madison, Wis.). This phage, being lytic, is processed quite differently from M13, so that cDNA inserts that may interfere with M13 function are not likely to affect T7 (and vice versa). T7 is capable of displaying cDNA products up to 1200 amino acids in length. Methods for its use have been disclosed in Zozulya et al. (1999).

Biopanning with rtPDE3

Phages with cDNA inserts are incubated with rtPDE3s that are immobilized either directly onto polystyrene wells or indirectly by binding of C-terminal his$_6$ tags to anti-his$_6$ mAb, followed by immunoprecipitation. Phage whose cDNA inserts encode full-length or truncated PDE3-BPs are co-immobilized with PDE3, then eluted and amplified in E. coli. Each round of this procedure yields a phage library enriched in cDNAs encoding PDE3-binding proteins. Biopanning is repeated through several iterations until the titer of phage binding to immobilized PDE3 is ten-fold above background (phage binding to wells in the absence of PDE3), at which point, individual phage colonies are cloned and their cDNA inserts sequenced.

Phages are biopanned with rtPDE3s. rtPDE3A-118 and rtPDE3A-94 are used for both cardiac and aortic libraries. PDE3B-137 and PDE3A-136 are used exclusively for aortic and cardiac libraries, respectively. Thiophosphorylated rtPDE3 are prepared with PK-A and/or PK-B and ATPγS for use as bait in parallel experiments to select proteins that bind preferentially to phosphorylated PDE3s, for example, phosphatases. Phosphothioesters are resistant to dephosphorylation and thiophosphorylated proteins, therefore, bind stably to protein phosphatases.

Cloned cDNA sequences identified by biopanning may be used to search protein databases and identify full-length binding proteins for PDE3.

The skilled artisan will realize that the methods discussed above could be used to identify novel isoform-selective inhibitors or activators of PDE3. Purified isoform proteins are used as ligands for biopanning general phage display libraries comprising random nucleic acid sequences encoding short peptides. Phages that bind with relatively high affinity to one or more PDE3 isoforms are selected and their DNA inserts are sequenced. The encoded peptides are chemically synthesized and their ability to activate or inhibit PDE3 catalytic activity or to block or mimic the effect of phosphorylation at P1, P2 or P3 on catalytic activity is examined using standard enzyme analysis. The effect of identified activators or inhibitors on each PDE3 isoform is determined and isoform-selective compounds are identified. Use of site-specific mutagenized isoforms that are designed to be constitutively unphosphorylatable or to mimic constitutively phosphorylated residues at P1, P2 and P3 identifies activators or inhibitors that are selective for phosphorylated or dephosphorylated variants of each isoform.

Example 15

Characterization of Binding Interactions and Effects on PDE3 Function

Confirmation of Binding of Cloned Prospective PDE3-BPs to PDE3

Binding interactions are confirmed by co-immunoprecipitation, which can occur in any of four ways. First, native PDE is immunoprecipitated from lysates of cardiac and aortic myocytes using anti-PDE antibodies and co-immunoprecipitation is confirmed via Western blotting using antibodies raised to the cloned PDE-BP. The second method reverses the order of the antibodies used. Thus, antibodies to the cloned PDE3-BP are used for immunoprecipitation and co-immunoprecipitation is confirmed via Western blotting using anti-PDE3 antibodies. Third, aortic myocytes or HL-1 cells are transfected with Flag-tagged rtPDE3-BPs, followed by co-immunoprecipitation and Western blotting with anti-Flag antibodies. Lastly, tagged rtPDE3s and rtPDE3-BPs are expressed by in vitro transcription/translation in reticulocyte lysates or in a baculovirus/Sf9 system. The recombinant proteins are co-incubated and co-immunoprecipitation is tested for AKAP-220, a method described elsewhere in this document.

Characterization of Binding Interactions and Effects on PDE3 Function

The affinity ($K_D$) of the interaction between PDE3 and various binding proteins or peptides may be determined by ELISA, using immobilized rtPDE3 and rtPDE3-BPs (obtained by expression in E. coli or Sf9/St21 cells). The effects of rtPDE3-BPs on the catalytic activity and inhibitor sensitivity of rtPDE3s is determined as described above. The effects of PDE3-BPs on the phosphorylation of rtPDE3s by PK-A and PK-B in vitro is determined as described above. rtPDE3s with Ser→Ala and Ser→Asp mutations are used to determine how phosphorylation at specific sites affects interactions with PDE3-BPs.

Interacting domains of PDE3s and their binding partners are identified by deletional and site-directed mutagenesis of PDE3 and/or PDE3-BPs. Peptides derived from interacting domains are examined for inhibition of PDE3/PDE3-BP interactions. Inhibition of PDE3/PDE3-BP interactions is examined by ELISA or by measuring inhibition of functional correlates of binding. For example, if binding to a PDE3-BP increases the $K_m$ of PDE3 for cAMP, the ability of peptides to prevent this increase is determined. Alternatively, peptides that mimic the effects of PDE3-BPs may be PDE3 activators. Peptides in either category are of interest as potential therapeutic agents and may serve as templates for peptidomimetic drugs or reporters for high-throughput screening.

Peptides derived from the phase display experiments derived above are also tested for their ability to either block the binding of PDE3 to PDE3-BPs or to mimic the effect of PDE3-BPs on catalytic activity or inhibitor sensitivity of PDE3.

To quantify the affinity of PDE3 to PDE3-BP, surface plasmon resonance (Biacore, Piscataway, N.J.) using purified rtPDE3s and rtPDE3-BPs (obtained by expression in E. coli or Sf9/Sf21 cells) is performed. Generally, surface plasmon resonance (SPR) uses light reflected from a conducting film at the interface between two media of different refractive index. In this instance, the media are the biological sample and the glass of a sensor chip. The conducting film is a thin layer of gold on the sensor chip surface. When the molecules in the biological sample bind to the surface of the sensor chip, the concentration (and, therefore, the refractive index) at the chip surface changes and an SPR response is detected. Here, his-tagged rtPDE3s are captured by anti-his monoclonal antibodies immobilized on flow-cell surfaces of biosensor chips. A series of concentrations of rtPDE3-BPs (expressed in Sf9 cells and purified as described above) are superfused thereon and surface plasmon resonance responses are used to determine values for $K_D$.

Effects of Phosphorylation on Interactions Between PDE3 and PDE3-BP

To determine the effects of phosphorylation at specific sites on interactions between PDE3 and PDE3-BP, surface plasmon resonance experiments are performed as above using rtPDE3s with Ser→Ala and Ser→Asp mutations at the three phosphorylation sites P1, P2 and P3. The effects of these mutations on the $K_D$ of the reaction described above are determined. The kinetics of phosphorylation at P1, P2 and P3 by PK-A and PK-B in the presence and absence of PDE3-BPs are also determined.

The ability of any new PDE3 kinase to phosphorylate P1, P2 and P3 may be examined for PK-A and PK-B, as described above.

The ability of PDE3 phosphatases to dephosphorylate P1, P2 and P3 may also be determined. This entails the use of rtPDE3's with Ser→Ala mutations at all but one of the phosphorylation sites. These rtPDE3s are phosphorylated in the presence of [$\gamma$-$^{32}$P]ATP and the appropriate kinase (e.g., PK-A or PK-B). $^{32}$P release in the presence of phosphatase is characterized in terms of $V_{max}$ and $K_m$. rtPDE3s with Ser→Asp mutations are then used to determine the effect of phosphorylation at one site or dephosphorylation at another.

The effect of PDE3-BP's interactions on catalytic activity, substrate preference, and inhibitor sensitivity is determined by measuring cyclic nucleotide hydrolysis in the absence and presence of PDE3-BPs. Functional K values for PDE3/PDE3-BP's interactions are determined and compared to the $K_D$ values determined by surface plasmon resonance.

Identification of the Interacting Domains of PDE3 and PDE3-BP

Identification of the interacting domains of PDE3s and PDE3-BPs is done via deletional and site-directed mutagenesis of PDE3 and/or PDE3-BP. Several lines of evidence suggest that compartmentally nonselective increases in intracellular cAMP content in cardiac myocytes have both beneficial and harmful effects in dilated cardiomyopathy. Agents capable of selectively activating or inhibiting individual PDE3 isoforms localized to different intracellular compartments or of selectively affecting activity toward cAMP or cGMP may offer major advantages in therapeutic applications. Peptides that block or interfere with the interaction of PDE3 with PDE3-BP may be used to identify functional consequences in vivo. Alternatively, peptides that mimic the effects of PDE3-BPs may be PDE3 activators. Either category of peptides would be useful tools for studying the function of PDE3 isoforms in vivo and may be of interest as prototypical therapeutic agents. They may serve as templates for peptidomimetic drugs or may be tagged for use as reporters for high throughput screening.

Example 16 siRNA Inhibition of PDE3A1

21-nucleotide siRNAs are chemically synthesized using Expedite RNA phosphoramidites and thymidine phosphoramidite chemistries (Proligo, Germany). Synthetic oligonucleotides are deprotected and gel-purifed. The siRNA sequence targeting the PDE3A1 mRNA corresponds to the nucleotide sequences −268 to −241 of the human myocardial PDE3A1 cDNA sequence (SEQ ID NO:18; GenBank Accession No. NM000921). That sequence is located in the 5' untranslated region of the PDE3A1 mRNA (SEQ ID NO:18) and is not present in PDE3A2 (SEQ ID NO:15). It should, therefore, be specific for inhibition of expression of the PDE3A-136 protein.

Sf21 cells expressing rtPDE3A1 are grown at 37° C. in TNM-FH media (BD-Pharmingen, San Diego, Calif.). Transfection with 1.0 nM siRNA is performed with Oligofectamine (Life Technologies) as described by the manufacturer. Cells are incubated 20 hours after transfection and expression of rtPDE3A1 is assayed by Northern blotting. Transfection with siRNA is observed to result in a complete inhibition of rtPDE3A1 expression in Sf21 cells. Control cells are transfected with a random 21 bp siRNA sequence and show no affect on rtPDE3A1 expression.

Example 17

Isoform-Specific Probe and Antisense Construct

In certain embodiments of the invention, isoform-specific probes may be constructed and used, for example, to determine the levels of expression of the PDE3 isoforms in different cells or tissues or in response to various putative inhibitors or activators, such as in a high-throughput screening assay directed towards mRNAs. Because the downstream (3') portions of the PDE3A mRNAs (SEQ ID NO:14, SEQ ID NO:15) are apparently identical, the only region available for isoform-specific probes and/or antisense constructs are at the 5' end of the PDE3A1 mRNA (SEQ ID NO:14, SEQ ID NO:18). An exemplary probe specific for the mRNA encoding the PDE3A-136 isoform protein is disclosed below:
TGATCGTTTCTGCCCGTGCT-TGTTTTCAACTTGAGCGTGCTAGCCTTT AACT-TGAAGAAGTCTCATTGGAGCATCTAG-CATTCTCCAGGAGTTATTCGAAAGCTG AAACTTTCAGTGGATTGTGGGCCTGGG-GAGAAGAAGGATTCCGAGGGTGGAATTGG GAA-GAGCGTGCGTGCGTGTGTGTGTGTGT-GTGTGCGCGCGCGCGTGGGTCGGGG CGGGGGCGTCGGGGGGCCACTGGGAAT-TCAGTGAAGAGGGCACCCTATACCATGGC AGTGC-CCGGCGACGCTGCACGAGTCAGGAA-CAAGCCCGTCCACAGTGGGGTGAGTC AAGCCCCCACGGCGGGCCGGGACTGC-CACCATCGTGCGGACCCCGCATCGCCGCGG GACTCGGGCTGCCGTGGCTGCTGGG-GAGACCTGGTGCTGCAGCCGCTCCGGAGCTCT CGGAAACTTTCCCTG (SEQ ID NO:13)

The probe sequence corresponds to nucleotides −268 to 189 of PDE3A1 (SEQ ID NO:14, SEQ ID NO:18), where nucleotide 1 starts with the first ATG codon in the largest open reading frame (ORF) of the PDE3A1 cDNA sequence (SEQ ID NO:14). The probe sequence (SEQ ID NO:13) is located primarily in exon 1 of the PDE3A1 mRNA, starting in the 5' UTR and ending just before the NHR1 sequence. Primers may be used to generate the probe from the PDE3A1 cDNA or to amplify the target sequence from sample RNA, as disclosed below:
Sense Strand: TGATCGTTTCTGCCCGTGCT-TGTTTTC (SEQ ID NO:16)
Anti-sense: CAGGGAAAGTTTCCGAGAGCTCCG-GAG (SEQ ID NO:17)

The skilled artisan will realize that there are many potential uses for the isoform-specific probe and primers disclosed above. For example, expression of PDE3A1 could be measured in various cells or tissues in either normal individuals or individuals with a disease state, such as cardiomyopathy and/or pulmonary hypertension. The effects of various putative activators or inhibitors on PDE3A1 expression in intact cells could be determined as part of a high-throughput screening assay. Alternatively, an antisense construct, ribozyme and/or siRNA inhibitor could be designed to bind only to PDE3A1 mRNA (SEQ ID NO:14, SEQ ID NO:18). Such an inhibitor would decrease activity of PDE3A-136, while leaving PDE3A-118 and PDE3A-94 activity unaffected. Since SEQ ID NO:13 shows the sequence of part of the PDE3A1 cDNA, the skilled artisan will realize that an antisense construct would be designed to be complementary, preferably exactly complementary, to part or all of the sequence of SEQ ID NO:13. Such a construct could be designed as a double-stranded DNA sequence that is functionally coupled to a promoter and inserted into an expression vector that can be transfected into a target cell. Expression vectors of use in mammalian cells are well known in the art, as summarized above.

All of the compositions, methods and apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and apparatus and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahmad F., L. I. Cong, L. S. Holst, L. M. Wang, T. R. Landstrom, J. H. Pierce, M. J. Quon, E. Degerman, and V. C. Manganiello (2000). Cyclic nucleotide phosphodiesterase 3B is a downstream target of protein kinase B and may be involved in regulation of effects of protein kinase B on thymidine incorporation in FDCP2 cells. *J. Immunology* 164:4678-4688.

Andersen C. B., R. A. Roth, and M. Conti (1998). Protein kinase B/Akt induces resumption of meiosis in *Xenopus* oocytes. *J. Biol. Chem.* 273:18705-18708.

Atienza J. M., D. Susanto, C. Huang, A. S. McCarty, and J. Colicelli (1999). Identification of inhibitor specificity determinants in a mammalian phosphodiesterase. *J. Biol. Chem.* 274:4839-4847.

Barany and Merrifield (1979). *The Peptides*, Gross and Meienhofer, eds., Academic Press, New York, pp. 1-284.

Bass et al. (2001). *Nature* 411:428-429.

Beemon K. and T. Hunter (1978). Characterization of Rous sarcoma virus src gene products synthesized in vitro. *J. Virol.* 28(2):551-66.

Bellus J. (1994). *J. Macromol. Sci. Pure Appl. Chem.* A31(1): 1355-1376.

Berzal-Herranz et al. (1992). *Genes and Devel.* 6:129-134.

Bittner et al. (1987). *Methods in Enzymol.* 153: 516-544.

Bohm M., B. Reiger, R. H. G. Schwinger, and E. Erdmann (1994). cAMP concentrations, cAMP-dependent protein kinase activity, and phospholamban in non-failing and failing myocardium. *Cardiovasc. Res.* 28:1713-1719.

Buxton I. L. and L. L. Brunton (1983). Compartments of cyclic AMP and protein kinase in mammalian cardiomyocytes. *J. Biol. Chem.* 258:10233-10239.

Capaldi et al. (1977). *Biochem. Biophys. Res. Comm.* 76:425.

Cheung P., H. Xu, M. McLaughlin, F. Ghazaleh, G. Livi, and R. Colman (1996). Human platelet cGI-PDE: expression in yeast and localization of the catalytic domain by deletion mutagenesis. *Blood* 88:1321-1329.

Choi Y.-H., D. Ekholm, J. Krall, F. Ahmad, E. Degerman, V. C. Manganiello, M. A. Movsesian (2001). Identification of a novel isoform of the cyclic nucleotide phosphodiesterase PDE3A expressed in vascular smooth muscle myocytes. *Biochem. J.* 353:41-50.

Chowrira et al. (1994). "In vitro and in vivo comparison of hammerhead, hairpin, and hepatitis delta virus self-processing ribozyme cassetyes," *J. Biol. Chem.* 269:25856-25864.

Chowrira et al. (1993). *Biochemistry* 32:1088-1095.

Claycomb W. C., N. A. Lanson Jr, B. S. Stallworth, et al. (1998). HL-1 cells: A cardiac muscle cell line that contracts and retains phenotypic characteristics of the adult cardiomyocyte. *Proc. Natl. Acad. Sci. U.S.A.* 95:2979-2984.

Colberre-Garapin et al. (1981). *J. Mol. Biol.* 150:1.

Colvin et al. (1995). *Diagnostic Immunopathology* 2nd edition, Raven Press, New York.

Cook S. J. and F. McCormick (1993). Inhibition by cAMP of Ras-dependent activation of Raf. *Science* 262:1069-1072.

Dawson D. L., B. S. Cutler, M. H. Meissner, D. E. Strandness Jr. (1998). Cilostazol has beneficial effects in treatment of intermittent claudication: results from a multicenter, randomized, prospective, double-blind trial. *Circulation* 98:678-686.

Dodge K., S. Khouangsathiene, M. S. Kapiloff et al. (2001). mAKAP assembles a protein kinase A/PDE4 phosphodiesterase cAMP signaling module. *EMBO J.* 20:1921-1930.

Duan C., J. R. Bauchat, and T. Hsieh (2000). Phosphatidylinositol 3-kinase is required for insulin-like growth factor-1-induced vascular smooth muscle cell proliferation and migration. *Circ. Res.* 86:15-23.

Elbashir et al. (2001). *Nature* 411:494-498.

Fentzke R. C., C. E. Korcarz, R. M. Lang, H. Lin, and J. M. Leiden (1998). Dilated cardiomyopathy in transgenic mice expressing a dominant-negative CREB transcription factor in the heart. *J. Clin. Invest.* 101:2415-2426.

Fischmeister R. and H. C. Hartzell (1990). Regulation of calcium current by low-$K_m$ cyclic AMP phosphodiesterases in cardiac cells. *Mol. Pharmacol.* 38:426-433.

Florio S. K., R. K. Prusti, and J. A. Beavo (1996). Solubilization of membrane-bound rod phosphodiesterase by the rod phosphodiesterase recombinant delta subunit. *J. Biol. Chem.* 271:24036-24047.

Forster and Symons (1987). *Cell* 49:211-220.

Fransen M., P. P. Van Veldhoven, and S. Subramani (1999). Identification of peroxisomal proteins by using M13 phage protein VI phage display: molecular evidence that mammalian peroxisomes contain a 2,4-dienoyl-CoA reductase. *J. Biol. Chem.* 340:561-568.

Freifelder (1982). *Physical Biochemistry Applications to Biochemistry and Molecular Biology* 2nd ed., Wm. Freeman and Co., New York, N.Y.

Fu H., R. R. Subramanian, and S. C. Masters (2000). 14-3-3 proteins: structure, function, and regulation. *Annu. Rev. Pharmacol. Toxicol.* 40:617-647.

Fujio Y., T. Nguyen, D. Wencker, R. N. Kitsis, and K. Walsh (2000). Akt promotes survival of cardiomyocytes in vitro and protects against ischemia-reperfusion injury in mouse heart. *Circulation* 101:660-667.

Gefter et al. (1977). *Somatic Cell Genet.* 3:231-236.

Gibson W. (1974). Polyoma virus proteins: a description of the structural proteins of the virion based on polyacrylamide gel electrophoresis and peptide analysis. *Virology* 62(2):319-36.

Goding (1986). In: *Monoclonal Antibodies: Principles and Practice* 2d ed., Orlando, Fla., Academic Press, pp. 60-61, 65-66, 71-74.

Granovsky A. E., K. G. Muradov, and N. O. Artemyev (2000). Inhibition of photoreceptor cGMP phosphodiesterase by its gamma subunit. *Methods Enzymol.* 315:635-646.

Grant P. G., A. F. Mannarino, and R. W. Colman (1988). cAMP-mediated phosphorylation of the low-Km cAMP phosphodiesterase markedly stimulates its catalytic activity. *Proc. Natl. Acad. Sci.* 85:9071-9075.

Harlow and Lane (1988). *Antibodies: A Laboratory Manual*, Cold Spring Harbor Laboratory, Cold Spring Harbor, N.Y.

Haseloff and Gerlach (1988). *Nature* 334:585-591.

Hayes J. S., L. L. Brunton, and S. E. Mayer (1980). Selective activation of particulate CAMP-dependent protein kinase by isoproterenol and prostaglandin $E_1$. *J. Biol. Chem.* 255: 5113-5119.

He R., N. Komas, D. Ekholm, T. Murata, M. Taira, S. Hockman, E. Degerman, and V. C. Manganiello (1998). Expression and characterization of deletion recombinants of two cGMP-inhibited cyclic nucleotide phosphodiesterases (PDE-3). *Cell Biochem. Biophys.* 29:89-111.

Hess et al. (1968). *J. Adv. Enzyme Reg.* 7:149.

Hitzeman et al. (1980). *J. Biol. Chem.* 255:2073.

Hoffmann R., G. S. Baillie, S. J. MacKenzie, S. J. Yarwood, and M. D. Houslay (1999). The MAP kinase ERK2 inhibits the cyclic AMP-specific phosphodiesterase HSPDE4D3 by phosphorylating it at Ser579. *EMBO J.* 18:893-903.

Hoffmann R., I. R. Wilkinson, J. F. McCallum, P. Engels, and M. D. Houslay (1998). cAMP-specific phosphodiesterase HSPDE4D3 mutants which mimic activation and changes in rolipram inhibition triggered by protein kinase A phosphorylation of Ser-54. *Biochem. J.* 333:139-149.

Hohl C. M. and Q. Li (1991). Compartmentation of cAMP in adult canine ventricular myocytes. Relation to single-cell free $Ca^{2+}$ transients. *Circ. Res.* 69:1369-1379.

Holland et al. (1978). *Biochemistry* 17:4900.

Innis et al. (1990). *PCR Protocols*, Academic Press, Inc., San Diego Calif.

Inoue Y., K. Toga, T. Sudo, K. Tachibana, S. Tochizawa, Y. Kimura, Y. Yoshida, and H. Hidaka (2000). Suppression of arterial intimal hyperplasia by cilostamide, a cyclic nucleotide phosphodiesterase 3 inhibitor, in a rat balloon double-injury model. *Br. J. Pharmacol.* 30:231-241.

Jurevicius J. and R. Fischmeister (1996). cAMP compartmentation is responsible for a local activation of cardiac $Ca^{2+}$ channels by beta-adrenergic agonists. *Proc. Natl. Acad. Sci.* 93:295-299.

Kasuya J., H. Goko, and Y. Fujita-Yamaguchi (1995). Multiple transcripts for the human cardiac form of the cGMP-inhibited cAMP phosphodiesterase. *J. Biol. Chem.* 270: 14305-14312.

Kasuya J., S. J. Liang, H. Goko, S. H. Park, K. Kato, Z. D. Xu, S. Hockman, V. C. Manganiello and Y. Fujita-Yamaguchi (2000). Cardiac type cGMP-inhibited phosphodiesterase (PDE3A) gene structure: Similarity and difference to adipocyte type PDE3B gene. *Biochem. Biophys. Res. Comm.* 268:827-834.

Kenan Y., T. Murata, S. Yasmin, E. Degerman and V. C. Manganiello (2000). Functions of the N-terminal region of cyclic nucleotide phosphodiesterasae 3 isoforms. *J. Biol. Chem.* 275:12331-12338.

Kingsman et al. (1979). *Gene* 7:141.

Kitamura T., Y. Kitamura, S. Kuroda et al. (1999). Insulin-induced phosphorylation and activation of cyclic nucleotide phosphodiesterase 3B by the serine-threonine kinase akt. *Mol. Cell. Biol.* 19:6286-6296.

Kohler and Milstein (1976). *Eur. Immunol.* 6:511-519.

Kohler and Milstein (1975). *Nature* 256:495-497.

Krall J., K. Taskén, J. Staheli, T. Jahnsen, and M. A. Movsesian (1999). Identification and quantitation of cAMP-dependent protein kinase R subunit isoforms in subcellular fractions of human myocardium. *J. Mol. Cell Cardiol.* 31:971-980.

Kwoh et al. (1989). *Proc. Nat. Acad. Sci. USA* 86:1173.

Kyte and Doolittle (1982). *J. Mol. Biol.* 157(1):105-132.

Lazou A., M. A. Bogoyevitch, A. Clerk, S. J. Fuller, C. J. Marshall, and P. H. Sugden (1994). Regulation of mitogen-activated protein kinase cascade in adult rat heart preparations in vitro. *Circ. Res.* 75:932-941.

Liu H. and D. H. Maurice (1998). Expression of cyclic GMP-inhibited phosphodiesterases 3A and 3B (PDE3A and PDE3B) in rat tissues: differential subcellular localization and regulated expression by'cyclic AMP. *Br. J. Pharmacol.* 125:1501-1510.

Lopez-Aparicio P., P. Belfrage, V. C. Manganiello, T. Kono, and E. Degerman (1993). Stimulation by insulin of a serine kinase in human platelets that phosphorylates and activates the cGMP-inhibited cAMP phosphodiesterase. *Biochem. Biophys. Res. Commun.* 193:1137-44.

Lowy et al. (1980). *Cell* 22:817.

Luo K., T. R. Hurley and B. M. Sefton (1990). Transfer of proteins to membranes facilitates both cyanogen bromide cleavage and two-dimensional proteolytic mapping. *Oncogene* 5:921-3.

Lutz S., R. Mura, D. Baltus, M. A. Movsesian, W. Kübler, and F. Niroomand (2001). Increased activity of membrane-associated nucleoside diphosphate kinase and inhibition of cAMP synthesis in failing human myocardium. *Cardiovasc. Res.* 49:48-55.

Matsui T., L. Li, F. del Monte, Y. Fukui, T. F. Franke, R. J. Hajjar, and A. Rosenzweig (1999). Adenoviral gene transfer of activated phosphatidylinositol 3'-kinase and akt inhibits apoptosis of hypoxic cardiomyocytes in vitro. *Circulation* 100:2373-237.

McPhee I., S. J. Yarwood, G. Scotland et al. (1999). Association with the SRC family tyrosyl kinase LYN triggers a conformational change in the catalytic region of human cAMP-specific phosphodiesterase HSPDE4A4B. *J. Biol. Chem.* 274:11796-11810.

Meacci E., M. Taira, M. Moos Jr., C. J. Smith, M. A. Movsesian, E. Degerman, P. Belfrage, and V. C. Manganiello (1992). Molecular cloning and expression of human myocardial cGMP-inhibited cAMP phosphodiesterase. *Proc. Natl. Acad. Sci. USA* 89:3721-3725.

Merrifield (1986). *Science* 232:341-347.

Minamisawa S., M. Hoshijima, G. Chu et al. (1999). Chronic phospholamban-sarcoplasmic reticulum calcium ATPase interaction is the critical calcium cycling defect in dilated cardiomyopathy. *Cell* 99:313-322.

Movsesian M. A., M. Nishikawa and R. S. Adelstein (1984). Phosphorylation of phospholamban by calcium-activated, phospholipid-dependent protein kinase. *J. Biol. Chem.* 259:8029-8032.

Movsesian M. A. (1999). Beta-adrenergic receptor agonists and cyclic nucleotide phosphodiesterase inhibitors: shifting the focus from inotropy to cAMP. *J. Am. Coll. Cardiol.* 34:318-324.

Movsesian M. A. (2000). Therapeutic potential of cyclic nucleotide phosphodiesterase inhibitors in heart failure. *Expert Opinion on Investigational Drugs* 9:963-973.

Mulligan et al. (1981). *Proc. Nat'l Acad. Sci. USA* 78:2072.

Nakamura et al. (1987). In: *Handbook of Experimental Immunology* (4th Ed.), E. Weir, L. A. Herzenberg, C. Blackwell, and L. Herzenberg (eds), Vol. 1, Chapter 27, Blackwell Scientific Publ., Oxford, 1987.

Nony P., J. P. Boissel, M. Lièvre, A. Leizorovicz, M. C. Haugh, S. Fareh, B. de Breyne (1994). Evaluation of the effect of phosphodiesterase inhibitors on mortality in chronic heart failure patients. *Eur. J. Clin. Pharmacol.* 46:191-196.

O'Hare et al. (1981). *Proc. Nat'l Acad. Sci. USA* 78:1527.

Osinski M. T. and K. Schror (2000). Inhibition of platelet-derived growth factor-induced mitogenesis by phosphodiesterase 3 inhibitors: role of protein kinase A in vascular smooth muscle cell mitogenesis. *Biochem. Pharmacol.* 60:381-387.

Palukaitis et al. (1979). *Virology* 99:145-151.

Palmer D., D. R. Raymond, H. A. Dunkerley, D. G. Tilley, and D. H. Maurice (2000). Human phosphodiesterase 3B interacts with the 14-3-3 family of signaling molecules. *Mol. Biol. Cell* 11:250a.

Park S. W., C. W. Lee, H. S. Kim, et al. (2000). Effects of cilostazol on angiographic restenosis after coronary stent placement. *Am. J. Cardiol.* 86:499-503.

Perriman et al. (1992). *Gene* 113:157-163.

Prody et al. (1986). *Science* 231:1577-1580.

Rahn T., L. Rönnstrand, M. J. Leroy, C. Wernstedt, H. Tornqvist, V. C. Manganiello, P. Belfrage, and E. Degerman (1996). Identification of the site in the cGMP-inhibited phosphodiesterase phosphorylated in adipocytes in response to insulin and isoproterenol. *J. Biol. Chem.* 271:11575-11580.

Rapundalo S. T., R. J. Solaro and E. G. Kranias (1989). Inotropic responses to isoproterenol and phosphodiesterase inhibitors in intact guinea pig hearts: comparison of cyclic AMP levels and phosphorylation of sarcoplasmic reticulum and myofibrillar proteins. *Circ. Res.* 64:104-111.

Rascòn A., E. Degerman, M. Taira, E. Meacci, C. J. Smith, V. Manganiello, P. Belfrage, and H. Tornqvist (1994). Identification of the phosphorylation site in vitro for cAMP-dependent protein kinase on the rat adipocyte cGMP-inhibited cAMP phosphodiesterase. *J. Biol. Chem.* 269:11962-11966.

Reinhardt R. R., E. Chin, J. Zhou, et al. (1995). Distinctive anatomical patterns of gene expression for cGMP-inhibited cyclic nucleotide phosphodiesterases. *J. Clin. Invest.* 95:1528-1538.

*Remington's Pharmaceutical Sciences*, 15th ed., pp. 1035-1038 and 1570-1580.

Resjö S., A. Oknianska, S. Zolnierowicz, V. Manganiello, and E. Degerman (1999). Phosphorylation and activation of phosphodiesterase type 3B (PDE3B) in adipocytes in response to serine/threonine phosphatase inhibitors: deactivation of PDE3B in vitro by protein phosphatase type 2A. *J. Biol. Chem.* 341:839-845.

Rocic P. and P. A. Lucchesi (2001 Mar. 21 [epub ahead of print]). Down-regulation by antisense oligonucleotides establishes a role for the proline-rich tyrosine kinase PYK2 in angiotensin II-induced signaling in vascular smooth muscle. *J. Biol. Chem.*

Rondinone C. M., E. Carvalho, T. Rahn, V. C. Manganiello, E. Degerman, and U. P. Smith (2000). Phosphorylation of PDE3B by phosphatidylinositol 3-kinase associated with the insulin receptor. *J. Biol. Chem.* 275:10093-10098.

Rosenmund C., C. W. Carr, S. E. Bergeson, G. Nilayer, J. D. Scott, and G. L. Westbrook (1994). Anchoring of protein kinase A is required for modulation of AMPA/kainate receptors on hippocampal neurons. *Nature* 368:853-856.

Sambrook, Fritsch, and Maniatis (1989). *Molecular Cloning: A Laboratory Manual*, 2nd Ed., Cold Spring Harbor Press, Cold Spring Harbor, N.Y.

Sandirasegarane L., R. Charles, N. Bourbon, and M. Kester (2000). NO regulates PDGF-induced activation of PKB but not ERK in A7r5 cells: implications for vascular growth arrest. *Am. J. Physiol. Cell Physiol.* 279:C225-35.

Santerre et al. (1984). *Gene* 30:147-156.

Sarver, et al. (1990). *Science* 247:1222-1225.

Scanlon et al. (1991). *Proc. Natl. Acad. Sci. USA* 88:10591-10595.

Schillace R. V., J. W. Voltz, A. T. Sim, S. Shenolikar, and J. D. Scott (2001). Multiple interactions within the AKAP220 signaling complex contribute to protein phosphatase 1 regulation. *J. Biol. Chem.* 276:12128-12134.

Shakur Y., L. S. Hoist, T. R. Landstrom, M. A. Movsesian, E. Degerman, and V. Manganiello (2000a). Regulation and function of the cyclic nucleotide phosphodiesterase PDE3 gene family. *Prog. Nucleic Acid Res. Mol. Biol.* 66:241-77.

Shakur Y., K. Takeda, Y. Kenan, Z. X. Yu, G. Rena, D. Brandt, M. D. Houslay, E. Degerman, V. J. Ferrans, and V. C. Manganiello (2000b). Membrane localization of cyclic nucleotide phosphodiesterase 3 (PDE3). *J. Biol. Chem.* 49:38749-38761.

Shaywitz A. J. and M. E. Greenberg (1999). CREB: a stimulus-induced transcription factor activated by a diverse array of extracellular signals. *Annu. Rev. Biochem.* 68:821-861.

Simmerman H. K. and L. R. Jones (1998). Phospholamban: protein structure, mechanism of action, and role in cardiac function. *Physiol. Rev.* 78:921-947.

Sioud et. al. (1992). *J. Mol. Biol.* 223:831-835.

Smith C. J., J. Krall, V. C. Manganiello, and M. A. Movsesian (1993). Cytosolic and sarcoplasmic reticulum-associated low $K_m$, cGMP-inhibited cAMP phosphodiesterase in mammalian myocardium. *Biochem. Biophys. Res. Comm.* 190:516-521.

Smith C. J., V. Vasta, E. Degerman, P. Belfrage, and V. C. Manganiello (1991). Hormone-sensitive cGMP-inhibited cAMP phosphodiesterase in rat adipocytes: Regulation of insulin- and cAMP-dependent activation by phosphorylation. *J. Biol. Chem.* 266:13385-13390.

Sonnenburg W. K., D. Seger, K. S. Kwak, J. Huang, H. Charbonneau, and J. A. Beavo (1995). Identification of inhibitory and calmodulin-binding domains of the PDE1A1 and PDE1A2 calmodulin-stimulated cyclic nucleotide phosphodiesterases. *J. Biol. Chem.* 270: 30989-31000.

Stewart and Young (1984). *Solid Phase Peptide Synthesis* 2d. ed., Pierce Chemical Co.

Stinchcomb et al. (1979). *Nature* 282:39.

Symons (1992). *Annu. Rev. Biochem.* 61:641-671.

Symons (1981). *Nucl. Acids Res.* 9:6527-6537.

Szybalska et al. (1962). *Proc. Nat'l Acad. Sci. USA* 48:2026.

Taira M., S. C. Hockman, J. C. Calvo, M. Taira, P. Belfrage, and V. C. Manganiello (1993). Molecular cloning of the rat adipocyte hormone-sensitive cyclic GMP-inhibited cyclic nucleotide phosphodiesterase. *J. Biol. Chem.* 268:18573-18579.

Tam et al. (1983). *J. Am. Chem. Soc.* 105:6442.

Tang K. M., E. K. Jang, and R. J. Haslam (1997). Expression and mutagenesis of the catalytic domain of cGMP-inhibited phosphodiesterase (PDE3) cloned from human platelets. *Biochem. J.* 323:217-224.

Tschemper et al. (1980). *Gene* 10:157.

Walker et al. (1992). *Proc. Nat'l Acad. Sci. USA,* 89:392-396.

Wigler et al. (1977). *Cell* 11:223.

Wigler et al. (1980). *Proc. Nat'l Acad. Sci. USA,* 77:3567.

Wu et al. (1989). *Genomics* 4:560.

Wu W., W. L. Lee, Y. Y. Wu, et al. (2000). Expression of constitutively active phosphatidylinositol 3 kinase inhibits activation of caspase 3 and apoptosis of cardiac muscle cells. *J. Biol. Chem.* 275:40113-40119.

Xiao R. P., C. Hohl, R. Altschuld, et al. (1993). $\beta_1$-adrenoceptor stimulation and $\beta_2$-adrenoceptor stimulation differ in their effects on contraction, cytosolic $Ca^{2+}$, and $Ca^{2+}$ current in single rat ventricular cells. *Circ. Res.* 73:286-300.

Xiao R. P., C. Hohl, R. Altschuld et al. (1994). $\beta_2$-adrenergic receptor-stimulated increase in cAMP in rat heart cells is not coupled to changes in $Ca^{2+}$ dynamics, contractility, or phospholamban phosphorylation. *J. Biol. Chem.* 269: 19151-19156.

Xiao R. P. and E. G. Lakatta (1993). $\beta_1$-adrenoreceptor stimulation and $\beta_2$-adrenoreceptor stimulation differ in their effects on concentration, cytosolic $Ca^{2+}$, and $Ca^{2+}$ current in single rat ventricular cells. *Circ. Res.* 73:286-300.

Xu R. X., A. M. Hassell, D. Vanderwall et al. (2000). Atomic structure of PDE4: insights into phosphodiesterase mechanism and specificity. *Science* 288:1822-1825.

Yarwood S. J., M. R. Steele, G. Scotland, M. D. Houslay, and G. B. Bolger (1999). The RACK1 signaling scaffold protein selectively interacts with the cAMP-specific phosphodiesterase PDE4D5 isoform. *J. Biol. Chem.* 274: 14909-14917.

Yuan and Altman (1994). *Science* 263:1269-1273.

Yuan et al. (1992). *Proc. Natl. Acad. Sci. USA* 89:8006-8010.

Zhang W. and R. W. Colman (2000). Conserved amino acids in metal-binding motifs of PDE3A are involved in substrate and inhibitor binding. *Blood* 95:3380-3386.

Zhao A. Z., K. E. Bornfeldt and J. A. Beavo (1998). Leptin inhibits insulin secretion by activation of phosphodiesterase 3B. *J. Clin. Invest.* 102:869-873.

Zozulya S., M. Lioubin, R. J. Hill, C. Abram, and M. L. Gishizky (1999). Mapping signal transduction pathways by phage display. *Nature Biotech.* 17:1193-1198.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,215,051
U.S. Pat. No. 4,275,149
U.S. Pat. No. 4,277,437
U.S. Pat. No. 4,366,241
U.S. Pat. No. 4,554,101
U.S. Pat. No. 5,405,766
U.S. Pat. No. 5,565,332
U.S. Pat. No. 5,596,079
U.S. Pat. No. 5,614,396
U.S. Pat. No. 5,624,830
U.S. Pat. No. 5,858,804
U.S. Pat. No. 5,948,627
U.S. Pat. No. 5,986,076
U.S. Pat. No. 6,031,071
U.S. Pat. No. 6,068,829
U.S. Pat. No. 6,071,394

What is claimed is:

1. A method of identifying an isoform-selective regulator of PDE3, said method comprising:
   (a) obtaining a first isolated polypeptide (PDE3A1), wherein said first isolated polypeptide (PDE3A1) has an amino acid sequence that is at least 95% homologous to the amino acid sequence of SEQ ID NO:1;
   (b) identifying at least one test compound that binds to said first isolated polypeptide, (PDE3A1);
   (c) assaying the at least one test compound for its ability to interfere with binding of said first isolated polypeptide (PDE3A1), to cAMP, cGMP, or another polypeptide;
   (d) assaying the at least one test compound for its ability to interfere with binding of a second isolated polypeptide (PDE3A2), to cAMP, cGMP, or a another polypeptide; and
   (e) identifying said at least one test compound as an isoform-selective regulator of PDE3 when said ability to interfere with said binding of cAMP, cGMP, or another polypeptide to said first isolated polypeptide (PDE3A1) is greater than said ability to interfere with binding of cAMP, cGMP or another polypeptide to said second isolated polypeptide (PDE3A2).

2. The method according to claim 1, wherein the first isolated (PDE3A1) polypeptide is identical in sequence to SEQ ID NO:1.

3. The method according to claim 1, wherein the second isolated polypeptide (PDE3A2) is identical in sequence to SEQ ID NO:2.

4. The method of claim 1, wherein the second isolated polypeptide (PDE3A2) is identical in sequence to SEQ ID NO:3.

5. The method according to claim 1, wherein the first isolated polypeptide (PDE3A1) has the sequence of SEQ ID NO:1, with at least one substitution mutation at serine residues 292, 293, 312 or 438.

6. The method according to claim 5, wherein the substitution mutation substitutes an alanine or an aspartate residue for the serine residue.

7. The method according to claim 1, wherein the second isolated polypeptide (PDE3A2) has the sequence of SEQ ID NO:2, with at least one substitution mutation at serine residues 312 or 438.

8. The method according to claim 7, wherein the substitution mutation substitutes an alanine or an aspartate residue for the serine residue.

9. The method of claim 1, wherein the another polypeptide is a protein kinase, a protein phosphatase, PDE3A-binding proteins or a protein phosphorylase.

10. The method of claim 1 further including a step of using said at least one test compound to regulate at least one of the following of phosphorylation, dephosphorylation, catalytic activity, intracellular localization or protein-protein interactions of PDE3A2.

* * * * *